United States Patent
Geddes

(10) Patent No.: US 9,556,474 B2
(45) Date of Patent: *Jan. 31, 2017

(54) MULTICOLOR MICROWAVE-ACCELERATED METAL-ENHANCED FLUORESCENCE (M-MAMEF)

(71) Applicant: Chris D. Geddes, Bel-Air, MD (US)

(72) Inventor: Chris D. Geddes, Bel-Air, MD (US)

(73) Assignee: Chris D. Geddes, Bel-Air, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/287,541

(22) Filed: May 27, 2014

(65) Prior Publication Data
US 2014/0256059 A1 Sep. 11, 2014

Related U.S. Application Data

(63) Continuation of application No. 13/420,702, filed on Mar. 15, 2012, now Pat. No. 8,735,175.
(Continued)

(51) Int. Cl.
*G01N 33/543* (2006.01)
*G01N 33/553* (2006.01)
(Continued)

(52) U.S. Cl.
CPC ............. *C12Q 1/6816* (2013.01); *B82Y 15/00* (2013.01); *G01N 21/648* (2013.01);
(Continued)

(58) Field of Classification Search
CPC .................... G01N 33/54346; G01N 33/553
See application file for complete search history.

(56) References Cited

U.S. PATENT DOCUMENTS

| 5,017,009 A | 5/1991 | Schutt et al. |
| 5,449,918 A | 9/1995 | Krull et al. |

(Continued)

FOREIGN PATENT DOCUMENTS

| JP | 2009-058474 | 3/2009 |
| WO | WO89/09408 | 10/1989 |

(Continued)

OTHER PUBLICATIONS

Aslan, K. et al. Metal-enhanced fluorescence: an emerging tool in biotechnology, Current Opinion in Biotechnology 2005, 16, 55-62.
(Continued)

*Primary Examiner* — Erik B Crawford
*Assistant Examiner* — Gary E Hollinden
(74) *Attorney, Agent, or Firm* — Marianne Fuierer; Moore & Van Allen, PLLC

(57) ABSTRACT

The present invention relates to the use of multiple different light emitting molecules that emit different and detectable emission signals to provide systems and methods to detect different target products in a single assay sample, wherein the different light emitting molecules are positioned an optimal distance from metallic particles thereby enhancing emissions. Preferably, the systems and methods further comprise use of either microwave or sonic energy to increase binding reactions, timing of such reactions within the assay sample and reduce background non-specific biological absorption.

4 Claims, 36 Drawing Sheets

Related U.S. Application Data

(60) Provisional application No. 61/454,078, filed on Mar. 18, 2011.

(51) Int. Cl.

| | | |
|---|---|---|
| *C12Q 1/68* | (2006.01) | |
| *G01N 21/64* | (2006.01) | |
| *G01N 21/76* | (2006.01) | |
| *B82Y 15/00* | (2011.01) | |

(52) U.S. Cl.
CPC ... *G01N 21/6428* (2013.01); *G01N 33/54346* (2013.01); *G01N 33/54353* (2013.01); *G01N 33/54373* (2013.01); *G01N 33/553* (2013.01); *G01N 21/6408* (2013.01); *G01N 21/6489* (2013.01); *G01N 21/76* (2013.01); *G01N 21/763* (2013.01); *G01N 2021/6432* (2013.01); *G01N 2021/6441* (2013.01)

(56) References Cited

U.S. PATENT DOCUMENTS

| | | |
|---|---|---|
| 5,841,143 A | 11/1998 | Tuma et al. |
| 5,866,433 A | 2/1999 | Schalkhammer et al. |
| 6,329,209 B1 | 12/2001 | Wagner et al. |
| 6,589,779 B1 | 7/2003 | McDevitt et al. |
| 6,867,007 B2 | 3/2005 | Kauvar |
| 7,095,502 B2 | 8/2006 | Lakowicz et al. |
| 7,253,452 B2 | 8/2007 | Steckel et al. |
| 7,348,182 B2 | 3/2008 | Martin et al. |
| 7,351,590 B2 | 4/2008 | Martin |
| 7,400,397 B2 | 7/2008 | Lakowicz et al. |
| 7,648,834 B2 | 1/2010 | Moore |
| 7,718,445 B2 | 5/2010 | Martin |
| 7,718,804 B2 | 5/2010 | Geddes et al. |
| 7,732,215 B2 | 6/2010 | Geddes et al. |
| 7,939,333 B2 | 5/2011 | Geddes et al. |
| 8,008,067 B2 | 8/2011 | Geddes et al. |
| 8,034,633 B2 | 10/2011 | Geddes |
| 8,075,956 B2 | 12/2011 | Geddes et al. |
| 8,101,424 B2 | 1/2012 | Geddes |
| 8,114,598 B2 | 2/2012 | Geddes et al. |
| 8,182,878 B2 | 5/2012 | Geddes et al. |
| 8,318,087 B2 | 11/2012 | Geddes |
| 8,338,602 B2 | 12/2012 | Geddes et al. |
| 2003/0228682 A1 | 12/2003 | Lakowicz et al. |
| 2004/0058458 A1 | 3/2004 | Anker et al. |
| 2005/0053974 A1 | 3/2005 | Lakowicz et al. |
| 2005/0221358 A1 | 10/2005 | Carrillo et al. |
| 2006/0147927 A1 | 7/2006 | Geddes et al. |
| 2006/0257992 A1 | 11/2006 | McDevitt et al. |
| 2007/0115474 A1 | 5/2007 | Chaton et al. |
| 2007/0269826 A1 | 11/2007 | Geddes et al. |
| 2007/0278607 A1 | 12/2007 | Gruhlke et al. |
| 2008/0038830 A1 | 2/2008 | Ure et al. |
| 2008/0215122 A1 | 9/2008 | Geddes et al. |
| 2008/0241866 A1 | 10/2008 | Korlach et al. |
| 2008/0285040 A1 | 11/2008 | Fourkas et al. |
| 2009/0022766 A1 | 1/2009 | Geddes et al. |
| 2009/0142847 A1 | 6/2009 | Geddes et al. |
| 2009/0325199 A1 | 12/2009 | Geddes et al. |
| 2010/0028983 A1 | 2/2010 | Geddes |
| 2010/0035335 A1 | 2/2010 | Lakowicz et al. |
| 2010/0062545 A1 | 3/2010 | Geddes et al. |
| 2010/0209937 A1 | 8/2010 | Geddes et al. |
| 2010/0297016 A1 | 11/2010 | Geddes et al. |
| 2011/0020946 A1 | 1/2011 | Geddes |
| 2011/0136154 A1 | 6/2011 | Geddes |
| 2011/0207236 A1 | 8/2011 | Geddes |
| 2011/0281775 A1 | 11/2011 | Alexandre et al. |
| 2012/0021443 A1 | 1/2012 | Geddes |
| 2012/0028270 A1 | 2/2012 | Geddes |
| 2012/0088691 A1 | 4/2012 | Chen et al. |
| 2012/0091349 A1 | 4/2012 | Geddes |
| 2012/0107952 A1 | 5/2012 | Geddes et al. |
| 2012/0142552 A1 | 6/2012 | Geddes et al. |
| 2012/0238035 A1 | 9/2012 | Geddes |
| 2012/0282630 A1 | 11/2012 | Geddes |
| 2012/0301886 A1 | 11/2012 | Farrell et al. |
| 2013/0020503 A1 | 1/2013 | Geddes |

FOREIGN PATENT DOCUMENTS

| | | |
|---|---|---|
| WO | WO2004/024191 | 3/2004 |
| WO | WO2008121097 | 10/2008 |
| WO | WO2009134527 | 11/2009 |

OTHER PUBLICATIONS

Aslan, K. et al. Microwave-accelerated metal-enhanced fluorescence (MAMEF): application to ultra fast and sensitive clinical assays, Journal of Fluorescence 2006, 16, 3-8.

Aslan, K. et al. Microwave-Accelerated Metal-Enhanced Fluorescence (MAMEF) with silver colloids in 96-well plates: Application to ultra fast and sensitive immunoassays, High Throughput Screening and drug discovery, Journal of Immunological Methods, 312 (2006) 137-147.

Aslan, K. et al. Fast and sensitive DNA hybridization assays using microwave-accelerated metal-enhanced fluorescence, Biochemical and Biophysical Research Communications 2006, 348, 612-17.

Aslan, K. et al. Extraction and detection of DNA from Bacillus anthracis spores and the vegetative cells within 1 min, Analytical Chemistry 2008, 80, 4125-32.

Aslan, K. et al. A review of an ultrafast and sensitive bioassay platform technology: microwave-accelerated metal-enhanced fluorescence, Plasmonics 2008, 3, 89-101.

Bae, J. H. et al. Template-blocking PCR: an advanced PCR technique for genome walking, Analytical Biochemistry 2010, 398, 112-16.

Caraway, N. P. et al. Cancer Cytopathology 2010, 118, 175-83.

Chiminqgi, M. et al. Specific real-time PCR vs. fluorescent dyes for serum free DNA quantification, Clinical Chemistry and Laboratory Medicine 2007, 45, 993-95.

Cosa, G. et al. Photophysical properties of fluorescent DNA-dyes bound to single- and double-stranded DNA in aqueous buffered solution, Photochem.Photobiol. 2001, 73, 585-99.

Crosby, L. D. et al. DNA hydration studied by pressure perturbation scanning microcalorimetry, Molecular and Cellular Probes 2007, 21, 140-47.

Dragan, A. I. et al. Methods Enzymol. 2008, 450, 185-99.

Dragan, A. I. et al. Characterization of PicoGreen interaction with dsDNA and the origin of its fluorescence enhancement upon binding, Biophys.J. 2010, in press.

Dragan,A.I. et al. Two-Colored, 30 second microwave-accelerated metal-enhanced fluorescence assays: A new rapid catch and signal (RCS) technology. Journal of Immunological Methods (2011) 366:1-7.

Dragan, A. I. et al. Metal-enhanced PicoGreen fluorescence: application for double-stranded DNA quantification, Anal.Biochem. 2010, 396, 8-12.

Dragan, A. I. et al. Biopolymers 2009, 91, 95-101.

Dragan, A. I. et al. J.Immunol.Methods 2010.

Drexhage, K. H., Influence of a dielectric interface on fluorescence decay time, J.Lumin 1970, 1, 693-701.

Favicchio, R. et al. Methods Mol.Biol. 2009, 543, 589-611.

Geddes, C. D. et al. Journal of Fluorescence 2002, 12, 121-29.

Geddes, C.D. et al. Metal-enhanced fluorescence (MEF) due to silver colloids on a planar surface: potential applications of indocyanine green to in vivo imaging, J. Phys. Chem. A, 107 (2003), p. 3443.

Geddes, C.D. et al. Silver fractal-like structures for metal-enhanced fluorescence: enhanced fluorescence intensities and increased probe photostabilities, J. Fluoresc., 13 (2003), p. 267.

Hacia, J. G., Resequencing and mutational analysis using oligonucleotide microarrays, Nat.Genet. 1999, 21, 42-47.

Jelesarov, I. et al. The energetics of HMG box interactions with DNA: thermodynamic description of the target DNA duplexes, J.Mol.Biol. 1999, 294, 981-95.

(56) References Cited

OTHER PUBLICATIONS

Koripelly, G. et al. Bioconjugate Chemistry 2010, 21, 2103-09.

Lakowicz, J.R. et al. Radiative decay engineering. 2. Effects of silver island films on fluorescence intensity, lifetimes, and resonance energy transfer, Anal.Biochem. 2002, 301, 261-77.

McCabe, M. et al. Adv.Exp.Med.Biol. 2005, 566, 143-49.

Mullis, K. B., The first polymerase chain reaction, Scientist 2003, 17, 11.

Nelson, E. Dynamical Theories of Brownian Motion, Princeton University Press: 1967.

Park, J. H. et al. Appl.Phys Lett. 2010, 96, 123703.

Persson, B. N. J., Theory of damping of excited molecules located above a metalic-surface, J.Phys.C: Solid State Phys 1978, 11, 4251-69.

Previte, M.J. et al. Real-time thermal imaging of microwave accelerated metal-enhanced fluorescence (MAMEF) based assays on sapphire plates, J. Fluoresc., 17 (2007), p. 639.

Pribik, R. et al. Metal-Enhanced Fluorescence (MEF): Physical characterization of Silver-island films and exploring sample geometries, Chemical Physics Letters 2009, 478, 70-74.

Privalov, P. L. et al. What drives proteins into the major or minor grooves of DNA?, J.Mol.Biol. 2007, 365, 1-9.

Saiki, R. K. et al. Enzymatic amplification of beta-globin genomic sequences and restriction site analysis for diagnosis of sickle cell anemia, Science 1985, 230, 1350-54.

Singer, V. L. et al. Characterization of PicoGreen reagent and development of a fluorescence-based solution assay for double-stranded DNA quantitation, Anal.Biochem. 1997, 249, 228-38.

Tennant, S.M. et al. Ultra-fast and sensitive detection of non-typhoidal *Salmonella* using microwave-accelerated metal-enhanced fluorescence ("MAMEF"), PLoS.One. 6 (2011) e18700.

Tonooka, Y. et al. Comparison and critical evaluation of PCR-mediated methods to walk along the sequence of genomic DNA, Applied Microbiology and Biotechnology 2009, 85, 37-43.

Zhang, Z. et al. Development of a Microwave-Accelerated Metal-Enhanced Fluorescence 40 seconds, < 100 cfu/ml point of care assay for the detection of Chlamydia Trachomatis., IEEE Transactions on Biomedical Engineering, 58 (2011) 781-784.

Zipper, H. et al. Investigations on DNA intercalation and surface binding by SYBR Green I, its structure determination and methodological implications, Nucleic Acids Res. 2004, 32, e103.

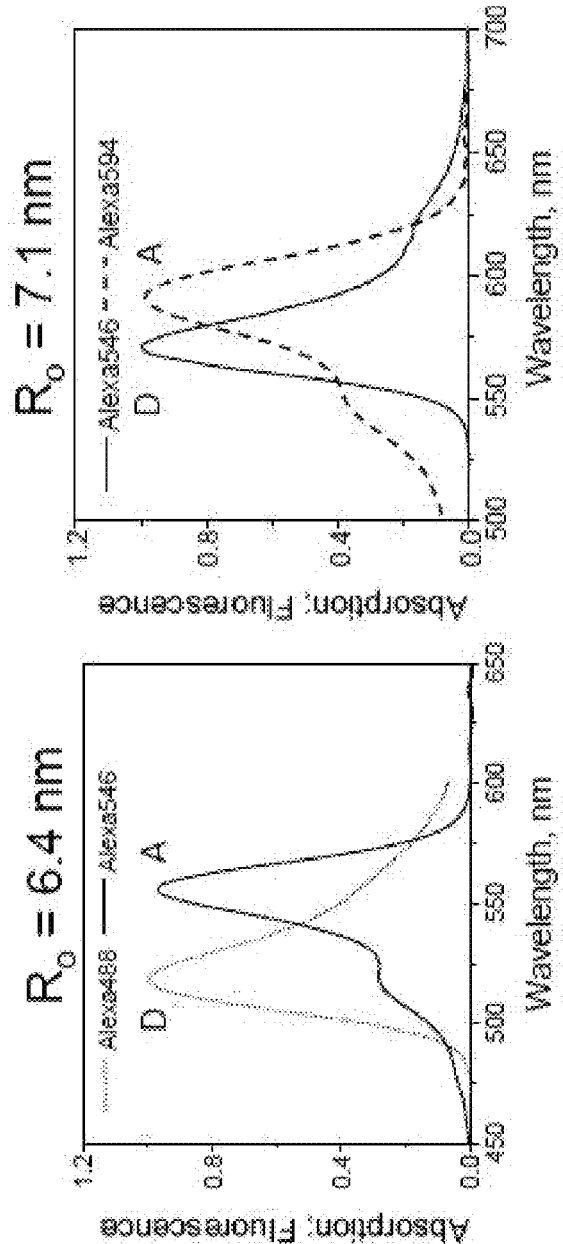
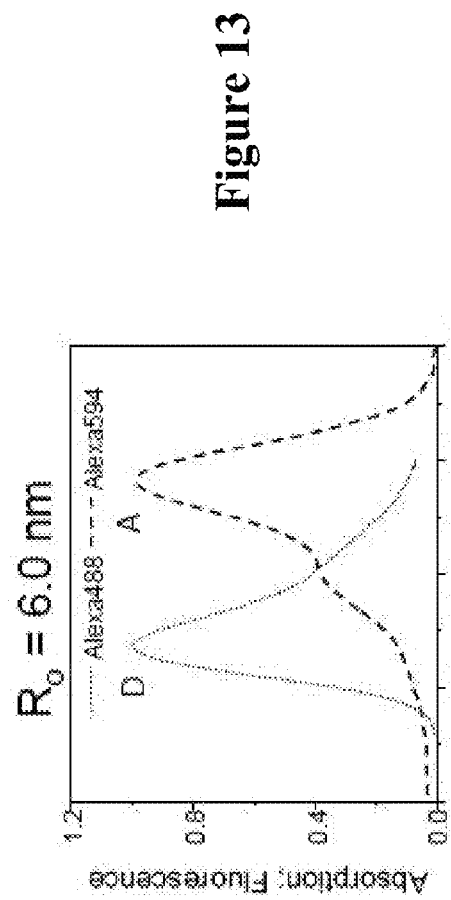
Figure 13

Anchor (A1): SH-5'-AGA GAT ATG AGC AAA AGA A
Probe:           TCT CTA TAC TCG TTT TCT T-(Alexa488) (P1)

GREEN

Anchor (A2): SH-5'-AGA GAT AAA AGA ATG AGC A
Probe:           TCT CTA TTT TCT TAC TCG T-(Alexa405) (P2)

YELLOW

Anchor (A3): SH-5'-ACT TGG AAA GGA GGC TGG A
Probe:           TGA ACC TTT CCT CCG ACC T-(Alexa546) (P3)

ORANGE

Anchor (A4): SH-5'-GAA ATG GAA CAG AGA ATA A
Probe:           CTT TAC CTT GTC TCT TAT T-(Alexa594) (P4)

RED

Anchor (A5): SH-5'-GAA ATG AGA ATA GAA CAG A
Probe:           CTT TAC TCT TAT CTT GTC T-(Alexa647) (P5)

DARK-RED

Figure 22

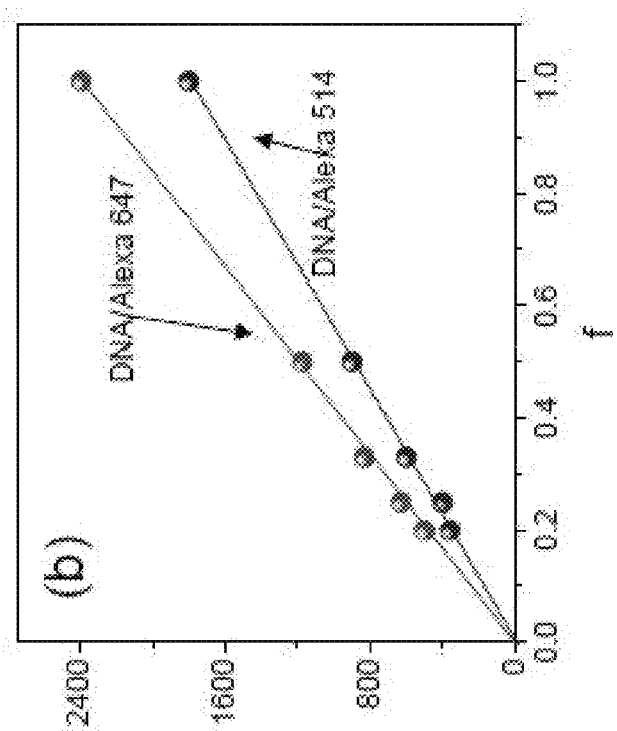
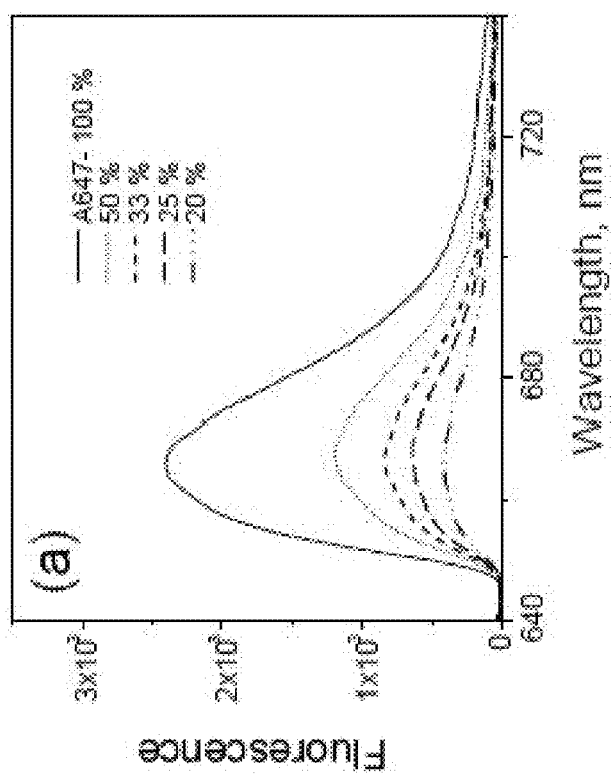
Figure 24

MULTICOLOR MICROWAVE-ACCELERATED METAL-ENHANCED FLUORESCENCE (M-MAMEF)

CROSS-REFERENCE TO RELATED APPLICATION

This is a continuation application of application U.S. patent application Ser. No. 13/420,702 filed on Mar. 15, 2012, now U.S. Pat. No. 8,735,175, which in turn claims priority to U.S. Provisional Patent Application No. 61/454,078 filed on Mar. 18, 2011, the contents of which is hereby incorporated by reference herein for all purposes.

GOVERNMENT RIGHTS IN INVENTION

This invention was made with government support under Grant Number 2U54 AIO5 7168-08, awarded by the National Institutes of Health. The government has certain rights in the invention.

BACKGROUND OF THE INVENTION

Field of Invention

The present invention relates generally to detection assays of biomolecular entities, such as nucleotides and proteins, and more specifically, to detection methods and systems that use multiple light emitting molecules having emissions in different colors for use to identify numerous different entities in the assay.

Description of Related Art

Technologies related to the recognition and detection of DNA sequences in solution is the basis of several different analytical assay approaches, which can be used for analysis of different genome DNAs and, in particular, identification of genetically diverse living organisms. The identification of living organisms, detection of different microorganism mutations and strains of pathogenic bacteria, which cause severe diseases in humans, by means of quantitative analysis of their specific DNA sequences is a challenging goal, and is the focus of much research today[1-5].

In the last few decades significant progress in DNA analysis has been achieved by the discovery and implementation of the PCR approach for the analysis of genetic material[6,7]. PCR is a hypersensitive method by which a few fragments of DNA can be duplicated into millions in a couple of hours. In other words, it represents a DNA copying machine based on an artificial increase in the amount of DNA, containing the specific target sequence. After amplification, DNA material can be easily detected by common analytical methods. Despite the obvious advantage of PCR in DNA detection this approach has some disadvantages[2,8,9], e.g. sensitivity to DNA material contaminants, misreading, quite high cost of analysis, reagents and time to fulfill experiments, and most importantly, limited utility as a general fast and easy Point-of-Care method of specific DNA sequence quantification[2,3].

Another approach for DNA quantitation is based on the direct detection of a small amount of DNA in solution, i.e. without any amplification of the DNA material. It is based on detection of the bright emission of dyes bound to nucleic acids[10-12]. Most popular chromophores for this approach are ethidium bromide, PicoGreen and Syber Green I, which bind DNA non-covalently and subsequently increase their fluorescence yield. For example, the last two chromophores increase their brightness almost 1,000 fold upon binding to double stranded DNA[10,11,13-15]. It makes them extremely sensitive to a small (<ng/ml) amounts of DNA in solution. Moreover, it recently has been shown that in the presence of silver nanoparticles, due to the Metal-Enhanced Fluorescence (MEF) effect[16], the sensitivity of PicoGreen and Syber Green I to dsDNA can be significantly further increased and become comparable to the sensitivity of the PCR technique, i.e. to be in the range of ~pg/ml[11]. The significant benefit of this approach is both the speed and the inexpensive nature of DNA quantitation. Disadvantages of this approach include a lack of DNA sequence specificity, which makes it unfeasible to employ directly in analysis of genome specific DNA samples.

A remarkable improvement of this technique[17,18] has been achieved by the combination of two approaches: microwave accelerated sequence-specific hybridization of the target DNA with anchor DNA, immobilized on a metal surface, and the Metal-Enhanced Fluorescence (MEF) effect, responsible for the immense enhancement of a DNA's fluorescent label. The MEF effect, i.e. enhancement of a fluorophore's brightness, exponentially depends on the distance between a chromophore and metallic nanoparticle, due to a short-range (0-30 nm) coupling of a chromophore's excited state electronic system with nanoparticle (NP) plasmons. As a result, only chromophores proximal to NPs increase their emission hundred's-thousand fold. Subsequently, hybridization is not only the event of a specific recognition of a target DNA, but also the creation of the MEF pair (fluorophore—NP plasmons), which enhances the fluorescence signal. Duplex annealing puts a fluorescent label on a short (~7 nm) enough leash, relative to a NP, thereby placing the label in the perfect condition for intense MEF[16,22,23]. A significant addition to this technology is microwave "heating" of the reacting system, which significantly speeds up the process of DNA hybridization[24], which is an important attractive feature of any bio-assay.

Notably the above systems are limited to locating one entity at a time, thereby increasing time and cost to separate and identify more that one target nucleotide or protein in the assay. As such, numerous assays need to be completed to identify separated targets. Thus, it would be advantageous to have systems and methods that have the ability to locate numerous targets at the same time while exhibiting increased efficiency and reaction time.

SUMMARY OF THE INVENTION

The present invention relates to the use of multiple and different light emitting molecules that, upon excitation, emit different and detectable emission signals to provide systems and methods to detect different target products in a single assay sample, wherein the different light emitting molecules are positioned an optimal distance from metallic particles thereby enhancing emissions. Preferably, the systems and methods further comprise use of either microwave or sonic energy to increase binding reactions and timing of such reactions within the assay sample.

In one aspect, the present invention relates to an assay system that provides for detecting and separating at least two target products by choosing light emitting tags, such as fluorophores or dyes, such that they possess substantially different emission spectra, preferably having emission maxima separated by greater than about 5 nm and more preferably 10 nm, more most preferably having emission maxima separated by greater than 25 nm, even more preferably separated by greater than 50 nm. When differentiation between the different light emitting tags is accomplished by visual inspection, the different emissions preferably have emission wavelengths of perceptibly different colors to enhance visual discrimination. When it is desirable to differentiate between the different fluorophores or dyes using instrumental methods, a variety of filters and diffraction gratings allow the respective emission maxima to be independently detected.

The present invention may be used to separate at least two and up to ten or more different targets in a single assay system.

In another aspect, the present invention relates to a method of decreasing the detection time of a metal-enhanced fluorescence assay used for detection of multiple and different target nucleotides, including DNA and RNA, the method comprising:
  a. applying a multiplicity of metallic particles to a substrate surface used in an assay system;
  b. connecting at least two different capture nucleotides to the metallic particles, wherein each of the capture nucleotides has binding affinity for a different target nucleotide;
  c. introducing a solution suspected of including the different target nucleotides;
  d. introducing at least two different detector nucleotides, wherein each of the detector nucleotides has binding affinity for a different target nucleotide and wherein each of the detector nucleotides includes a different fluorescence molecule;
  e. applying microwave or sonic energy to the assay system for a time period sufficient to increase binding reactions between the capture nucleotides and/or detector nucleotides with target nucleotides reactions and reduce background non-specific biological absorption;
  f. applying electromagnetic energy at a frequency to excite the fluorescence molecules; and
  g. measuring any fluorescence signals.

In all embodiments, the metallic material used for fabricating the metallic particles may include, but is not limited, to silver, gold, copper, zinc, nickel, iron, palladium, aluminum, indium, nickel, platinum, mixtures thereof, and any metal that exhibits plasmonic emissions. In the alternative, the metallic structures may be fabricated from a combination of at least two metals selected from the group consisting of Silver, Gold, Aluminium, Zinc, Rhodium, Copper, Nickel, Palladium, Indium, Tin, Iron, Tungsten, Platinum, and Germanium. The mixed metals may be either a homogeneous mixture or hetergeneous mixture, or in the alternative may be layered. Yet further advantages include the ability of some sensitive metals to be protected from other metals by using metals with different chemical properties. For example, gold capped silver could be used to enhance fluorescence, but also protect the silver from long term oxidation.

The metallic particles may take the form of metallic islands, colloids, or nanostructures of any geometric shape, such as spherical, triangular, elliptical, rod shape, hexagonal or multifaceted. The metallic material may take the form of porous matrix, metallic particles impregnated within a glass or polymeric surface and/or on a metallic surface in a patterned shape.

The patterned shape includes metallic particles having a patterned shape with at least one apex wherein the shape includes but is not limited to a triangle, square, rectangle, trapezoid, polygon, elliptical, oblong or combinations thereof. Further, emissions and reactivity can be enhanced by placement of metallic structures having a shape with an apex area and positioning such apex areas adjacent to each other and creating a reactive zone therebetween. The reactive zone therebetween is prepared for placement of the immobilized capture molecule complementary to a target molecule. The metallic structures when fabricated into geometric shapes comprising an apex area for forming a reactive zone can be positioned on assay system with multiple wells wherein the reactive zone includes the wells and exposure to low-intensity ultrasound or microwave energy increases the reactivity and shortens the completion time of the detection assay.

It is envisioned that the apex area includes not only pointed regions but regions with rounded edges such as found in an oblong or elliptical shape. The apex areas are preferably arranged so that one apex area is opposite from another apex area and aligned to form a reactive zone to be positioned therebetween. The distances between the apex areas may range from 0.01 mm to 5 mm, more preferably from 2 mm to about 3 mm. The thickness of the metallic geometric shaped forms ranges from 10 nm to about 1000 nm, and more preferably from about 45 nm to about 250 nm.

The metallic structures may include a combination of metals, deposited in any order on a substrate, for example silver, gold, or gold and then a silver layer. Additionally a layer of a dielectric material may be included. Further, the metallic structures can be in a nanoball shape with an internal metal core, a silica or oxide layer and another top metallic layer wherein the core metal is different from the outer layer. In the alternative, both the core and outer layers may be fabricated of a mixed-metal combination.

The oxide layer may include at least one metal selected from the group consisting of Al, Ca, Ti, Fe, Cu, Zn, Y, Zr, Nb, Mo, In, Si, Sn, Sb, Ta, W, Pb, Bi and Ce and having a valence of from 2 to 6. The form of the oxide of such a metal may, for example, be $Al_2O_3$, $SiO_2$, $TiO_2$, $Fe_2O_3$, $CuO$, $ZnO$, $Y_2O_3$, $ZrO_2$, $Nb_2O_5$, $MoO_3$, $In_2O_3$, $SnO_2$, $Sb_2O_5$, $Ta_2O_5$, $WO_3$, $PbO$ or $Bi_2O_3$. These metal oxides may be used alone or in combination with other types of coatings. Preferably, the oxide is a silicon oxide, more preferably, $SiO_2$. The vapor deposition of $SiO_2$ is a well established technique for the controlled deposition of a variety of substrates. For example, an Edwards Vapor deposition module allows the deposition of an inert coating of $SiO_2$.

The substrate positioned beneath the metallic structures may include glass, quartz, plastics (such as on the bottom of HTS plates, polystyrene, polycarbonate), semiconductors, paper, cellulose, cotton, nylon, silk, sapphire, diamond, ruby, dielectric materials as described above, etc. Notably, the substrate may be transparent or non-transparent thereby allowing for excitation energy to be delivered from multiple angles, that being, at the top, side or bottom of the substrate to provide excitation energy to the excitable molecules, such as fluorophores.

In yet another aspect, the present invention provides a method for lysing pathogen cells and detecting different targeted DNAs from the same target pathogen or different target pathogens in a sample, the method comprising:
  a. providing a system comprising:
    i. immobilized metallic nanostructures positioned on a surface substrate, wherein the immobilized metallic structures have attached thereto at least one capture nucleotide, wherein the capture nucleotide has binding affinity for known DNA sequences from the same target pathogen or different target pathogens in a sample; and
    ii. free capture DNA sequence probes that are complementary to the known DNA sequences, wherein the free capture DNA sequences are different and in an amount sufficient to bind to different sequences of the same target pathogen or to bind to sequences of different target pathogens, and wherein the free capture DNA sequence probes have attached thereto an excitable energy emitting molecule, wherein the free capture DNA sequence probes comprise excitable energy emitting molecules that are specific for the different target pathogens or different sequences of the same target pathogen suspected of being in the sample, wherein the excitable energy emitting molecules emit energy in a detectably range such as in the UV to IR range;

b. contacting the sample with the immobilized capture DNA sequence probes, wherein the different DNA sequences of the target pathogen binds to the corresponding immobilized capture DNA sequence probes or the DNA sequences of the different target pathogens binds to the corresponding immobilized capture DNA sequence probes;

c. contacting the bound DNA sequences with the free capture DNA sequence probes, wherein binding of free capture DNA sequence probes to the DNA sequences causes the excitable energy emitting molecule to be positioned a sufficient distance from the immobilized metallic material to enhance energy emission; and d. irradiating the system with electromagnetic energy in a range from UV to IR to induce emissions by the excitable energy emitting molecule positioned a predetermined distance from the metallic material, wherein the irradiating can be conducted before, during or after the applying of either microwave or ultrasound energy.

During the assay process the method may further comprise applying to the system microwave or sonic energy in an amount sufficient to increase the speed of the binding reactions; and Notably the above system is described using energy emitting molecules and any molecule that is capable of emitting a detectable signal upon excitation by electromagnetic energy is included, such as, fluorophores, chromophores, luminophores, and carbon nanodots. Further bioluminescent molecules that emit a detectable signal in response to a chemical reaction are also included within the scope of the present invention. Still further, the compound capable of fluorescing may be an intrinsic fluorophore or a compound attached to an extrinsic fluorophore.

A further aspect of the present invention, relates to a kit for detecting different target molecules in a sample, the kit comprising a. a container comprising a layer of immobilized metal particles deposited on a substrate fabricated of a polymeric or quartz material, wherein at least two different immobilized probes are connected to the metal particles and wherein each of the immobilized probe has affinity for different target molecule;

b. at least two different excitable molecules that emit light upon excitation, wherein each has affinity for a different target molecule, wherein the binding of the target molecule to the immobilized probe and an excitable molecule having affinity for the target molecules causes the excitable molecule to be positioned a sufficient distance from the immobilized metal particles to enhance emission once the excitable molecule is excited with electromagnetic energy in a range from UV to IR; and c. a source of microwave or ultrasonic energy to increase binding reactions within the system and a source of electromagnetic energy to excite the excitable molecules.

The above system can be used in a 96-well or 384-well high through put screening plates ore on a custom made high density array chips.

Notably the excitable molecule is selected from the group of an intrinsic fluorophore, extrinsic fluorophore, fluorescent dye, chromophores, phosphorus compounds, carbon compounds or allotropes, carbon nanotubes, carbon nanodots, silicon luminescent compounds, semiconductor quantum dot, multiatom gold or silver atom luminescent clusters and luminophores.

The emission enhancement may be observed when the excitable molecules are positioned from about 5 nm to about 200 nm to metal surfaces. Preferable distances are about 5 nm to about 30 nm, and more preferably, 5 nm to about 20 nm to metal surfaces.

The present invention relates to a method of detection using plasmonic emissions from metallic surfaces caused by fluorescence, chemiluminescence or bioluminescence based reactions. These plasmonic emissions emitted from metallic surface plasmons are generated either with an external excitation or without such external excitation due to chemically induced electronically excited states. Further, mixed metal structures may be used to enhance spectral regions were the metals themselves do not have plasmon resonance, due to the creation of new mixed metal plasmon bands.

In yet another aspect, the present invention relates to a method of metal-enhanced emission sensing, comprising:

a. providing a substrate surface having immobilized thereon metallic particles;

b. introducing a solution containing a multiplicity of receptor biomolecules for disposing on or near the metallic particles;

c. introducing ligands, wherein each ligand has binding affinity for binding with one of the receptor biomolecules, wherein the ligands are different and bind with the corresponding receptor biomolecules having affinity therewith, wherein an excitable molecule is attached to each ligand and provides an indication of the binding of the ligand to the specific receptor biomolecule; and d. measuring the different excitable signals to determine different receptor biomolecules in the solution.

Notably the biomolecules may include proteins or peptides in solution and the proteins or peptides can be positioned on or adjacent to the metallic particles. The ligands which include the excitable molecules, may be another amino acids chain (peptide) having binding affinity for the receptor. Thus a solution suspected of carrying certain proteins may be identified by selected amino acid residues (peptides) that have binding affinity. Numerous proteins can be determined in a single sample by selected peptides that bind to the proteins. Each peptide includes a different fluorophore that emits a different signal. As such, depending on the number of different fluorophores and their separable signals, numerous proteins can be isolated within a single sample.

Notably, the solutions used for carrying a target compound may include the addition of solution media which helps to increase the photostability (intensity Vs Time) of the multicolor assays. Typical solution additives may include, ascorbic acid (Vitamin C), Trolox, DABCO, p-phenylenediamine and n-propyl gallateetc, all electron donating and scavenging compounds, $NO_2$ and NO reactive dyes, singlet oxygen absorbing and superoxide anion radical absorbing compounds.

In another aspect, the present invention relates to a system for measuring excitable signals relating to the determination of different desired molecules in a testing sample, the system comprising:

a multiplicity of metallic particles positioned on a surface substrate, wherein the metalized particles are fabricated from the same or different metals;

at least one connector molecule attached to the metallic particles or near the metallized particles for binding or capture of desired molecules in a testing sample, wherein the connector molecule is specific for one of the desired molecules in the testing sample;

at least one detector molecule having an affinity for and specific for one of the desired molecule, wherein the detector molecule comprises a fluorescence label and desired molecule in the test sample corresponds to a different fluorescence label;

an electromagnetic energy source for exciting the fluorescence labels; a source of sonic or microwave energy to increase reaction rates within the system; and a measuring device to measure emissions.

The methods described above may be used in multiple detecting systems, including but not limited to, immunoassays, hybridization assays, resonance energy transfer assays, polarization/anisotropy based assays, chemiluminescence based assays, luminescence based assays, and enzyme-linked immunosorbent assays.

Other aspects and advantages of the invention will be more fully apparent from the ensuing disclosure and appended claims.

BRIEF DESCRIPTION OF THE FIGURES

FIG. 13 shows the fluorescence and absorption spectra for different D-A pairs and their Förster distances ($R_o$ values have been quoted from the Molecular Probes Handbook).

Figure 16:
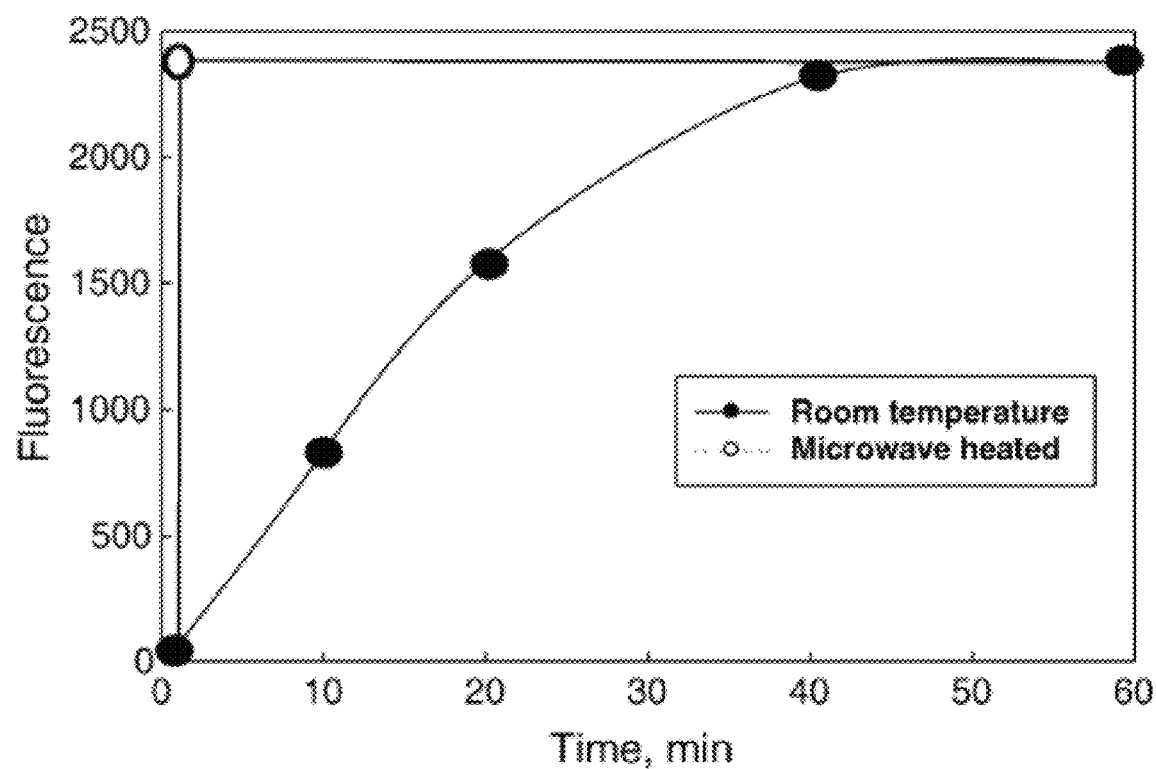

FIG. 16 shows the room temperature real-time hybridization kinetics for Alexa 594 nm and microwave acceleration for 30 s. The "Rapid Catch and Signal" assay is complete in less than 30 s.

Figure 17:
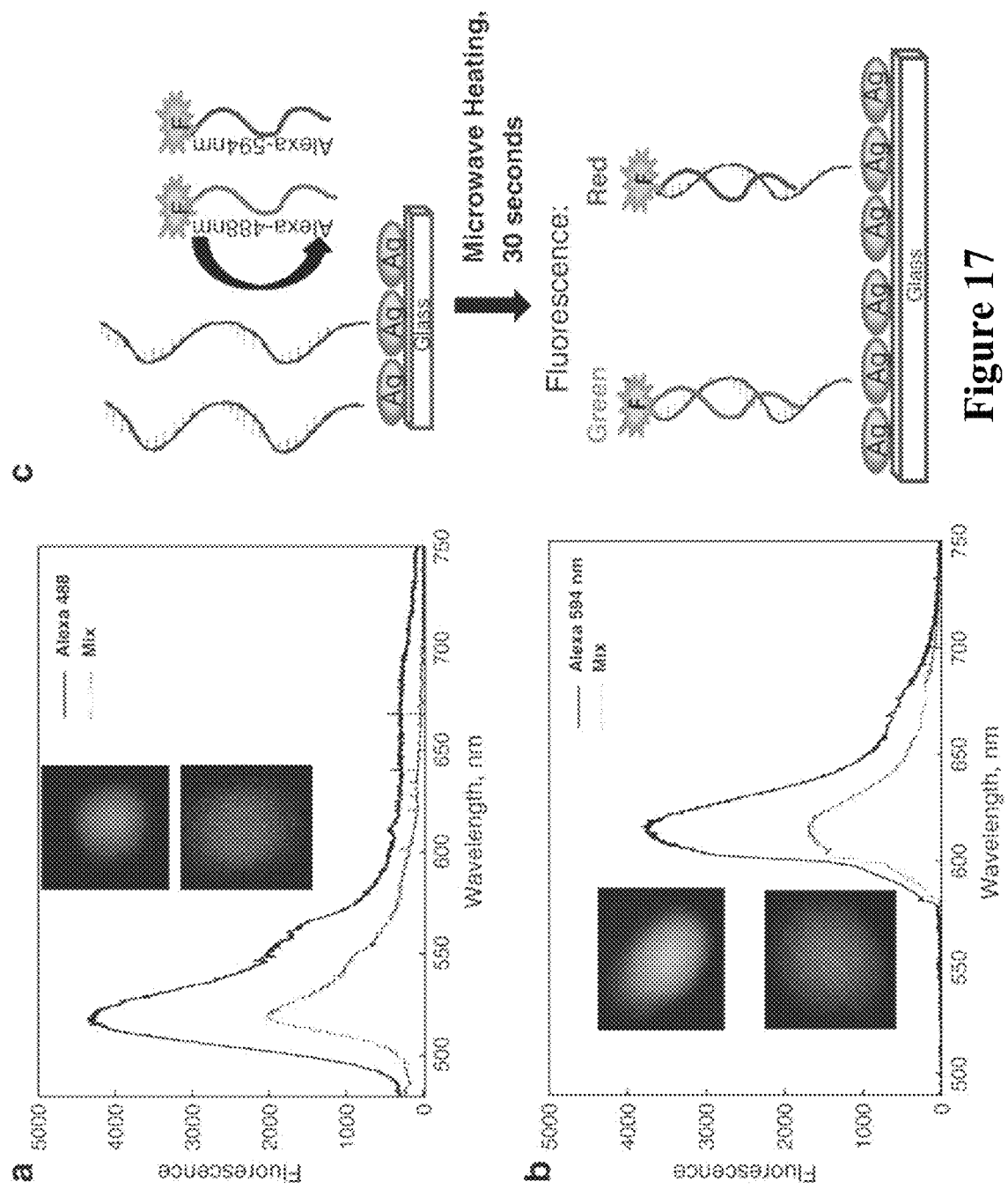

FIG. 17 shows (a) Emission spectra of Alexa 488 and a 1/1 mixture of both Alexa 488 and 594 dyes attached to a DNA/SiF film. Excitation was undertaken with a 473 nm laser line. (b) Emission spectra of Alexa 594 and a 1/1 mixture of both Alexa 488 and 594 dyes attached to a DNA/SiF film. Excited with a 594 nm laser line. (c) General scheme of 2-color DNA assay.

Figure 18:
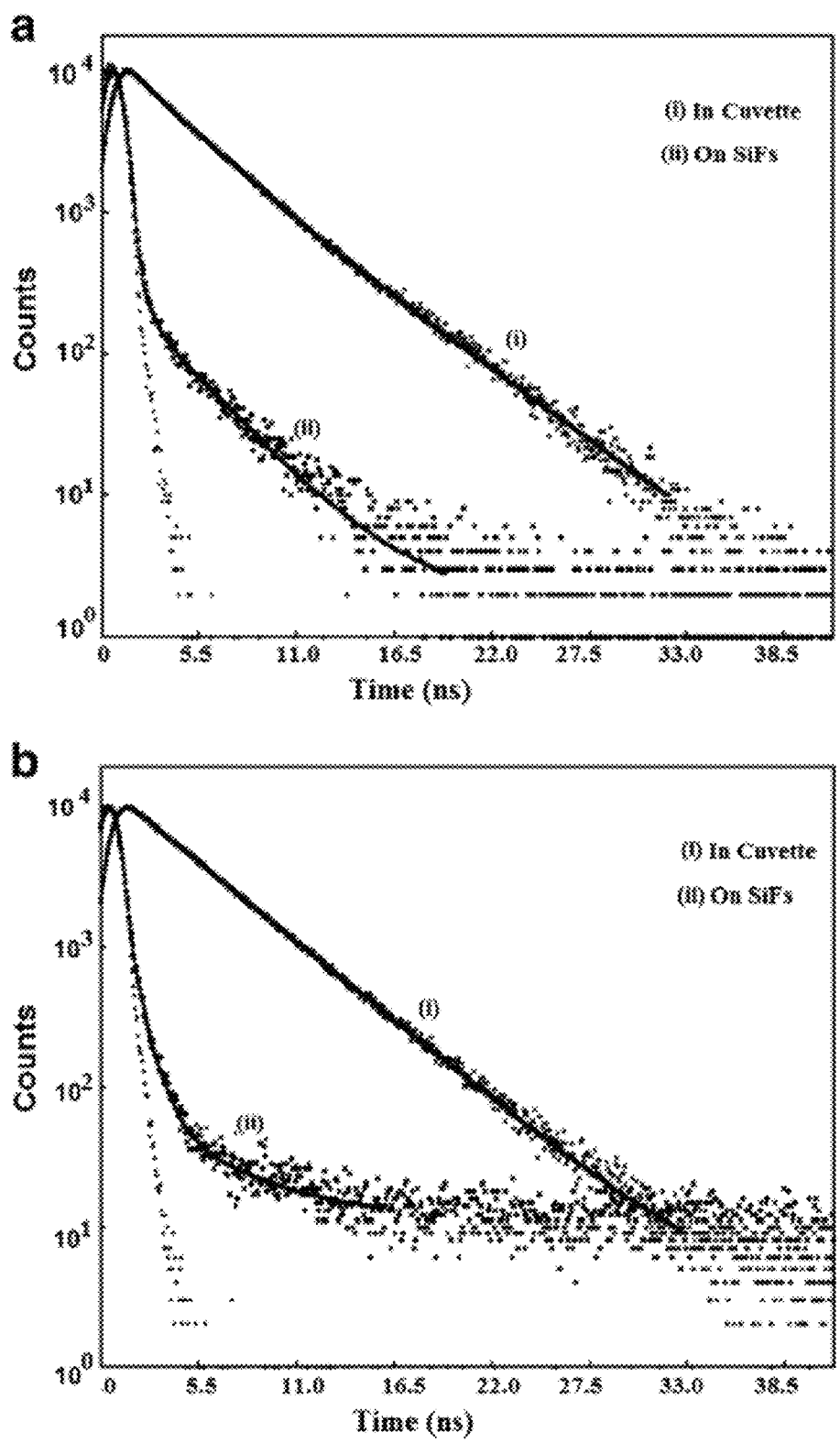

FIG. 18 shows the intensity decay profile of (a) Alexa 488 and (b) Alexa 594 on glass, a SiFs sandwich and in solution (cuvette) λex=467 nm.

Figure 19:
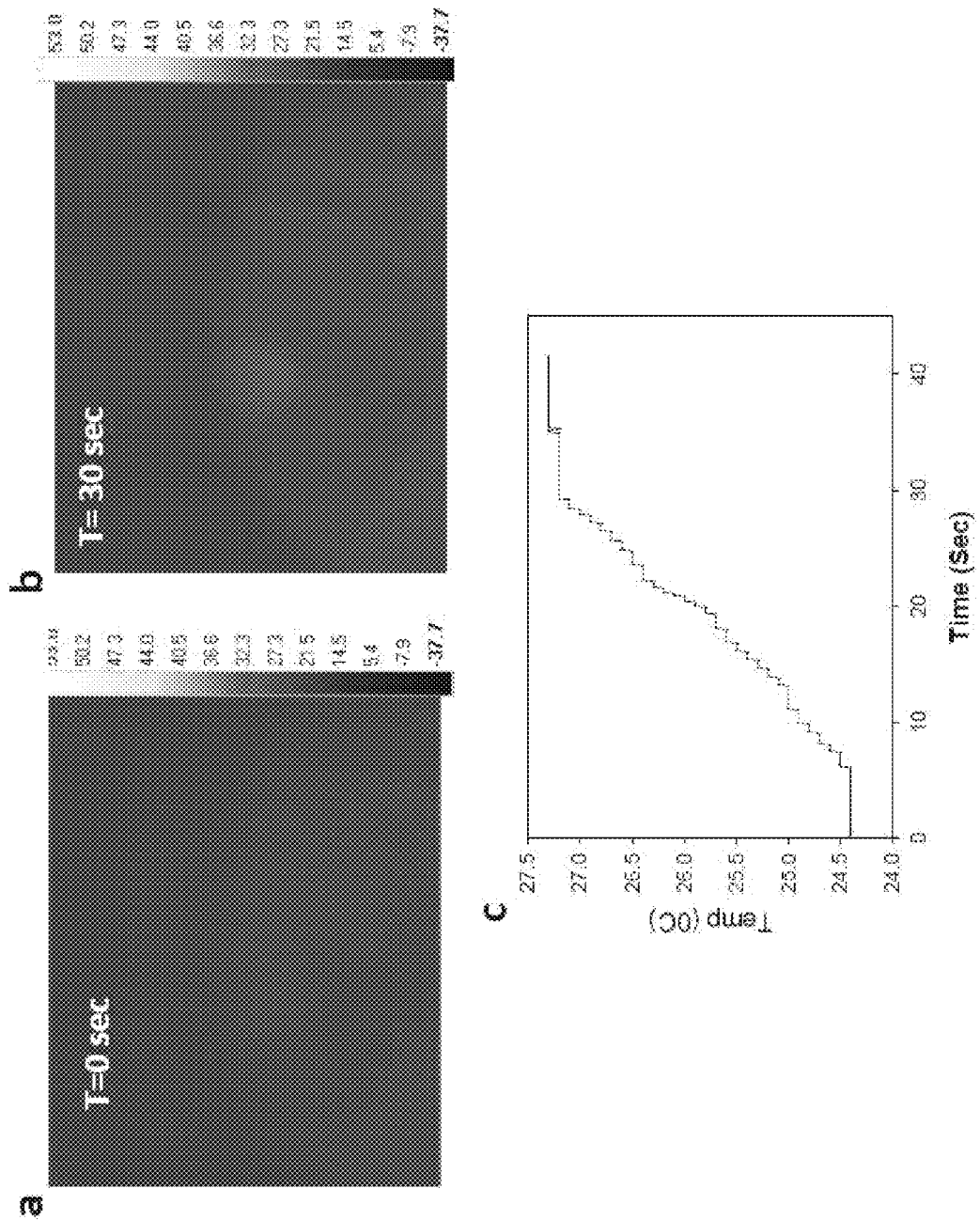

FIG. 19 shows the thermal images of the sample (DNAs labeled with Alexa488 and Alexa594 attached to SiFs) before (a) and after (b) microwave heating for 30 seconds, plot (c) shows the real-time heating of the well.

Figure 20:
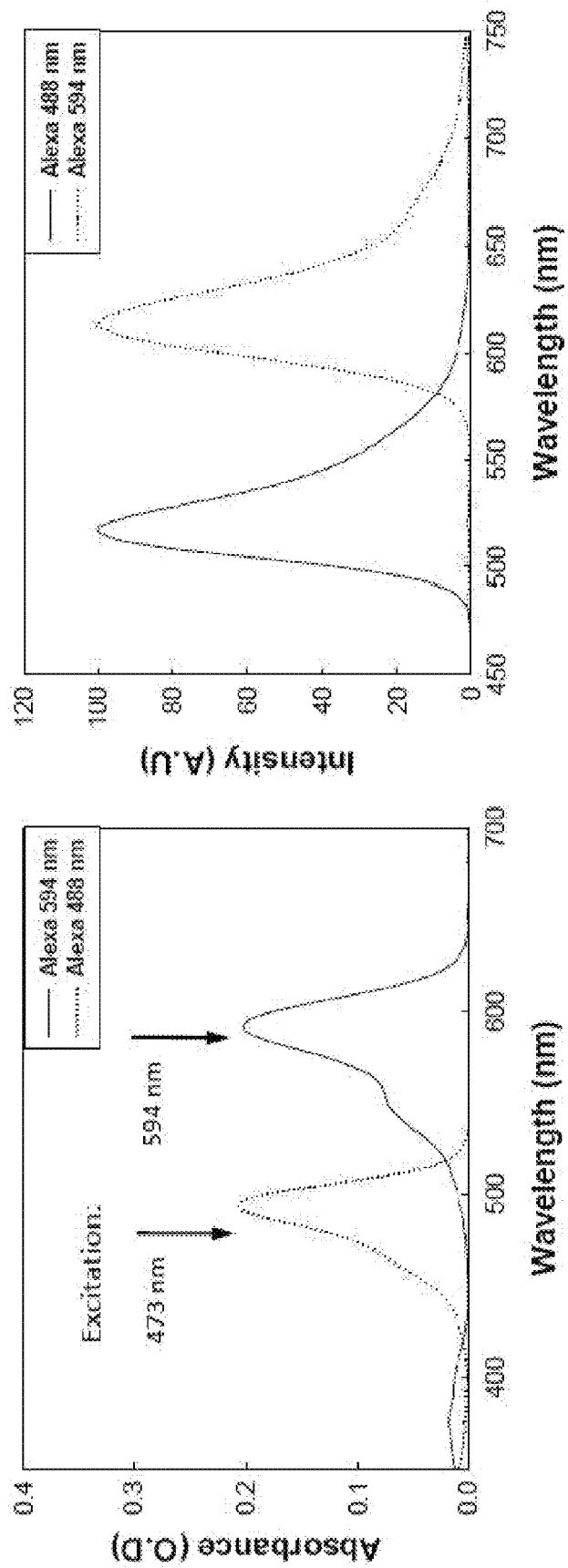

FIG. 20 shows the absorbtion (left) and fluorescence (right) spectra of Alexa 488 and Alexa 594 measured at 1 µM concentration in TE buffer. pH 7.4.

Figure 21:
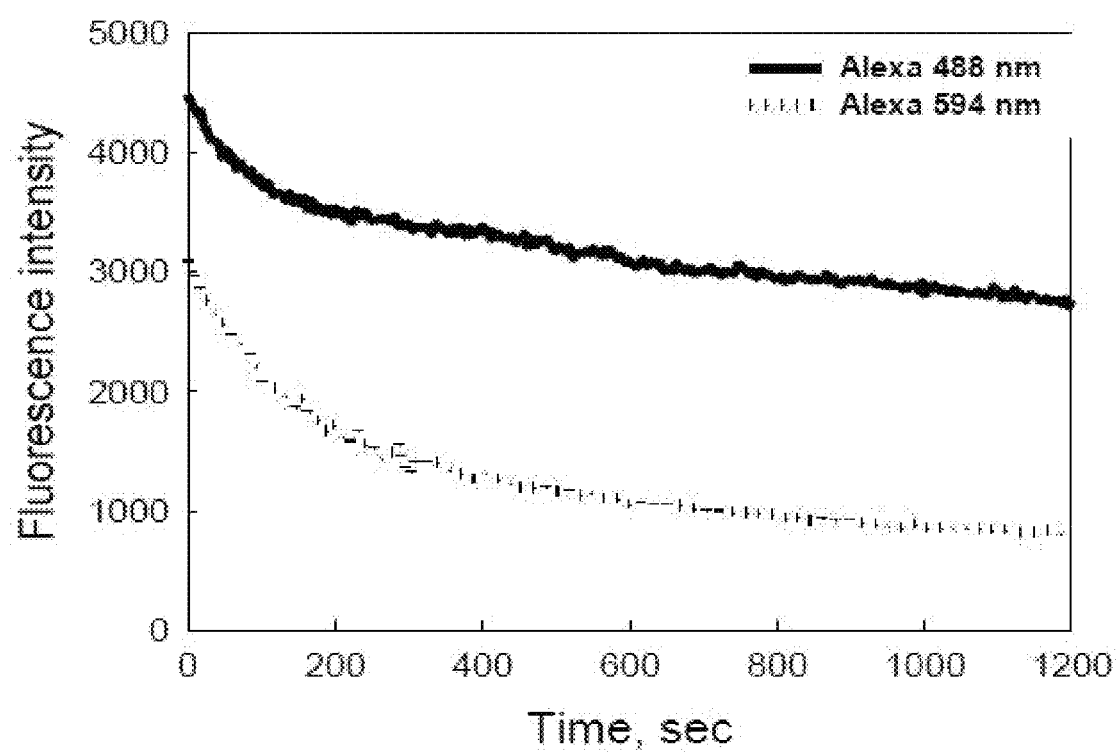

FIG. 21 shows (a) Photostability (Intensity vs time) of Alexa 488 and Alexa 594 dyes attached to a DNA/SiFs surface. Fluorescence intensity was measured upon continuous irradiation of the dye/DNA/SiF surface with 20 mW CW laser lines: 473 nm (for Alexa 488) and 594 nm (for Alexa 594).

FIG. 22 shows the sequences of the Anchor and Probe ssDNAs. The DNA sequences used in this study are fragments of Chinese hamster ovary (CHO) Alu sequence. (A1 (AGA GAT ATG AGC AAA AGA A) (SEQ ID NO: 1)); (P1 (TCT CTA TACT CG TTT TCT T) (SEQ ID NO: 2)); (A2 (AGA GAT AAA AGA ATG AGC A) (SEQ ID NO: 7)); (P2 (TCT CTA TTT TCT TACT CG T) SEQ ID NO: 8)); (A3 (ACT TGG AAA GGA GGC TGG A) (SEQ ID NO: 3)); (P3 (TGA ACC TTT CCT CCG ACC T) (SEQ ID NO: 4)); (A4 (GAA ATG GAA CA GAGA ATA A) (SEQ ID NO: 5)); (P4 (CTT TAC CTT GTC TCT TAT T) (SEQ ID NO: 6)); (A5 (GAA ATG AGA ATA GAA CAG A) (SEQ ID NO: 9)); (P5 (CTT TAC TCT TAT CTT GTC T) (SEQ ID NO: 10))

Figure 23:
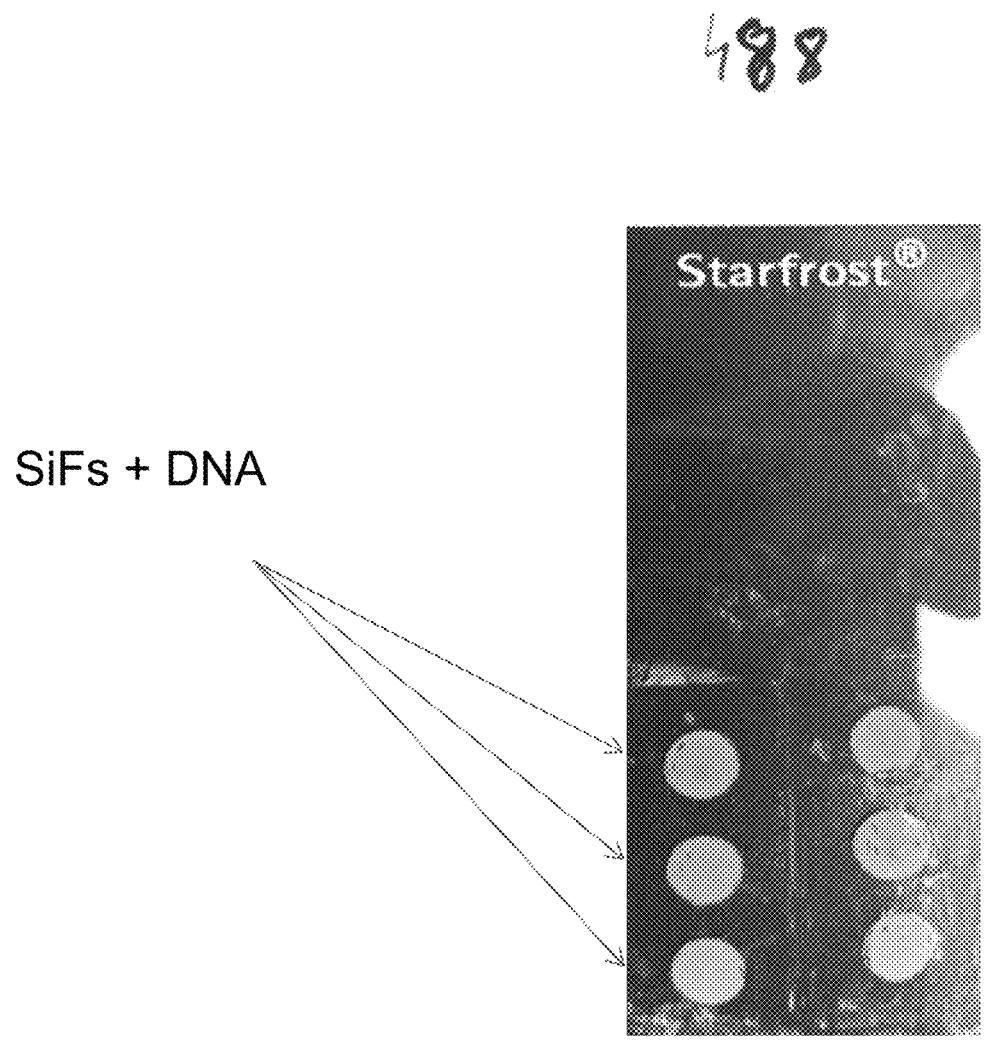

FIG. 23 shows real-color photograph of the silver surface (SiFs) coated with attached DNA scaffold. Incubation of DNA solution on SiFs was in rubber wells attached to the slide surface. After incubation rubber wells were removed from the slide.

FIG. 24 shows (a) Fluorescence spectra of DNA/Alexa 647 recorded for the different loading ratio of DNA/Alexa-647 to the total loaded onto SiFs DNA. (b) The dependences of DAN/Alexa647 and DNA/Alexa-514 fluorescence upon the fraction of these labeled DNA on SiFs surface. Attachment of different types (sequences) of DNA to SiFs is independent and proportional to their relative concentration in the loading solution.

Figure 25:
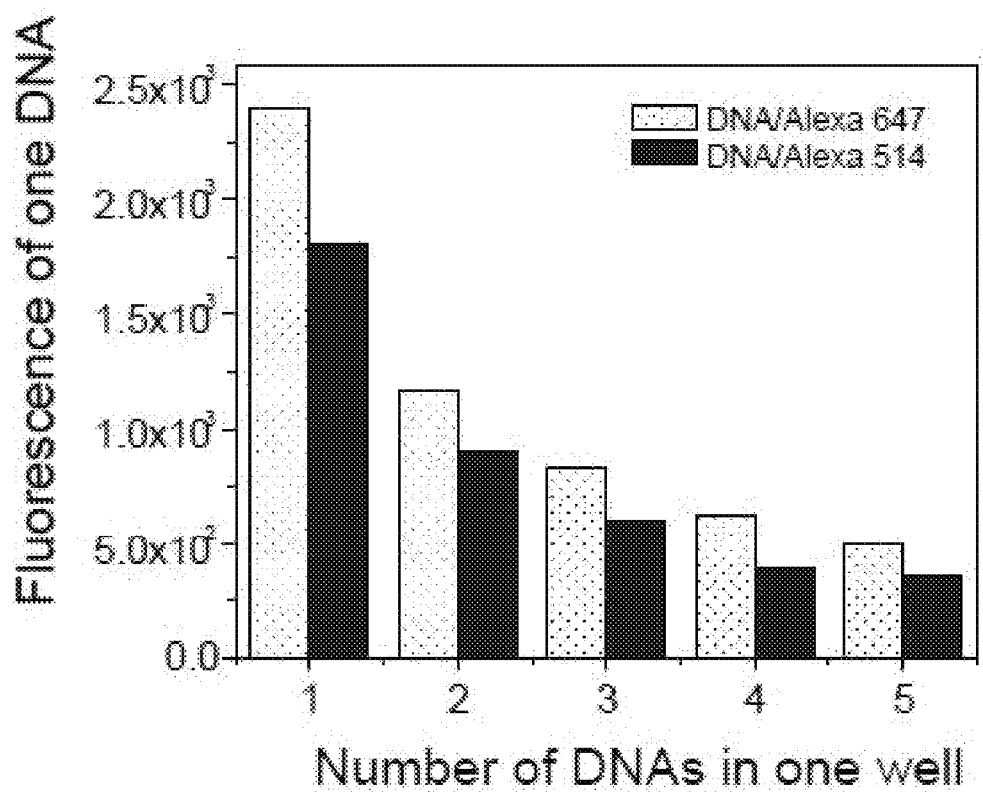

FIG. 25 shows the change in fluorescence signal strength upon the number of DNA molecules in one well. The dependence was measured for two different specific DNA markers labeled with different chromophores (Alexa-647 and -514).

Figure 26:
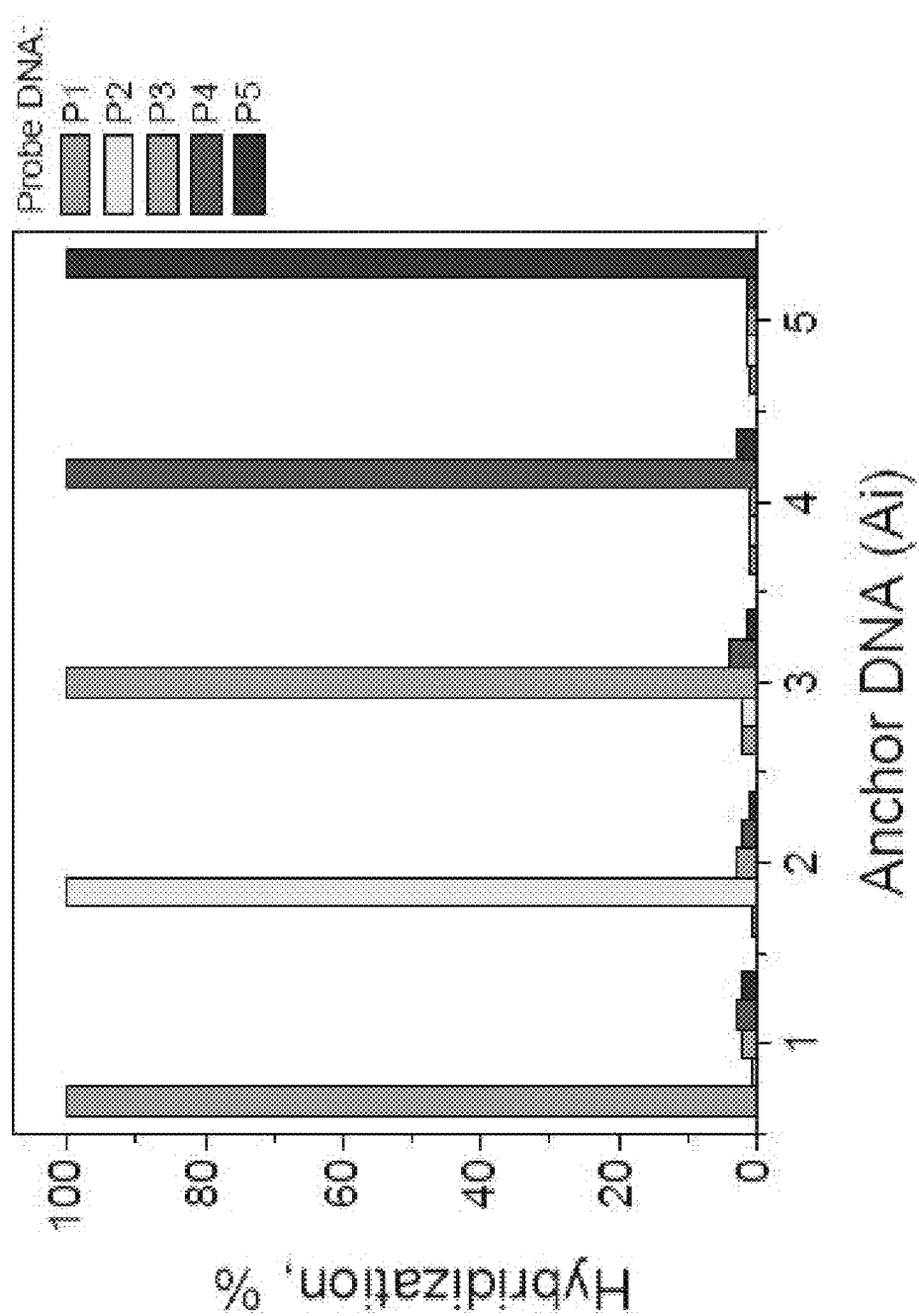

FIG. 26 shows the cross-selectivity of the DNA-DNA molecular recognition (hybridization). Hybridization of a Probe DNA with the Anchor DNA scaffold on SiF was accelerated by microwave irradiation (30 sec). Microwave acceleration induces highly specific hybridization of the probe-DNA with the complementary anchor-DNA attached to SiFs. Cross selectivity is >98%.

Figure 27:
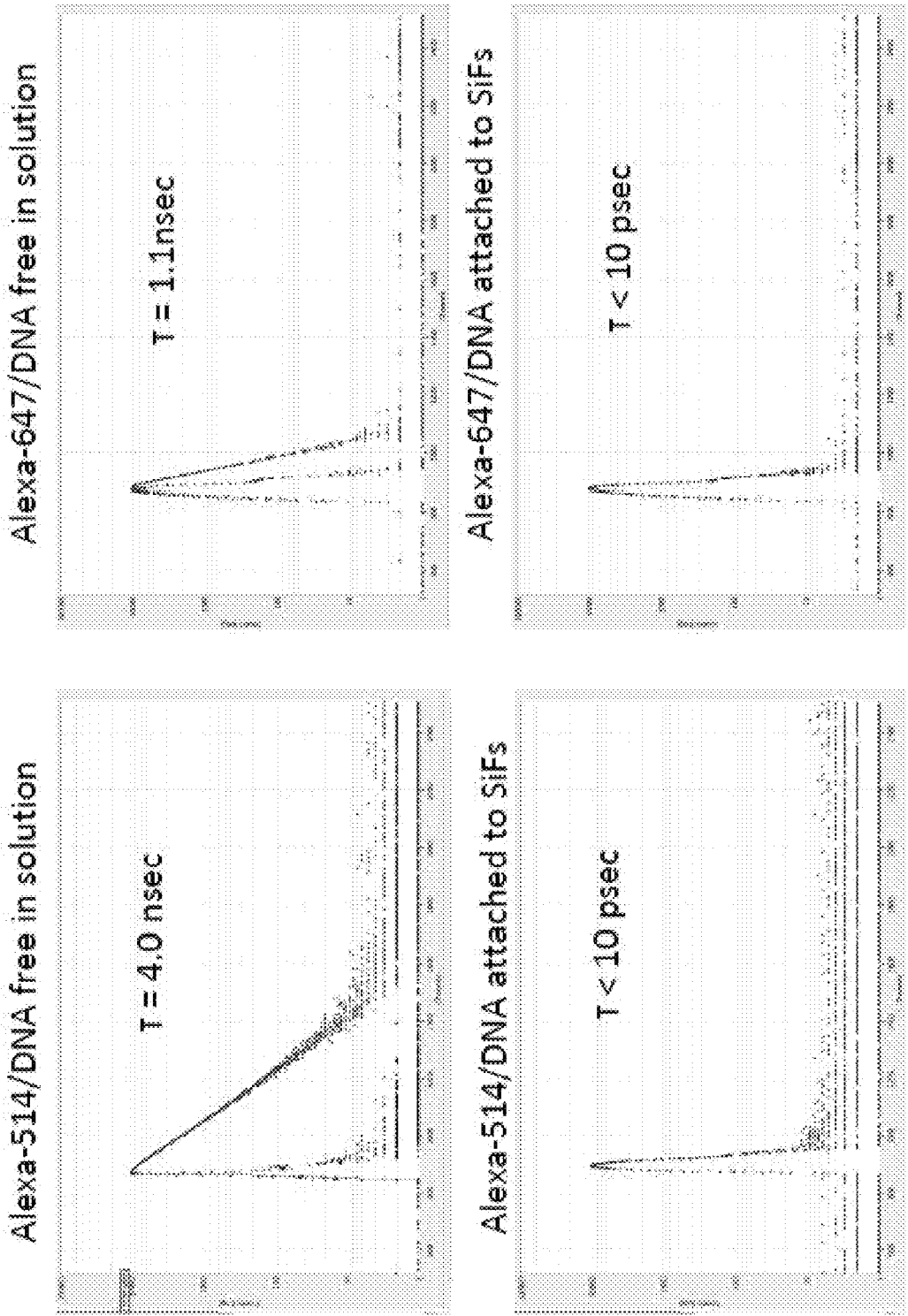

FIG. 27 shows the attachment of the Alexa/DNAs to SiFs dramatically decreases excited state lifetime ($\tau$) of the dyes and, consequently, increases their photostability. Time-resolved fluorescence decay profiles were measured by time-domain approach. For the Alexa chromophores attachment of Dye/DNA to SiFs changes their lifetime from 1-4 nsec to <10 psec, i.e. more than 100-fold.

Figure 28:
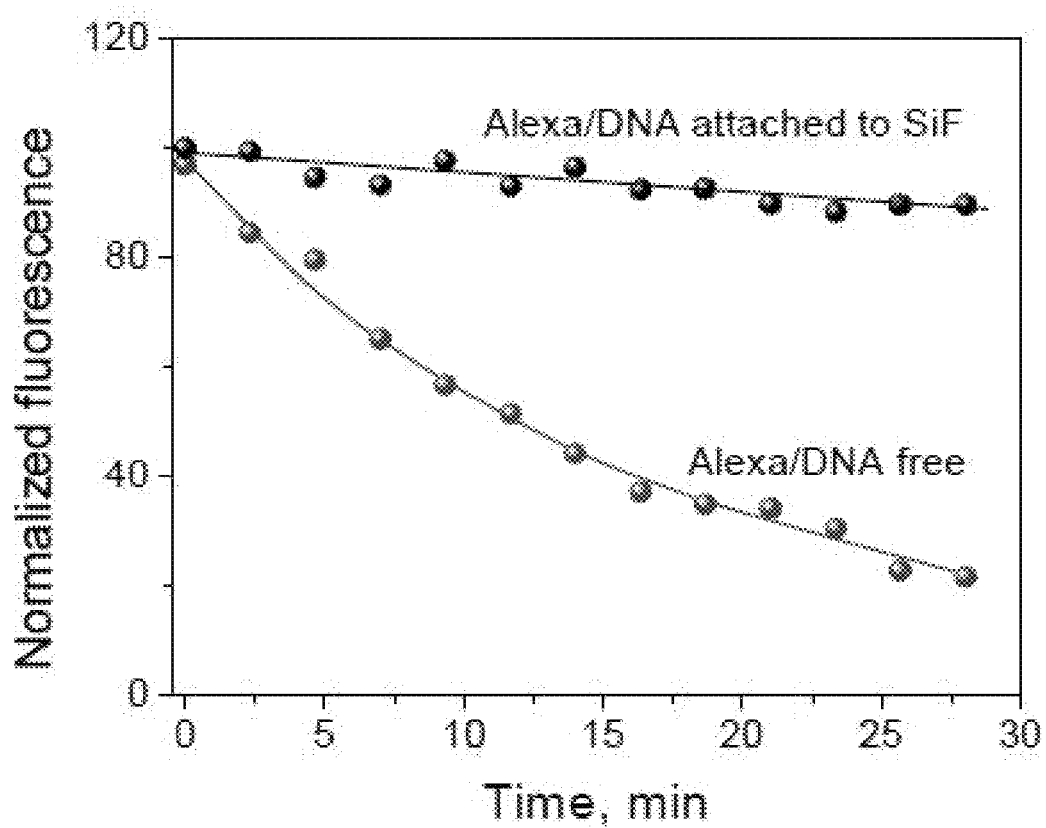

FIG. 28 shows the photobleaching profiles of Alexa546-dsDNA attached to SiFs and free Alexa546-ssDNA on glass. Laser power—5 mW. Excitation—532 nm. Photostability of the DNA labels (Alexa dyes) attached to SiFs is greater than that of free dyes in solution.

Figure 29:
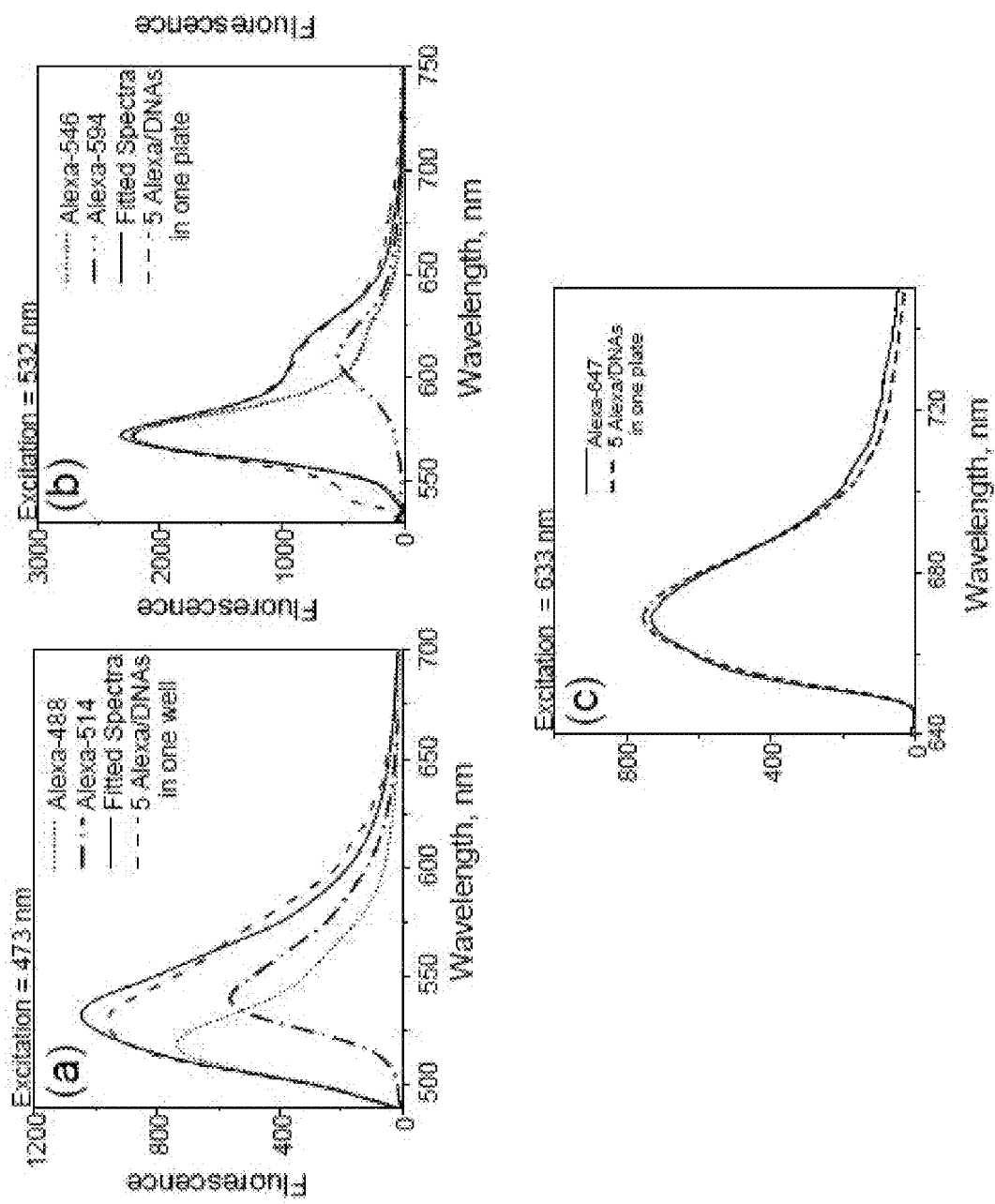

FIG. 29 shows the fluorescence from one wells containing five different labeled DNAs in equimolar ratio. (a)-(c) Fluorescence spectra of five Alexa-DNAs excited by three different lasers ((a) 473 nm, (b) 532 nm and (c) 633 nm). Recorded spectra were deconvoluted on their components. The best fitting curves (spectra) and their individual components are show in (a)-(c) graphs.

Figure 30:
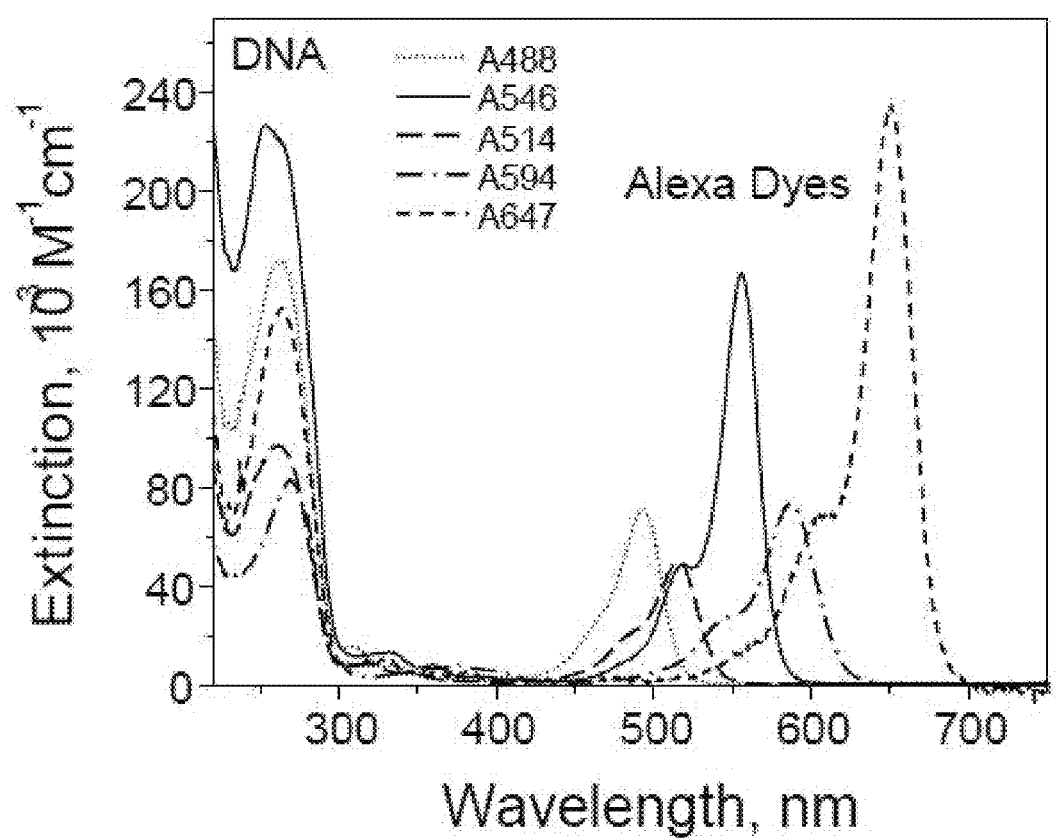

FIG. 30 shows the molar extinction spectra for the set of chromophores used in the 5-color DNA assay.

Figure 31:
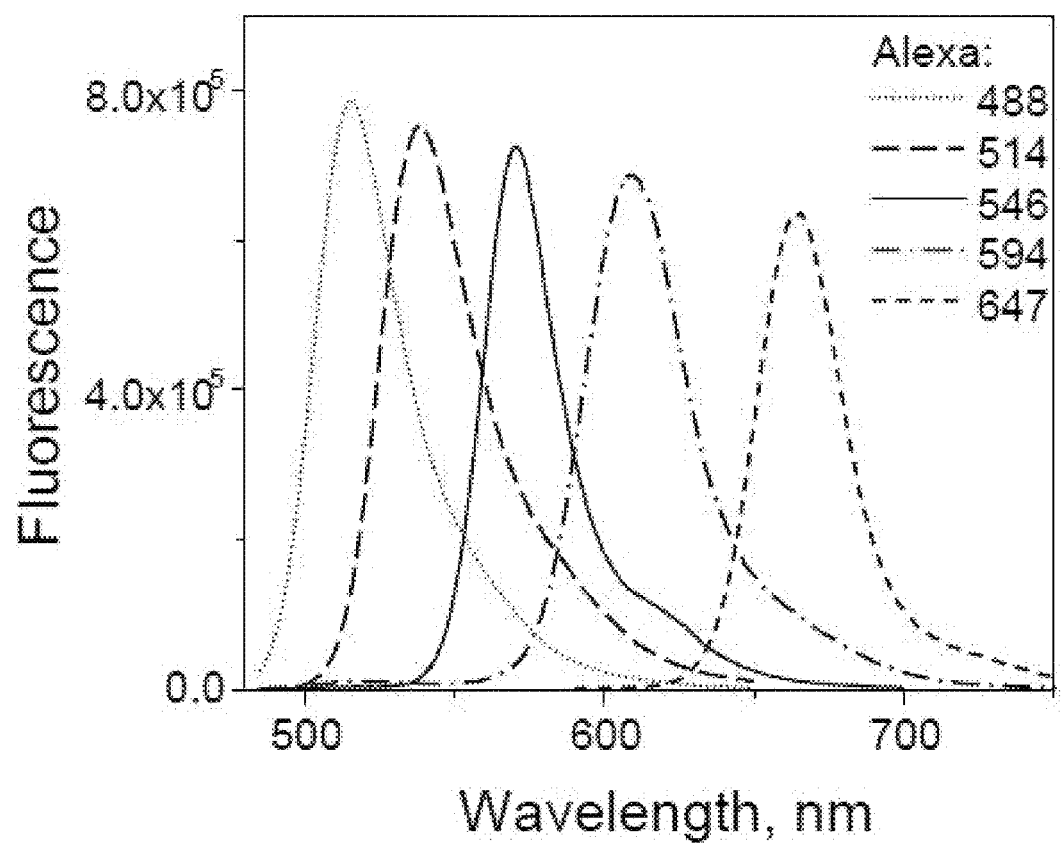

FIG. 31 shows the fluorescence spectra of the chromophores used in the 5-Color DNA Assays.

Figure 32:
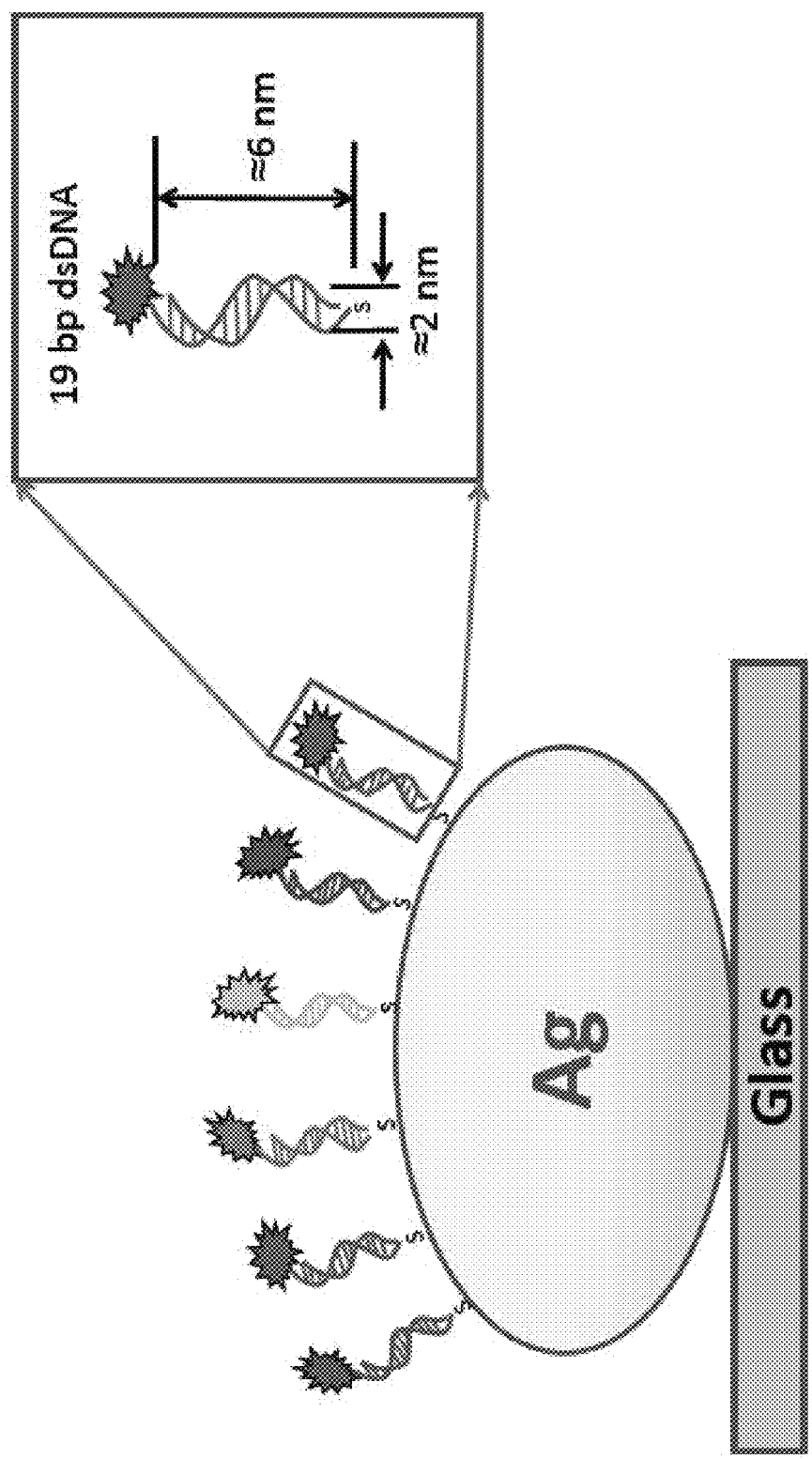

FIG. 32 shows that five different anchor DNAs are attached to SiFs, each of them recognizes and hybridizes with their complementary respective probe-DNA.

Figure 33:
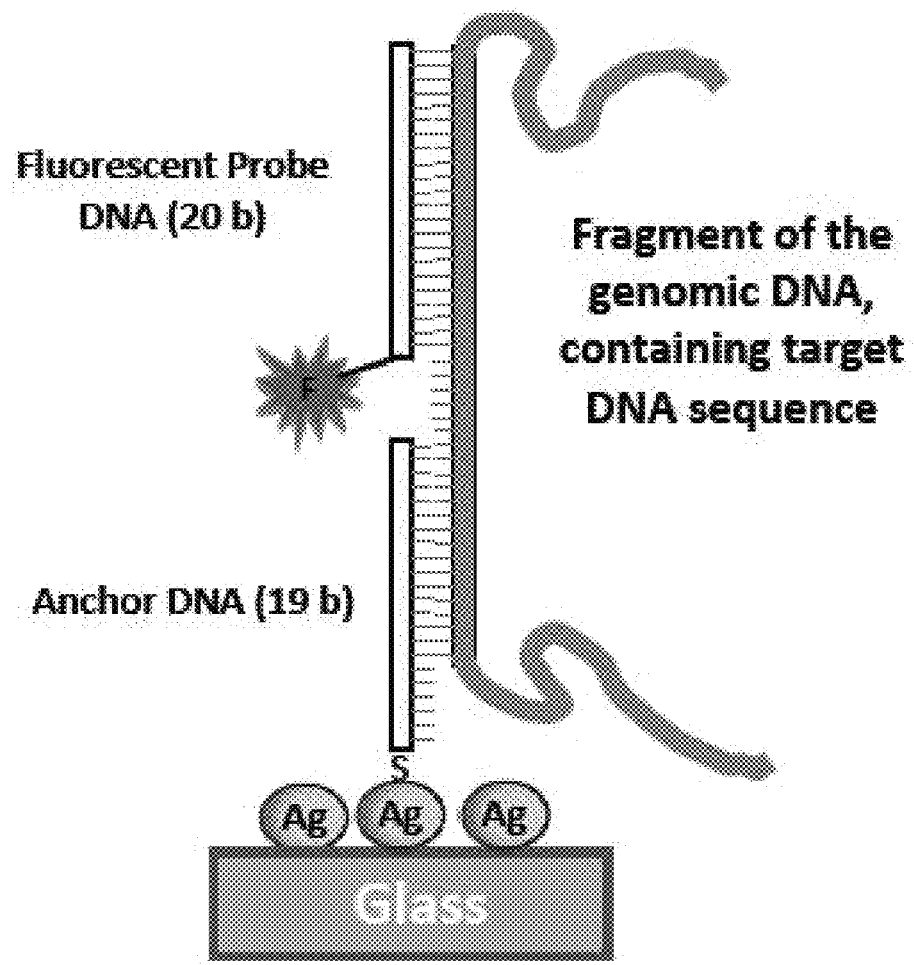

FIG. 33 shows the principles of the 3-piece DNA assay scaffold.

Figure 34:
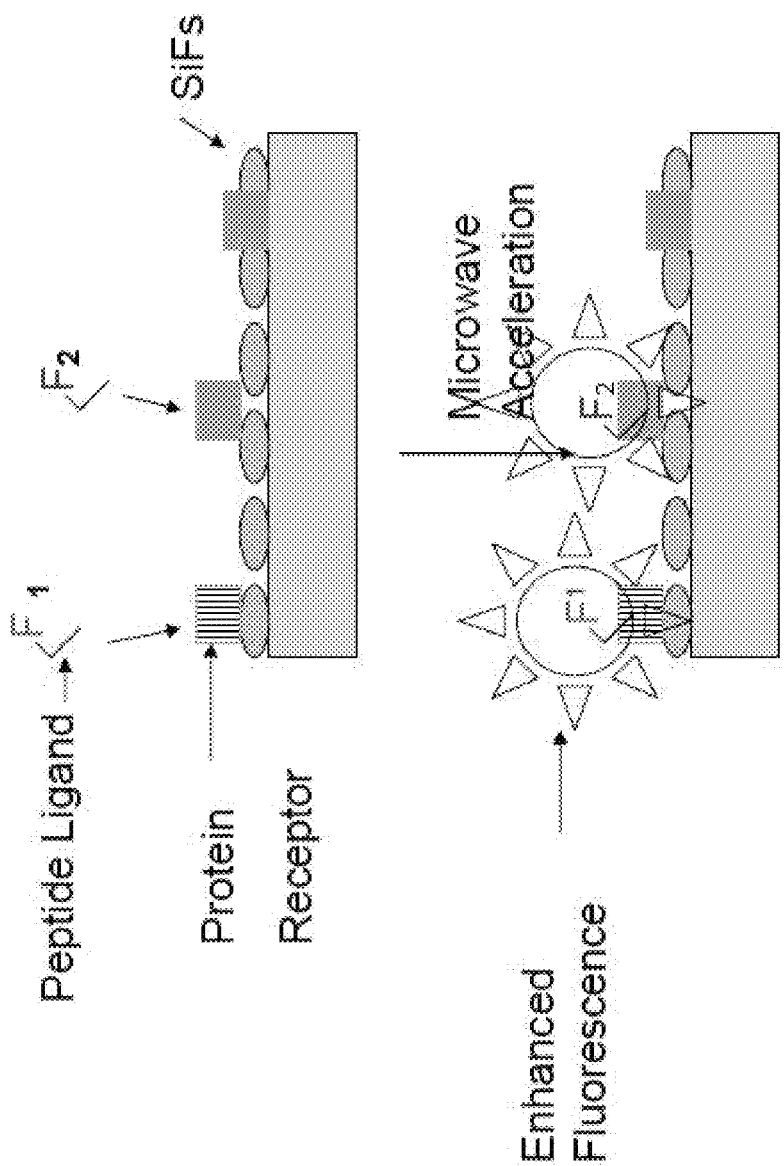

FIG. 34 shows different peptide labeled fluorophores that can bind to different proteins.

Figure 35:
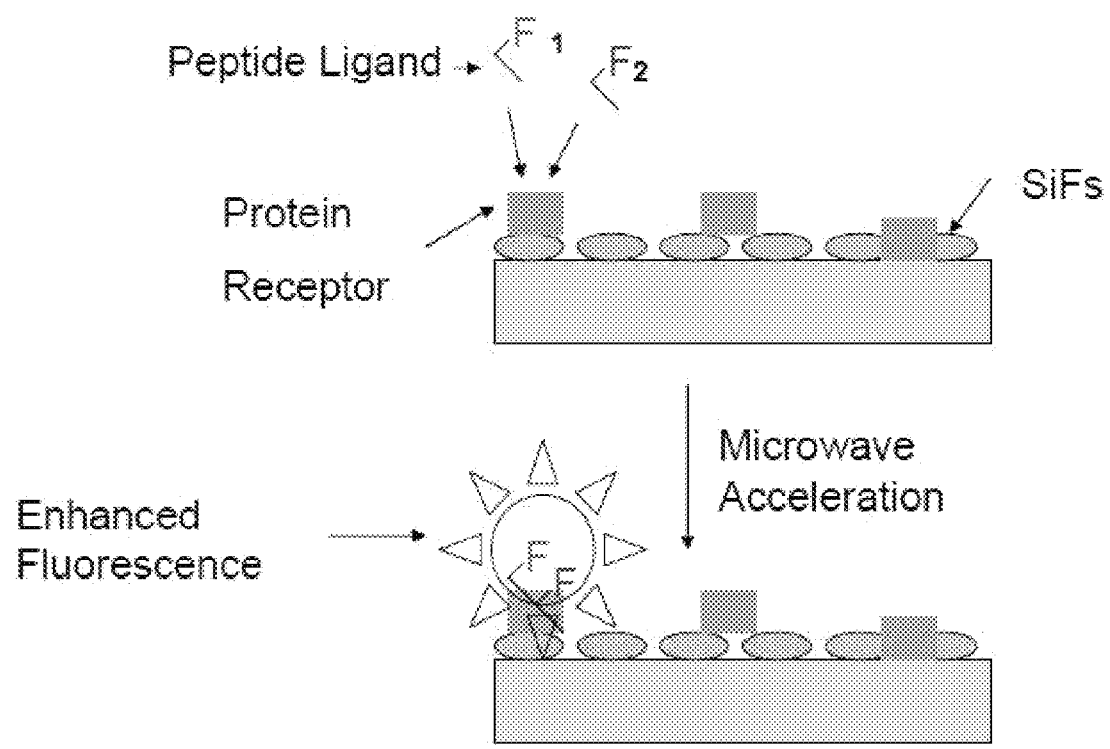

FIG. 35 shows that different peptide labeled fluorophores may bind to the same protein and results in metal-enhanced Fluorescence while the combination of fluorophore emissions provide a different color.

Figure 36:
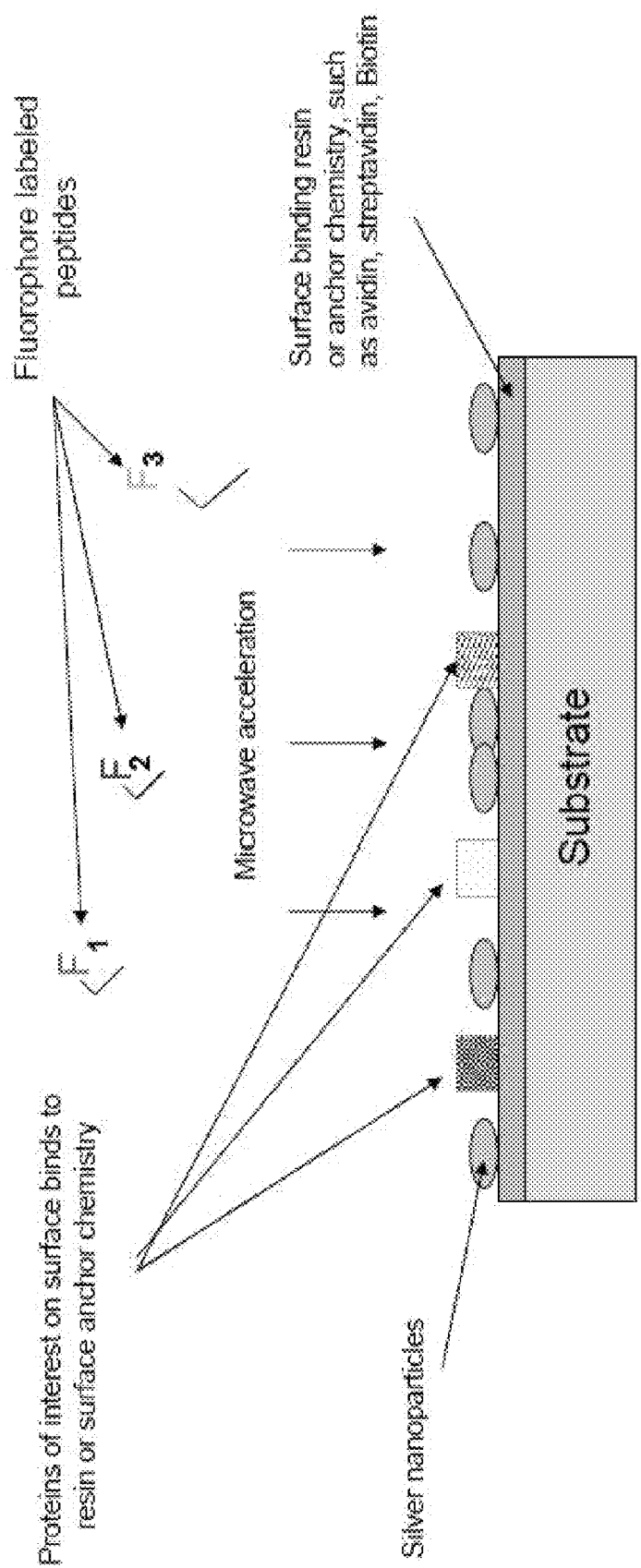

FIG. 36 shows that the stabilized proteins can be positioned directly on the substrate and positioned near the metallic nanoparticles.

DETAILED DESCRIPTION OF THE INVENTION

Figure 1:
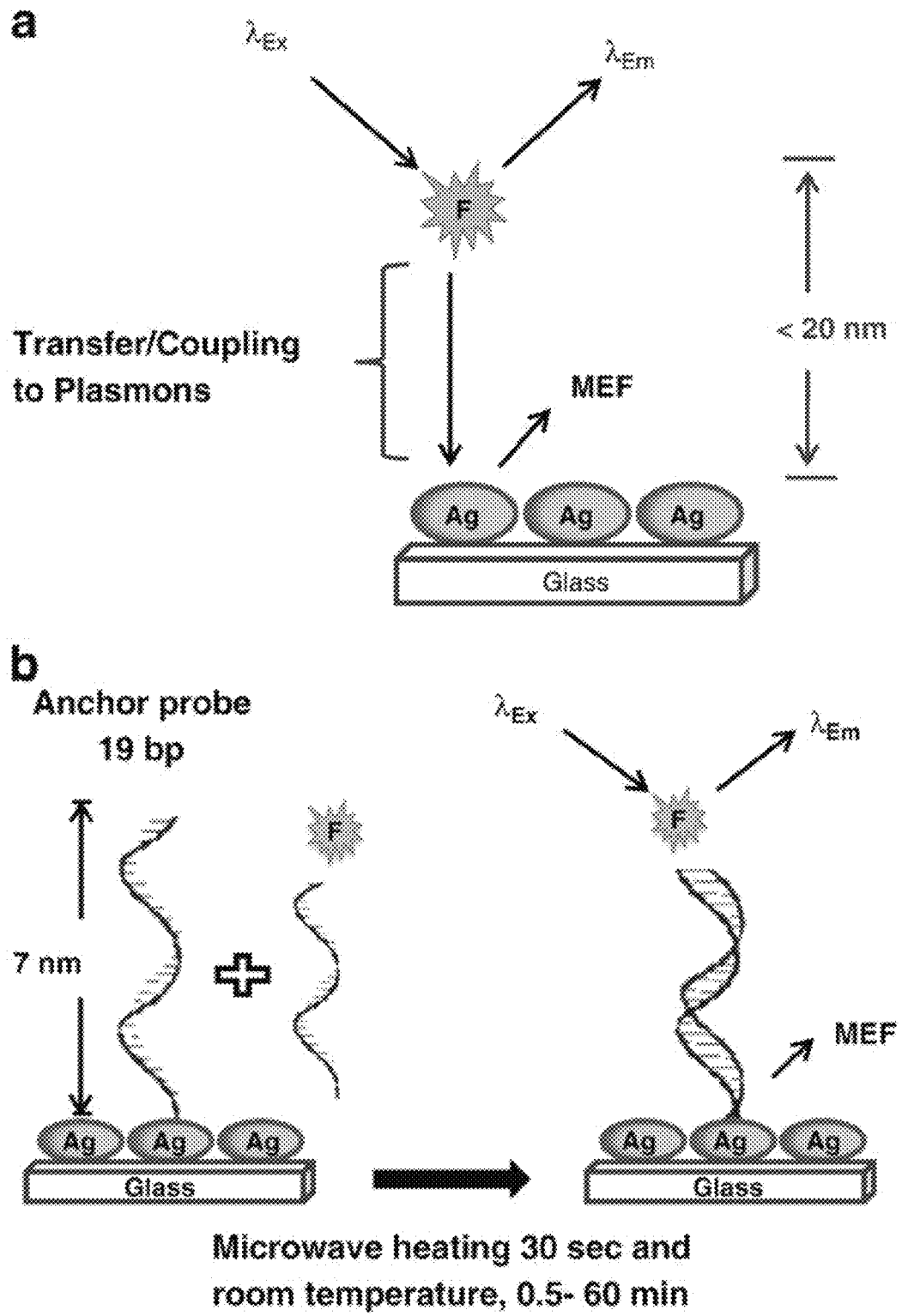
FIG. 1 shows (a) a graphical representation of the Metal-Enhanced Fluorescence (MEF) principles of the DNA quantitation assay and (b) MAMEF surface DNA capture assay, annealing with microwave energy and defined as "Rapid Catch and Signal" technology.

The present invention provides for expansion on the Metal-Enhanced Fluorescence (MEF) principles used in DNA quantitation assays and generally referred to as "catch and signal" technology, wherein DNA is caught and once caught in the assay system, a signal is available, are shown in FIG. 1. The MEF effect, i.e. enhancement of a fluorophore's brightness, exponentially depends on the distance between a chromophore and metallic nanoparticle, due to a short-range (0-50 nm) coupling of a chromophore's excited state electronic system with nanoparticle (NP) plasmons. As a result, only chromophores proximal to NPs increase their emission hundred's—thousand fold. Subsequently, hybridization is not only the event of a specific recognition of a target DNA, but also the creation of the MEF pair (fluorophore—NP plasmons), which enhances the fluorescence signal. Duplex annealing puts a fluorescent label on a short (~7 nm) enough leash, relative to a NP, thereby placing the label in the perfect condition for intense MEF[16,22,23]. A significant addition to this technology is microwave "heating" of the reacting system, which significantly speeds up the process of DNA hybridization[24], which is an important attractive feature of any bio-assay and causing a rapid response.

The present invention provides for further development of the "rapid catch and signal" RCS-DNA technology and the fundamental principles of the multiplexed nucleotide or protein assay for the simultaneous detection/quantification of multiple genome-specific DNAs or different proteins/peptides all within one well, and all within minutes and as quickly as 20 seconds.

Before the present invention is disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural references unless the content clearly dictates otherwise.

The term "biomolecule" means any carbon based molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, carbohydrates, steroids, flavins, proteins, DNA, RNA, oligonucleotides, peptide nucleic acids, fatty acids, sugar groups such as glucose etc., vitamins, cofactors, purines, pyrimidines, formycin, lipids, phytochrome, phytofluor, peptides, lipids, antibodies and phycobiliproptein.

The term "receptor-ligand" as used herein means any naturally occurring or unnaturally occurring binding couple wherein the components have affinity for each other. For example, the binding couple may include an antibody/antigen complex, viral coat ligand/protein cell receptor or any combination of probe and binding partner. The term "receptor" refers to a chemical group, molecule, biological agent, naturally occurring or synthetic that has an affinity for a specific chemical group, molecule, virus, probe or any biological agent target in a sample. The choice of a receptor-ligand for use in the present invention will be determined by nature of the disease, condition, infection or specific assay.

"Fluorophore," and "fluorescence label," used interchangeably herein, means any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™ sulfonyl chloride, BODIPY™, naphthalamine sulfonic acids including but not limited to 1-anilinon-aphthalene-8-sulfonic acid (ANS) and 6-(p-toluidinyl) naphthalen-e-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2 [(di-n-butylamino)-6 naphthyl]vinyl]pyridinium betaine (Naphtyl Styryl), 3,3' dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrimidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

Fluorophores with high radiative rates have high quantum yields and short lifetimes. Increasing the quantum yield requires decreasing the non-radiative rates $k_{nr}$, which is often only accomplished when using a low solution temperature or a fluorophore bound in a more rigid environment. The natural lifetime of a fluorophore, $\tau_n$, is the inverse of the radiative decay rate or the lifetime which would be observed if their quantum yields were unity. This value is determined by the oscillator strength (extinction coefficient) of the electronic transition. Hence, for almost all examples currently employed in fluorescence spectroscopy, the radiative decay rate is essentially constant. The modification and control of the radiative rate have also been referred as Radiative Decay Engineering (RDE), or "lightening rod" fluorescence enhancement effect. For example, enhanced intrinsic DNA fluorescence above metallic particles has recently been observed, which is typically not readily observable because of DNA's very low quantum yield of less than $10^{-4}$. The second favorable "lightening rod" effect also increases the fluorescence intensity by locally enhanced excitation. In this case, emission of fluorophores can be substantially enhanced irrespective of their quantum yields.

The reduction in lifetime of a fluorophore near a metal is due to an interaction between the fluorophore and metal particle, which enhances the radiative decay rate (quantum yield increase) or depending on distance, $d^{-3}$, causes quenching. It should be noted that lifetimes of fluorophores with high quantum yields (0.5) would decrease substantially more than the lifetimes of those with low quantum yields (0.1 and 0.01). A shorter excited-state lifetime also allows less photochemical reactions, which subsequently results in an increased fluorophore photostability. Notably, the use of low quantum yield fluorophores would lead to much larger fluorescence enhancements (i.e. $1/Q_0$) and could significantly reduce unwanted background emission from fluorophores distal from the silvered assay.

Fluorophore photostability is a primary concern in many applications of fluorescence. This is particularly true in single molecule spectroscopy. A shorter lifetime also allows for a larger photon flux. The maximum number of photons that are emitted each second by a fluorophore is roughly limited by the lifetime of its excited state. For example, a 10 ns lifetime can yield about $10^8$ photons per second per molecule, but in practice, only $10^3$ photons can be readily observed. The small number of observed photons is typically due to both photo-destruction and isotropic emission. If a metal surface decreases the lifetime, one can obtain more photons per second per molecule by appropriately increasing the incident intensity.

On the other hand, the metal-enhanced fluorescence provides enhanced intensity, while simultaneously shortening the lifetime. That is, it may be possible to decrease the excitation intensity, yet still see a significant increase in the emission intensity and photostability.

The emission enhancement may be observed at distances according to the type of fluorophore to be detected and the type, shape of the metal material, noting a difference between a film and a metallic island or colloid. For example, emission enhancement may be observed when a fluorophore distances about 5 nm to about 200 nm to metal surfaces. Preferable distances are about 5 nm to about 30 nm, and more preferably, 5 nm to about 20 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

Attaching of the fluorophore to a probe may be achieved by any of the techniques familiar to those skilled in the art. For example, the fluorophore may be covalently attached to the bimolecular probe by methods disclosed in U.S. Pat. No. 5,194,300 (Cheung) and U.S. Pat. No. 4,774,189 (Schwartz).

Embodiments of the present invention are also applicable to the use of different chemiluminescence labels or moieties which participate in light-producing reactions in the presence of a triggering agent or cofactor. In the present application, for purposes of example and without limitation, a preferred embodiment will be discussed in terms of chemiluminescence labels and triggering agent. The label affixed to the detector molecule will be referred to as the "label" or "label agent". For purposes herein, "triggering agent or cofactor" is broadly used to describe any chemical species, other than the chemiluminescence label, which participates in a reaction and which produces a detectable response. Chemiluminescence labels and triggering agents produce a light response. When more than one is used, then the light signal can be selected to be visually or detectably different, thus able to determine more than one target biomolecule.

Examples of suitable chemiluminescence labels include but without limitation, peroxidase, bacterial luciferase, firefly luciferase, functionalized iron-porphyrin derivatives, luminal, isoluminol, acridinium esters, sulfonamide and others. A recent chemiluminescent label includes xanthine oxidase with hypoxanthine as substrate. The triggering agent contains perborate, a Fe-EDTA complex and luminol. Choice of the particular chemiluminescence labels depends upon several factors which include the cost of preparing labeled members, the method to be used for covalent coupling to the detector molecule, and the size of the detector molecules and/or chemiluminescence label. Correspondingly, the choice of chemiluminescence triggering agent will depend upon the particular chemiluminescence label being used.

Chemiluminescent reactions have been intensely studied and are well documented in the literature. For example, peroxidase is well suited for attachment to the detector molecule for use as a chemiluminescence. The triggering agent effective for inducing light emission in the first reaction would then comprise hydrogen peroxide and luminol. Other triggering agents which could also be used to induce a light response in the presence of peroxidase include isobutyraldehyde and oxygen.

Procedures for labeling detector molecules, such as antibodies or antigens with peroxidase are known in the art. For example, to prepare peroxidase-labeled antibodies or antigens, peroxidase and antigens or antibodies are each reacted with N-succinimidyl 3-(2-pyridyldithio) proprionate (hereinafter SPDP) separately. SPDP-labeled peroxidase, or SPDP-labeled antigen or antibody is then reacted with dithiothreitol to produce thiol-labeled peroxidase, or thiol-labeled antigen or antibody. The thiol derivative is then allowed to couple with the SPDP-labeled antigen or antibody, or SPDP-labeled peroxidase.

Techniques for attaching antibodies or antigens to solid substrates are also well known in the art. For example, antibodies may be coupled covalently using glutaraldehyde to a silane derivative of borosilicate glass.

Although chemiluminescence detection has been successfully implemented, the sensitivity and specificity of these reactions require further improvements to facilitate early diagnosis of the prevalence of disease. In addition, most protein detection methodologies, most notably western blotting, are still not reliable methods for accurate quantification of low protein concentrations without investing in high-sensitivity detection schemes. Protein detection methodologies are also limited by antigen-antibody recognition steps that are generally kinetically very slow and require long incubation times; e.g., western blots require processing times in excess of 4 h. Thus, both the rapidity and sensitivity of small-molecule assays are still critical issues to be addressed to improve assay detection.

Figure 11:
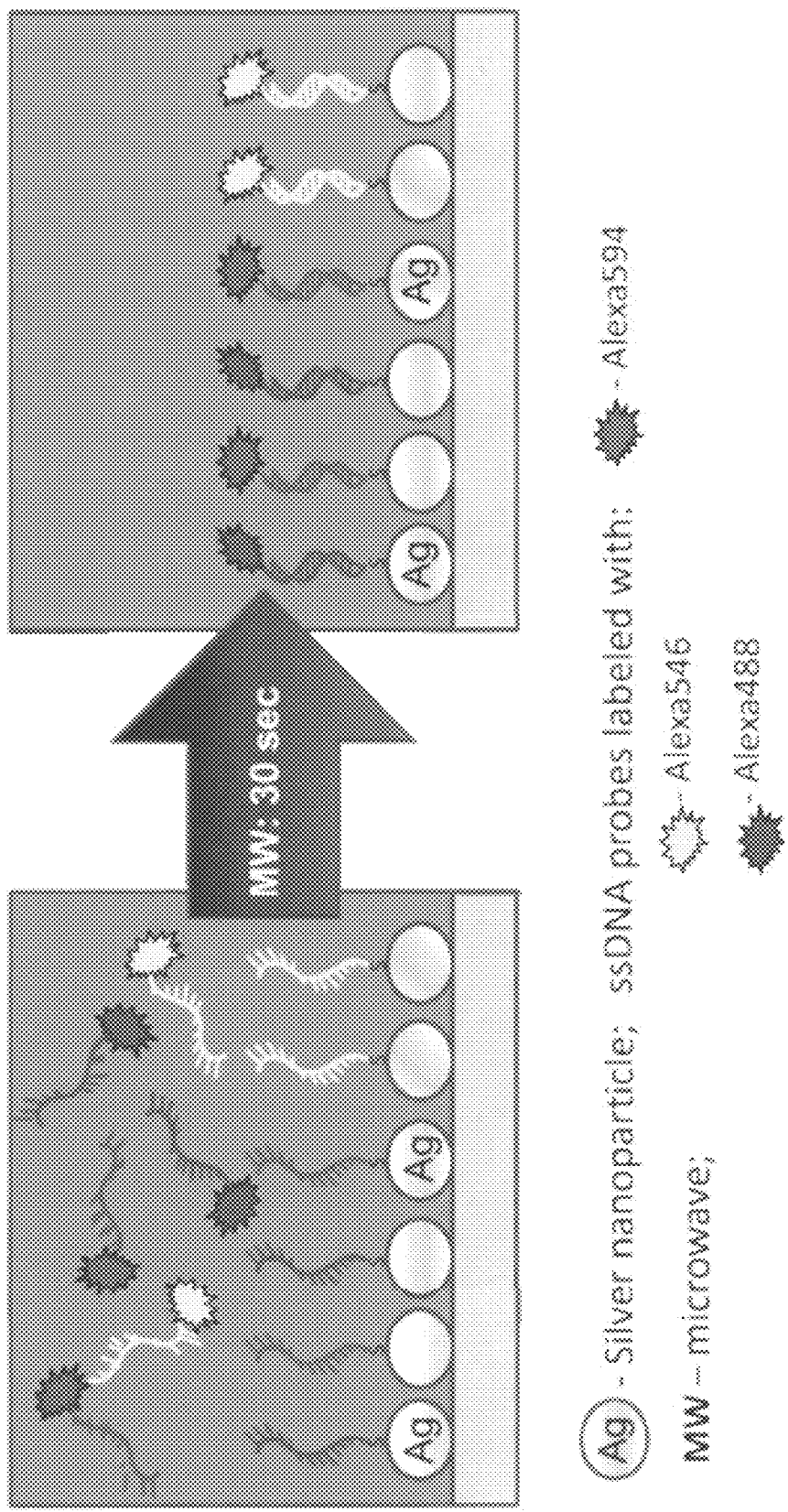
FIG. 11 shows the principles of the multiplexed multicolor (three colors in this instance) genomic DNA analysis approached based on microwave accelerated hybridization and MEF.

In an another embodiment, the present invention relates to detection of a nucleotide sequence. The nucleotide sequence communicatively connect to the metallic material can be quantified compared to the undetectable emission on non metallized surface. In this regard, the detection of RNA is accomplished by annealing a target RNA, tagged with a fluorophore, to an oligonucleotide anchor probe in a single step on a solid surface, where the fluorescence signal is intrinsically enhanced by silver nanoparticles as shown in MEF based RNA sensing platform systems of FIGS. 8 and 11.

"Nucleotide," as used herein refers to deoxyribonucleic acid (DNA) or ribonucleic acid (RNA), RNA can be unspliced or spliced mRNA, rRNA, tRNA, or antisense RNAi. DNA can be complementary DNA (cDNA), genomic DNA, or an antisense.

The nucleotides used as hybridization probes in the present inventor are typically designed to be specific for the desired sequence in order to decrease the probability of hybridizing to unrelated sequences. Such probes can be modified so as to be detectable using radionuclides, luminescent moieties, and so forth. Hybridization conditions also can be modified in order to achieve the desired specificity. For example, a moderately stringent hybridization condition may include: 2×SSC/0.1% SDS at about 37° C. or 42° C. (hybridization conditions); 0.5×SSC/0.1% SDS at about room temperature (low stringency wash); 0.5×SSC/0.1% SDS at about 42° C. (moderate stringency wash). An example of moderately-high stringency hybridization conditions is as follows: 0.1×SSC/0.1% SDS at about 52° C. (moderately-high stringency wash). An example of high stringency hybridization conditions is as follows: 0.1×SSC/0.1% SDS at about 65° C. (high stringency wash).

The nucleotides sequences of the present invention can be obtained using standard techniques known in the art (e.g., molecular cloning, chemical synthesis) and the purity can be determined by polyacrylamide or agarose gel electrophoresis, sequencing analysis, and the like. Polynucleotides also can be isolated using hybridization or computer-based techniques that are well known in the art. Such techniques include, but are not limited to: (1) hybridization of genomic DNA or cDNA libraries with probes to detect homologous nucleotide sequences; (2) antibody screening of polypeptides expressed by DNA sequences (e.g., using an expression library); (3) polymerase chain reaction (PCR) of genomic DNA or cDNA using primers capable of annealing to a nucleic acid sequence of interest; (4) computer searches of sequence databases for related sequences; and (5) differential screening of a subtracted nucleic acid library.

Increasing a binding reaction of the present invention may be achieved by using any device capable of generating and transmitting acoustic energy through any medium to transit ultrasonic atomizing energy. The ultrasonic emitting device can be placed in either the interior of a vessel or positioned adjacent thereto for transmitting energy into the vaporization vessel. The device may include components for the traditional electromagnetic stimulation of piezoelectric transducers, (man-made or naturally occurring), purely mechanical devices (such as high frequency air whistles or microphones), and laser devices. Individual components for acoustic energy systems are commercially available from a wide variety of manufacturers, which can be configured to particular applications and frequency ranges. (See Thomas Directory of American Manufacturers, Photonics Buyer's Guide, 1996, Microwave and RF, and Electronic Engineer's Master Catalogue).

Any oscillator or signal generator that produces a signal with predetermined characteristics such as frequency, mode, pulse duration, shape, and repetition rate may be used to generate acoustic frequencies for applying to the system of the present invention. Various oscillators or signal generators can be commercially purchased from a wide variety of manufacturers and in a variety of designs configured to particular applications and frequencies. Applicable transducers will include types that produce an acoustic wave within a range of frequencies (broadband) or for one specific frequency (narrowband) for frequencies ranging from hertz to gigahertz.

The acoustic delivery system will be variable depending on the application. For example, acoustic energy waves can be transmitted into liquid or solid source material either by direct contact of the source material with a transducer, or by coupling of transmission of the acoustic wave through another medium, which is itself in direct contact with the source material. If the source material is a liquid, a transducer can be placed in the liquid source material, or the walls of the vaporization vessel can be fabricated of a material that acts as a transducer thereby placing the liquid source material in direct contact with the transducer. Additionally, an acoustic energy emitting device may be positioned on the exterior of a system container for transmitting the appropriate energy. If the source material is a solid, a transducer can be placed in direct contact with it or the solid source material can be placed in a gas or liquid that is used as a coupling agent.

In the preferred acoustic frequencies any system that generates acoustic energy may be utilized. Preferably, the output of the ultrasonic generator is of a sufficient frequency to provide a movement flow within the system vessel to move molecules to the source of binding or reaction site without causing a large increase of heat in the system. For example, using the power output of 0.5 to 50 W at a frequency of 10 to 200 kHz, and more preferably from about 20 to 60 kHz and most preferably at about 40 kHz.

To obtain the maximum transfer of acoustical energy from one medium to another, the characteristic acoustical impedance of each medium is preferably as nearly equal to the other as possible. The matching medium is sandwiched between the other two and should be the appropriate thickness relative to the wavelength of the sound transmitted, and its acoustical impedance R should be nearly equal to ($R_1$: $R_2$). Any impedance matching device that is commercially available can be utilized in the present invention.

The system may include ultrasonic vessels wherein at least a section of the vessel includes a transducer such as a piezoelectric transducer to generate acoustic vibrations. Such transducers can be located in the bottom of a vessel or in a plate whereon a vessel may be placed. Further such transducers can be placed at different levels on the vessel walls to enhance fluid flow within the vessel.

The assay systems of the present invention may further comprise a light or laser source for directing an energy beam on any included excitable molecule to provide excitation energy. The laser beam may be positioned adjacent to the system for directing the beam at the molecular components. In the alternative the excitation may be delivered to the top or bottom of the metallic particles and surface substrate. The laser may be any device capable of focusing an energy beam at a particular point on the solid or liquid source material for excitation and the laser may transmit RF, infrared, microwave to UV energy.

Further, excitation light sources can include arc lamps and lasers, laser diodes and light emitting diode source, and both single and multiple photon excitation sources. In another embodiment, use of a Ti-sapphire laser, Laser Diode (LD) or Light Emitting Diode Sources (LEDs) may be used with the RNA assay of the present invention. For example, using 2-photon excitation at 700-1000 nm and also using short pulse width (<50 pi), high repetition rate (1-80 MHz), laser diode and LED (1 ns, 1-10 MHz) sources. The enhanced sensitivity of the assay using 2-photon excitation, as compared to 1-photon, can be shown by using series dilution with RNA, initially with the Ti-Sapphire system, and later with LEDs and LDs. If a fluorophore absorbs two photons simultaneously, it will absorb enough energy to be raised to an excited state. The fluorophore will then emit a single photon with a wavelength that depends on the fluorophore used and typically in the visible spectra. The use of the Ti-sapphire laser with infrared light has an added benefit, that being, longer wavelengths are scattered less, which is a benefit to high-resolution imaging. Importantly, there is reduced background signal level gained by using 2-photon excitation as compared to 1-photon excitation by utilizing localized excitation near by a metallic particles.

Any source, known to one skilled in the art may be used, such as a laser that emits light, wherein light is used in its broad sense, meaning electromagnetic radiation which propagates through space and includes not only visible light, but also infrared, ultraviolet radiation, acoustic or microwave energy. Thus, a single instrument placed above the surface of the assay or below the substrate surface can be used to generate energy to excite fluorescing molecules or a chemiluminescence reaction in addition to sonic or microwave energy. The light or sound waves can be emitted from a fiber continuously or intermittently, as desired, to increase the speed of chemical reactions within the assay system.

In one embodiment, the application of low level microwave heating of the sample may be used to speed up any chemical/biochemical kinetics within the system. Notably, low level microwaves do not destroy or denature proteins, DNA, or RNA, but instead heat the sample sufficiently to provide for accelerated kinetics such as binding or hybridization. In addition, the microwaves are not scattered by the metallic structures, which is contrary to most metal objects, such as that recognized by placing a spoon in a microwave oven.

Microwaves (about 0.3 to about 300 GHz) lie between the infrared and radiofrequency electromagnetic radiations. It is widely thought that microwaves accelerate chemical and biochemical reactions by the heating effect, where the heating essentially follows the principle of microwave dielectric loss. Polar molecules absorb microwave radiation through dipole rotations and hence are heated, where as non-polar molecules do not absorb due to lower dielectric constants are thus not heated. The polar molecules align themselves with the external applied field. In the conventional microwave oven cavity employed in this work, the radiation frequency (2450 MHz) changes sign $2.45 \times 10^9$ times per second. Heating occurs due to the tortional effect as the polar molecules rotate back and forth, continually realigning with the changing field, the molecular rotations being slower than the changing electric field. The dielectric constant, the ability of a molecule to be polarized by an electric field, indicates the capacity of the medium to be microwave heated. Thus, solvents such as water, methanol and dimethyl formamide are easily heated, where as microwaves are effectively transparent to hexane, toluene and diethylether. For metals, the attenuation of microwave radiation arises from the creation of currents resulting from charge carriers being displaced by the electric field. These conductance electrons are extremely mobile and unlike water molecules can be completely polarized in 10-18 s. In microwave cavity used in the present invention, the time required for the applied electric field to be reversed is far longer than this, in fact many orders of magnitude. If the metal particles are large, or form continuous strips, then large potential differences can result, which can produce dramatic discharges if they are large enough to break down the electric resistance of the medium separating the large metal particles. Interestingly, and most appropriate for the new assay platform described herein, small metal particles do not generate sufficiently large potential differences for this "arcing" phenomenon to occur. However, as discuss hereinbelow, the charge carriers which are displaced by the electric field are subject to resistance in the medium in which they travel due to collisions with the lattice phonons. This leads to Ohmic heating of the metallic structures in addition to the heating of any surface polar molecules. Intuitively, this leads to localized heating around the metallic structures in addition to the solvent, rapidly accelerating assay kinetics.

In the present invention, microwave radiation may be provided by an electromagnetic source having a frequency in a range between 0.3 and 10 GHz and a power level in a range between about 10 mwatts and 400 watts, more preferably from 30 mwatts to about 200 watts. Any source, known to one skilled in the art may be used, such as a laser that emits light, wherein light is used in its broad sense, meaning electromagnetic radiation which propagates through space and includes not only visible light, but also infrared, ultraviolet and microwave radiation. Thus, a single instrument placed above the surface of the assay can be used to generate the microwave energy and energy to excite fluorescing molecules. The light can be emitted from a fiber continuously or intermittently, as desired, to maintain the metallic particles at a predetermined temperature such that it is capable of increasing the speed of chemical reactions within the assay system. The microwave radiation may be emitted continuously or intermittently (pulsed), as desired. In the alternative, microwave energy can be supplied through a hollow wave guide for conveying microwave energy from a suitable magnetron. The microwave energy is preferably adjusted to cause an increase of heat within the metallic material without causing damage to any biological materials in the assay system.

Emitting signals, such as fluorescence or chemiluminescence signals can be detected using devices including, but not limited to, a spectrofluorometer having a light source and detector. Detectors can include photomultiplier tubes. Additionally, it is advantageous for the device to have a monochromator so that specific wavelengths of light may be used to excite a molecule or to detect emissions at a specific wavelength. When a sample containing a fluorophore is placed in the spectrofluorometer and exposed to an amount of exciting radiation, the fluorophore emits radiation that is detected by a photomultiplier tube. Collection of the emitting signals may be collected from the top or bottom of the substrate or both simultaneously.

Preparation of Metal Islands

The island particles are prepared in clean beakers by reduction of metal ions using various reducing agents. For example, sodium hydroxide is added to a rapidly stirred silver nitrate solution forming a brown precipitate. Ammonium hydroxide is added to re-dissolve the precipitate. The solution is cooled and dried quartz slides are added to the beaker, followed by glucose. After stirring for 2 minutes, the mixture is warmed to 30° C. After 10-15 minutes, the mixture turns yellow-green and becomes cloudy. A thin film of silver particles has formed on the slides as can be seen from their brown green color. The slides are rinsed with pure water prior to use.

Alternative procedures for preparing metal particles are also available. Silver is primarily used because of the familiar color from the longer surface plasmon absorption of silver.

Preparation of Silver Colloids

Colloids can be prepared as suspensions by citrate reduction metals. Preferred metals are silver and gold. Again, gold may be because of the absorption of gold at shorter wavelengths. However, gold colloids may be used with longer wavelength red and NIR fluorophores.

The size of the colloids and their homogeneity can be determined by the extensive publications on the optical properties of metal particles available and the effects of interface chemistry on the optical property of colloids.

Silver island films can be formed by a chemical reduction of a silver salt on the quartz surface, which are relatively simple to fabricate. However, this approach does not provide a control of particle size, or distance of the fluorophores from the surface. Enhancements of 1000 fold have been with the realization that sample geometries have been heterogeneous and the enhancement factors spatially averaged.

Metal particles can be bound to a surface by placing functional chemical groups such as cyanide (CN), amine (NH$_2$) or thiol (SH), on a glass or polymer substrate. Metal colloids are known to spontaneously bind to such surfaces with high affinity.

In one embodiment, detection occurs without binding the molecules to the sensor or support. The molecule to be detected is not chemically bound. The molecule to be detected may remain in solution and not directly or indirectly interact with the metal particles, coatings or film spacer layers.

Metallic colloids (or various other non-spherical shapes/particles) may also be incorporated into organic polymers, covalently or non-covalently, to form polymeric matrices, wherein the distance from diffusing species affords an increase in radiative decay rate and thus, an increase in quantum yield. Such polymeric matrices are ideal for sensing/flowing sensing applications of low concentration species.

Polymers containing metal particles may have other applications, including but not limited to, size inclusion/exclusion sensing of non-fluorescent species, increased photostability of embedded fluorophores, single pore single molecule detection, and porous polymers which allow diffusing analytes or antibodies, resulting in a detectable and quantifiable signal change in the analyte or antibody or respective transduction element.

This embodiment of the present invention may also have vast applications in clinical medicine, environmental monitoring applications, homeland security such as rapid detection of low concentration species, industrial processes, pharmaceutical industries such as monitoring species, and sensors for use in reduced atmospheres such as biohazard clean rooms and space light.

Methods and Materials

Silver nitrate (99.9%), sodium hydroxide (99.996%), ammonium hydroxide (30%), D-glucose and premium quality APS-coated glass slides (75×25 mm) were obtained from Sigma-Aldrich.

Figure 2:
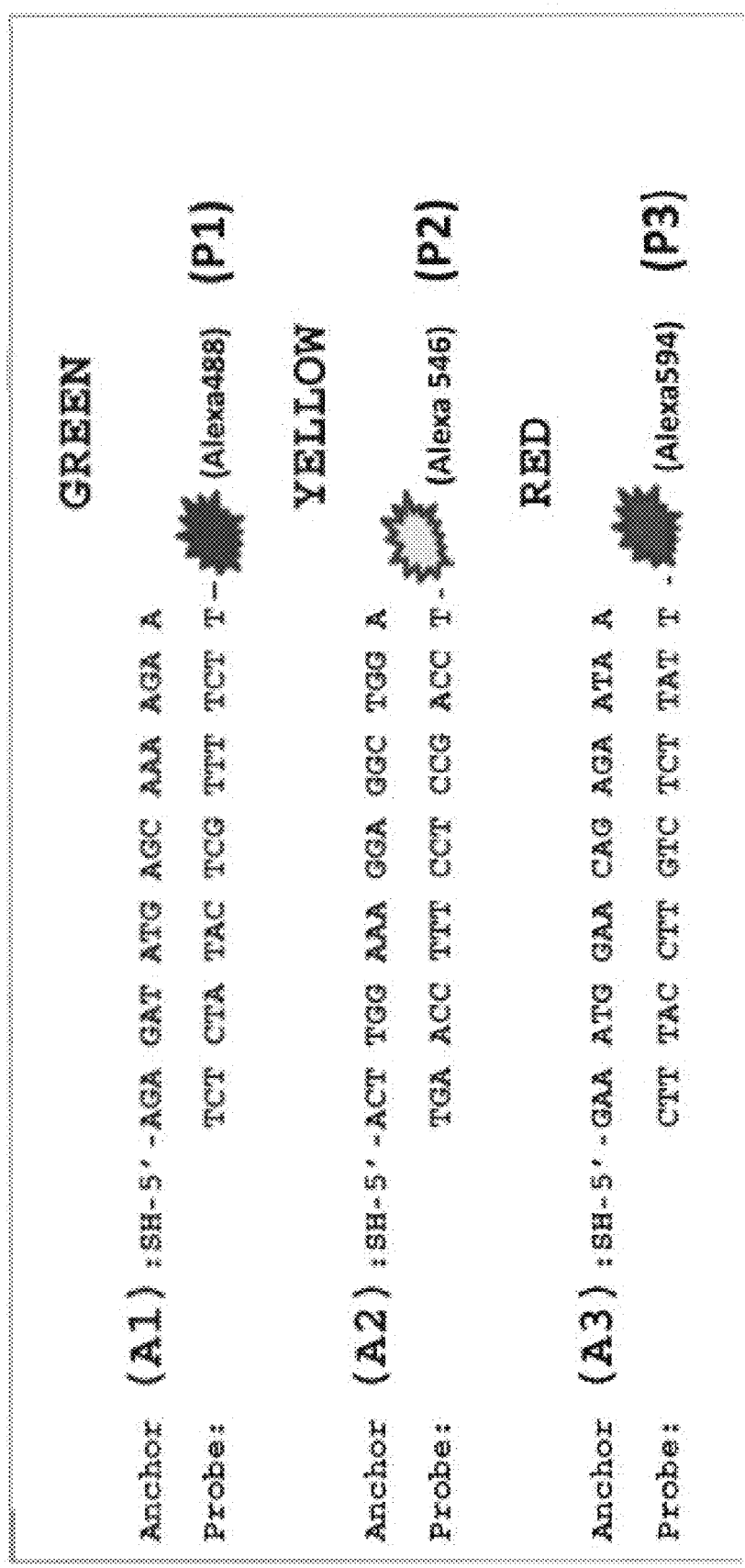
FIG. 2 shows the sequences of the Anchor and Probe ssDNAs. The DNA sequences used in this study are fragments of Chinese hamster ovary (CHO) Alu sequence. (A1 (AGA GAT ATG AGC AAA AGA A) (SEQ ID NO: 1)); (P1 (TCT CTA TACT CG TTT TCT T) (SEQ ID NO: 2)); (A2 (ACT TGG AAA GGA GGC TGG A) (SEQ ID NO: 3)); (P2 (TGA ACC TTT CCT CCG ACC T) (SEQ ID NO: 4)); (A3 (GAA ATG GAA CA GAGA ATA A) (SEQ ID NO: 5)); (P3 (CTT TAC CTT GTC TCT TAT T) (SEQ ID NO: 6)).

The 19 base DNA sequences used in this study are fragments of Chinese hamster ovary (CHO) Alu sequence. Oligonucleotides were purchased from Integrated DNA Technologies, Inc. (FIG. 2). Synthesis of five 19 base long 'DNA oligos of different sequences was ordered in Integrated DNA Technologies, IDT Inc. (FIG. 2). Since these DNA fragments contain sequences from Chinese hamster ovary (CHO) Alu DNA sequence, they can serve as the markers for clinical diagnostics. The probe-DNAs were labeled with Alexa chromophores: 488, 514, 546, 594 and 647. The optical properties of the dyes conjugated to probe-DNAs are shown in the Table 1.

| Dye | Absorption max, nm | Emission max, nm | *Extinction coefficient, M$^{-1}$cm$^{-1}$ | *Quantum Yield (Q) | Lifetime (T), nsec |
|---|---|---|---|---|---|
| Alexa-488 | 492.6 | 515.3 | 71,000 | 0.92 | 4.2 |
| Alexa-514 | 515.6 | 538.5 | 80,000 | — | 4.0 |
| Alexa-548 | 556.0 | 570.3 | 104,000 | 0.79 | 4.0 |
| Alexa-594 | 587.2 | 609.2 | 73,000 | 0.66 | 4.0 |
| Alexa-647 | 650.6 | 664.7 | 239,000 | 0.33 | 1.1 |

*data were taken from invitrogen (www.invitrogen.com)

Preparation of silver island films (SiFs) on glass slides was performed as described previously[25, 36]. The optical density of SiF-slides measured at the plasmon resonance absorption maximum (~410 nm) was 0.5-0.6 o.u.

Attachment of thiolated Anchor-DNA to silver coated slides. Attachment of thiolated single stranded (anchor) DNAs to SiFs was performed as previously described.[18]. The thiolated DNA, 5'/5ThioMC6-D/-ssDNA, contains a "cap" (5'-Thio-Modifier), which prevents DNA strands from spontaneous dimerization by formation of a S—S linkage. Subsequently, before attachment of the DNA to silver island films, the first step is an activation of DNA, i.e. a cleavage of a disulfide bond between a thiol-modifier group and DNA. DNA was subsequently resuspended in TE buffer, and 100 µl of DNA solution (43 µM) was mixed with 20 µl of DTT (250 µM in TE buffer) and incubated at ambient temperature for 30 min or by 30 sec irradiation of the solution in microwave cavity (GE Compact Microwave Model: JES735BF, frequency 2.45 GHz, power 700 W). Excess of the activated DNA in 6 mM DTT, TE buffer, pH 7.4 was stored at –20° C. The deprotected DNA solution was diluted 40-fold with TE buffer and immediately loaded on SiF-slides. Excess of the activated DNA in 6 mM DTT, TE buffer, pH 7.4 was stored at –20 C. Incubation time of the activated DNA on the SiF surface was 1 h at room temperature.

Measurements of fluorescence of the DNA samples were made by using a Fiber Optic Spectrometer (HD2000) from Ocean Optics, Inc. Excitation of the chromophores was undertaken using 473, 532 or 594 nm CW laser lines. Long-pass razor-edge filters (Semrock, USA) were used to cut-off excitation light in the registration channel.

The real-color photographs of metal-enhanced fluorescence from wells, containing the hybridized assay, were taken with an Olympus Digital camera (C-740, 3.2 Mega Pixel, 106 Optical Zoom). To cut-off excitation light the same long-pass filters were used, as was used to record the emission spectra.

DNA hybridization on SiF-surface. DNA annealing in wells was performed by the incubation of 70 ul of fluorophore labeled DNA oligos (target-DNA) with thiolated oligomers (anchor-DNA), immobilized on SiFs, in TE buffer for 30 s in a microwave cavity (GE Compact Microwave Model: JES735BF, frequency 2.45 GHz, power 700 W). Microwave irradiation power was reduced to 20%, which corresponded to 140 W over the entire cavity. Room temperature DNA hybridization was performed using the procedure above, except that the assay was completed at room temperature instead of using microwave irradiation for acceleration.

Kinetics of DNA hybridization to the SiF-surface. The hybridization kinetics of the probe-ssDNAs with the anchor-DNA, immobilized on the SiFs surface, was monitored by measuring the fluorescence intensity from the wells at certain time intervals. For the DNA hybridization in individual wells, the reaction was halted at different incubation times by washing the well with TE buffer.

Thermal imaging of the samples upon microwave irradiation. Thermal imaging was undertaken using the procedure described previously[40]. A sapphire plate 2.54 cm in diameter and 1 mm thick (Swiss Jewel), transparent for the infrared (IR) spectral region, was placed above the cavity opening to allow collection of the thermal image, i.e. the temperature distributions of the samples. The sapphire plate and the SiF-glass slide formed a sandwich with the DNA solution contained inside. The samples were inverted such that the SiF surface faced downward towards the registration channel. Infrared emission from the sample in the microwave cavity was imaged by reflecting the IR-radiation from a gold mirror onto a thermal imaging camera (Silver 420 M; Electrophysics Corp., Fairfield, N.J.) that is equipped with a close-up lens, and provides a resolution of approximately 300 µm.

Results and Discussions

Characterization of DNA-Scaffold Formation on the SiF-Surface.

Figure 3:
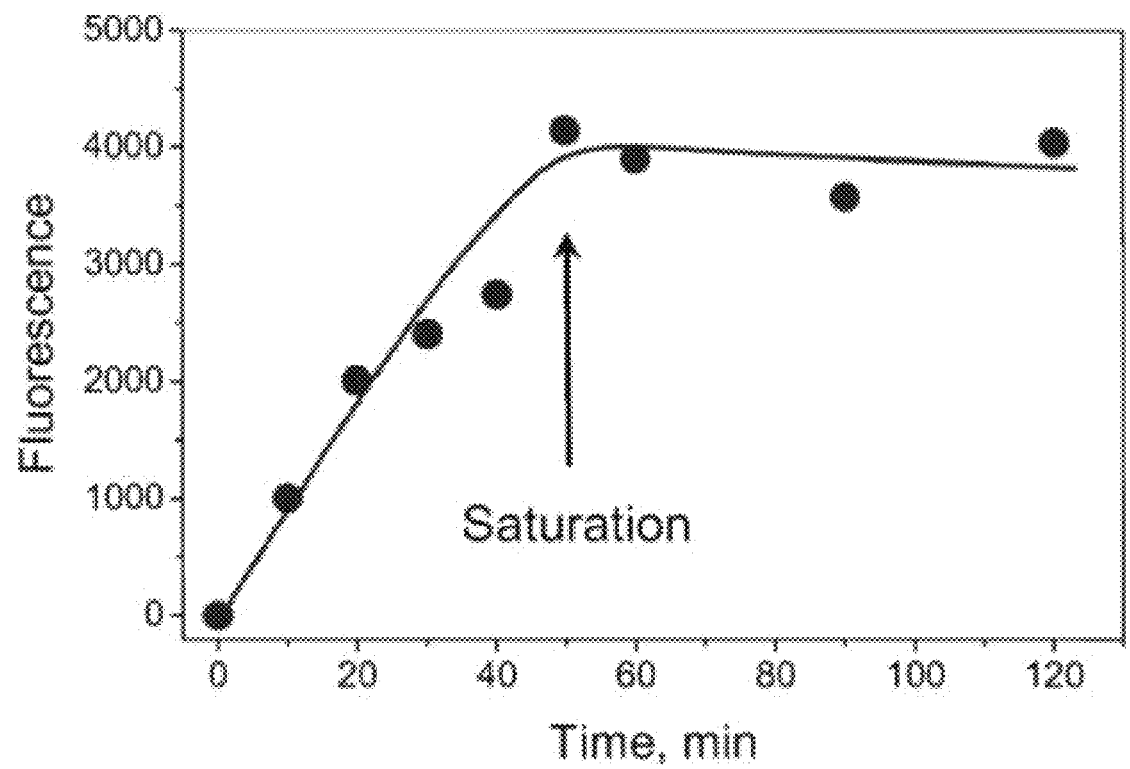
FIG. 3 shows the kinetics of an Anchor-ssDNA-SH attachment to a silver nanoparticle surface (SiFs). Full saturation of the SiF surface with a reactive anchor-ssDNA-SH occurs at ≈40-50 minutes. The concentration of the Anchor-DNA (A1) was 1 µM. Anchor DNA attachment reaction to the silver surface was stopped at different times by washing wells with buffer. To "visualize" anchor-DNA (A1), attached to silver, microwave accelerated hybridization with the complementary fluorophore labeled Probe-DNA (P1) was undertaken. The concentration of Probe-DNA loaded into wells was 1 µM.

Incubation of thiolated single stranded DNA on the SiF surface leads to DNA attachment to silver nanoparticles (NPs)[25]. DNA-scaffold development around NPs is time dependent and ceases upon saturation on the silver surface. The anchor-DNA is not labeled with a fluorophore and, consequently, one cannot directly monitor the kinetics of DNA scaffolding. Subsequently, to visualize anchor-DNA, affixed to the silver surface, we hybridized it with the fluorophore-labeled complementary DNA (probe-DNA). Consequently, due to the duplex annealing, the observed fluorescence intensity is linearly proportional to the amount of the anchor-DNA on the SiF-surface. FIG. 3 shows the kinetics of the anchor-DNA scaffold formation. During the first 20-30 minutes the amount of attached DNA almost linearly increases with time, showing a high rate of reaction. In about 50-60 minutes the silver surface becomes saturated and a further increase in the incubation time does not show any additional increase in fluorescence, i.e. any additional attachment of DNA to the silver nanoparticle surface. Hence, under these conditions, full saturation of the SiF-surface occurs in about 1 hour.

DNA Hybridization on a Surface: Microwave Acceleration of the DNA Annealing.

Figure 4:
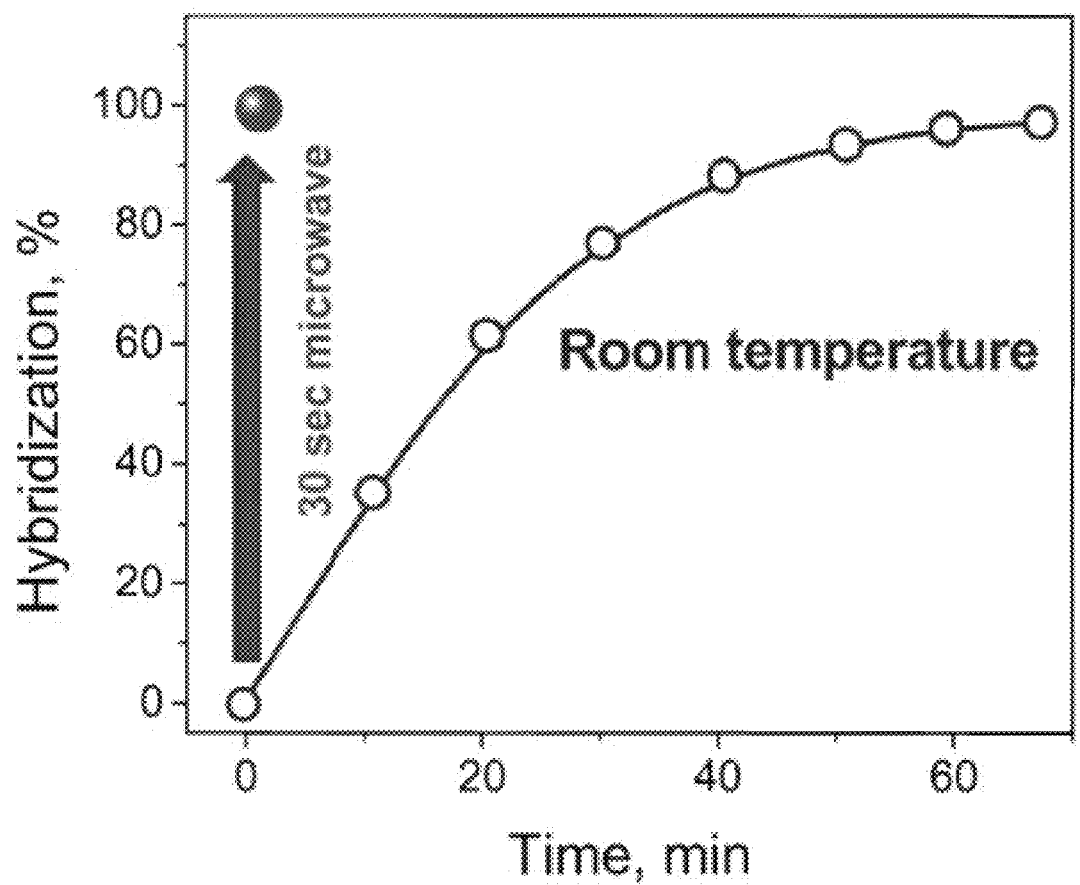
FIG. 4 shows the kinetics of hybridization of the Probe-DNA-Alexa 488 (P1) with the Anchor-DNA (A1) scaffold, attached to the silver nanoparticle surface (SiFs). Hybridization was with (closed circle) and without (open circles) 30 sec microwave irradiation. The hybridization reaction was halted by washing the wells with buffer followed by the measurement of the fluorescence signal from the wells.

Hybridization of DNA on a surface at ambient temperature is a relatively slow process (FIG. 4). The slow kinetics of hybridization at ambient temperature can readily be explained by the quite slow diffusion of the probe-DNA from the bulk solution to the capture DNA scaffold, formed on the silvered surface. Also it is possible that the competition between inter- and intra-molecular interactions[26] may decrease the rate of DNA hybridization.

In general, the kinetics of hybridization can be expressed by the following equation:

$$i.\ \text{Hybridization},\ \% = (1 - e^{-t/\tau}) \times 100\%, \quad (1)$$

where $\tau$ is a characteristic time of hybridization. Fitting of the data, shown in FIG. 4, using Eq. 1 gives a characteristic time $\tau = 23$ minutes. Hybridization of DNA on the surface depends on transport of a complementary ssDNA from the bulk volume to the 2D plane containing the anchor-ssDNA. In stationary conditions, as it is in the ambient temperature condition, the main cause of the DNA transport is diffusion, which can readily be described by the equation: $d = [t/(2D)]^{0.5}$, where d is a diffusion distance along one axis, t is time and D is the diffusion coefficient. If it is assumed that the diffusion coefficient of the short anchor-ssDNA is about $10^{-6}$ cm$^2$/s[27] then during the characteristic hybridization time ($\tau$) an anchor-ssDNA can travel by diffusing towards the surface with a mean distance of about 0.5 mm. This means that the probe-ssDNA, which anneals with an anchor-ssDNA on SiFs is in fact a thin layer proximal to the surface. It should be noted that the calculated distance is a maximum estimate and this value can be smaller depending on the concentration of the probe-ssDNA in the loading solution.

Notably, upon microwave (MW) irradiation the DNA hybridization proceeds almost immediately, the characteristic hybridization time $\tau_{mw} \ll 30$ sec (FIG. 4). The origin of the MW effect on kinetic parameters of DNA hybridization on a surface is not fully developed today. One can however assume that MW heating of the system influences DNA transport processes, i.e. the rate of the molecular diffusion and mass transport[28]. It is well known that MW irradiation, by interacting with the dipole moment of water molecules, increases the rate of their movement and subsequently enhances molecular thermodynamic temperature. Conversely, silver nanoparticles, immobilized on a glass surface, cannot move and electrons trapped in a small (100-300 nm) particle volume, are outside of the resonance condition with the MW field and, consequently, could not absorb MW energy (the MW radiation wavelength is ~12 cm.). Subsequently, pulses of MW radiation applied to the assay system induce a sharp temperature gradient between the "cold" SiF-surface and the much warmer solvent, which stimulates the active mass transport within the wells. According to the Einstein-Stokes equation[29,30], the rate of the molecular diffusion does not sufficiently change with temperature and it cannot alone explain the extremely high rate of the DNA hybridization upon microwave irradiation. Other studies have shown[17,28] that there is no biomolecule denaturation at these low microwave powers.

An additional feature of the Microwave-Accelerated approach is the destabilization of intramolecular structures in ssDNA, by disordering the hydration of the DNA polymer, which ultimately plays a significant role in stabilization of the DNA molecule conformation[31,32], and by increasing internal DNA strand flexibility. This is subsequently thought to significantly accelerate specific inter-molecular hybridization.

Characterization of the Multiplexed 3-Color DNA Assay.

Figure 12:
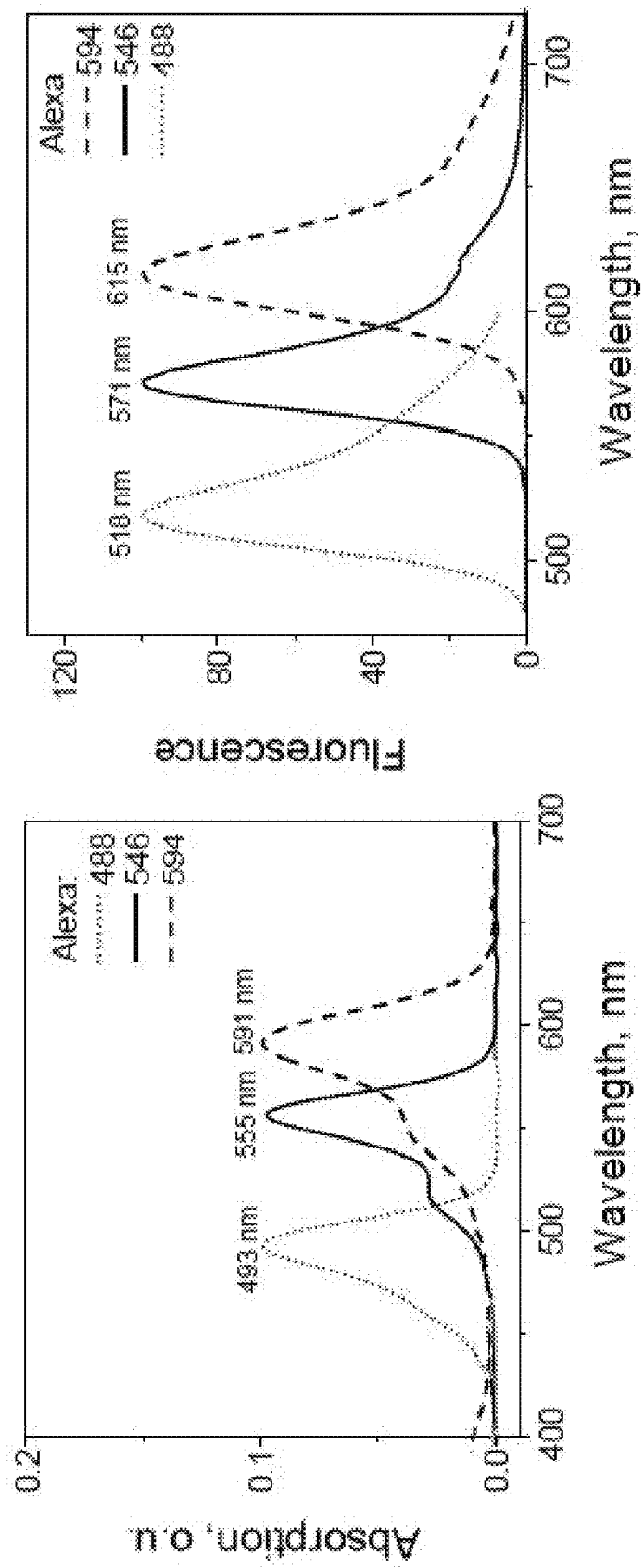
FIG. 12 shows the absorption and fluorescence spectra of the Alexa chromophores attached to probe DNAs.

The multiplexed 3-color DNA Catch and Signal (DNA-RCS) technology platform is based on the fast sequence specific recognition and annealing of DNA strands in solution with complementary ssDNAs, immobilized on the surface, (catch), and the sensing of this event by appearance of spectrally different emission (signal) all within one sample well. Each emission (color) corresponds to a DNA fragment Which contains the specific sequence and is hybridized to the surface complementary DNA target strand. The absorption and fluorescence spectra of the different color dyes, from green to red, are shown in FIG. 12. As described above, acceleration of the hybridization process occurs due to microwave irradiation, which significantly speeds up the rate of molecular recognition between DNA strands (see FIG. 11). Subsequently, fluorophore labeled DNAs move from bulk solution to the close proximity of the silver nanoparticles ($\approx 7$ nm), which Ultimately creates the favorable condition fix intensive MEF and, subsequently, a large increase in fluorophore brightness, which is evident in FIG. 1.

Despite the apparent simplicity of this DNA-RCS assay, the practical utilization of this technology requires thorough investigation for each multiplexed assay, which includes a study and determination of the DNA hybridization cross-selectivity; DNA density on the silvered surface, the dependence of fluorophore emission intensity upon the amount of specific DNA hybridization (important for the DNA quantitation technology), and, finally, measurement of the absolute MEF effect, which arises from proximity of hybridization-sensing fluorophores to the silver nanoparticles[16,18,22].

Cross-Selectivity of DNA Hybridization on Surface.

Figure 5:
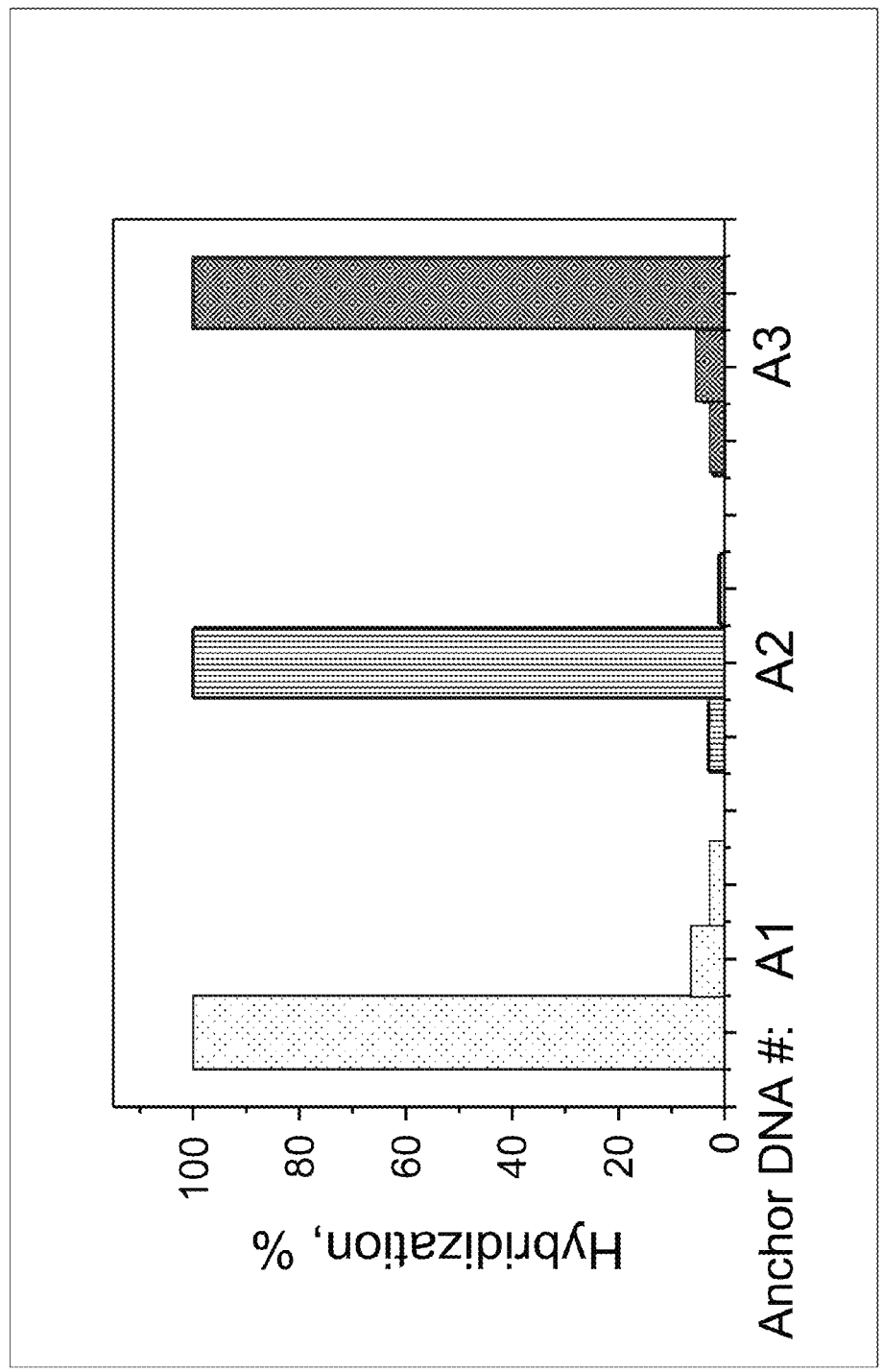
FIG. 5 show the cross-selectivity of the molecular recognition (hybridization). Hybridization of a Probe DNA with an Anchor DNA scaffold on the SiFs was accelerated using 30 sec microwave irradiation.

Specificity of hybridization plays a crucial role in our multiplexed DNA-RCS technology because it assumes the highly selective catch of a certain DNA sequence from a mixture of different DNA fragments. It should be noted that MW-accelerated hybridization occurs at sufficiently lower temperatures than the temperature of DNA melting ($T_m \approx 50$-$60°$ C.), similarly to that used for PCR (annealing temperature is 45-65° C.). To examine the cross-selective recognition between different probe- and anchor-DNAs, the following set of hybridizations was performed: probe-DNA ($P_i$) was hybridized with anchor-DNA ($A_j$), attached to SiFs, where i=1, 2, 3 and j=1, 2, 3, i.e. $P_i/A_j$ hybridization. FIG. 5 shows the results of the hybridization for different probe-DNAs with one of the anchor-DNAs. The cross-selectivity (CS, %) of hybridization can be determined as a ratio of signal from the complementary pair of ssDNAs to the total signal. For example, CS for the anchor-DNA ($A_1$) can be expressed by the following equation:

$$CS(A_1)=F(P_1/A_1)/[F(P_1/A_1)+F(P_2/A_1)+F(P_3/A_1)]\times 100\% \quad (2)$$

On average, for the three anchor-DNAs ($A_1$, $A_2$ and $A_3$) used in this testing, the CS was better than 98% (FIG. 5). Therefore, in essence, single stranded anchor-DNA molecules placed onto a 2D flat surface can rapidly and effectively catch from the solution mixture their sequence specific partner and form a hybridized duplex, within seconds.

Determining Surface Density of DNA.

Figure 6:
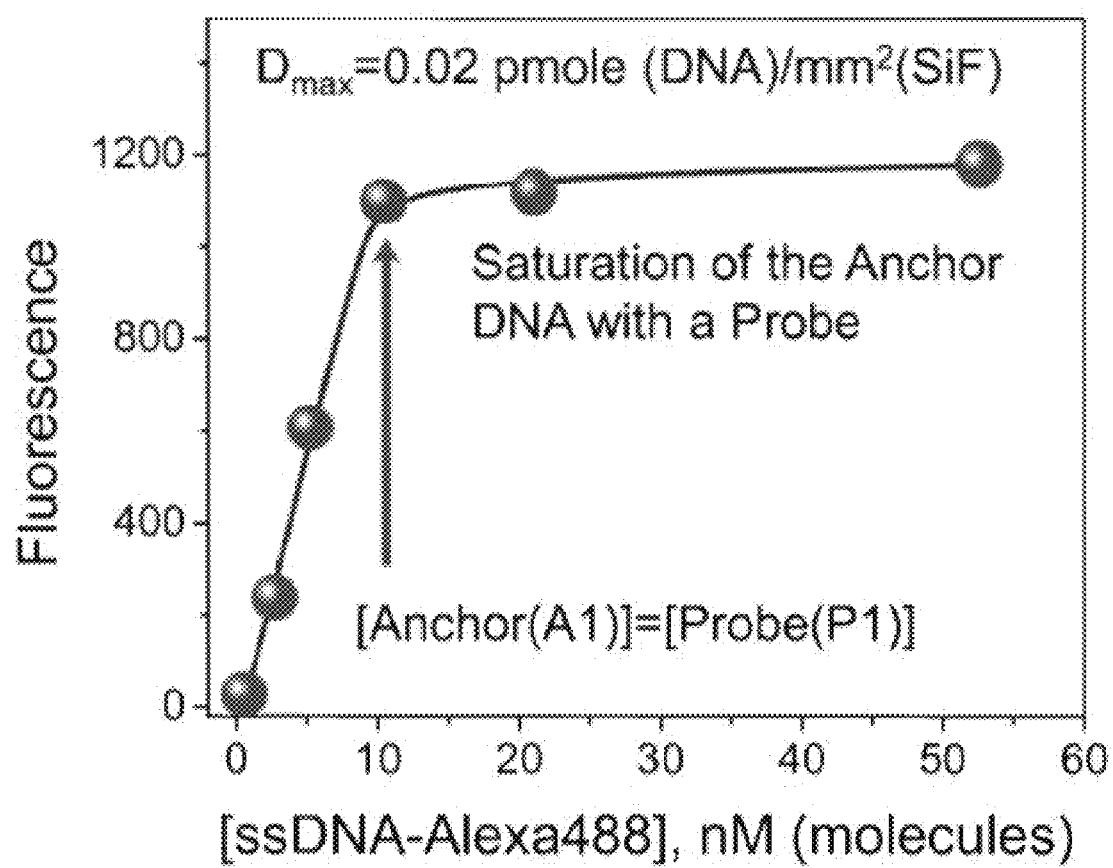
FIG. 6 shows the determination of quantity of Anchor-ssDNA attached to the SiF surface. Anchor-ssDNA-SH (A1) was pre-incubated on SiFs for 1 hour. The Anchor-DNA scaffold around the nanoparticles was subsequently hybridized with an increasing amount of labeled Probe-ssDNA (P1).
Figure 7:
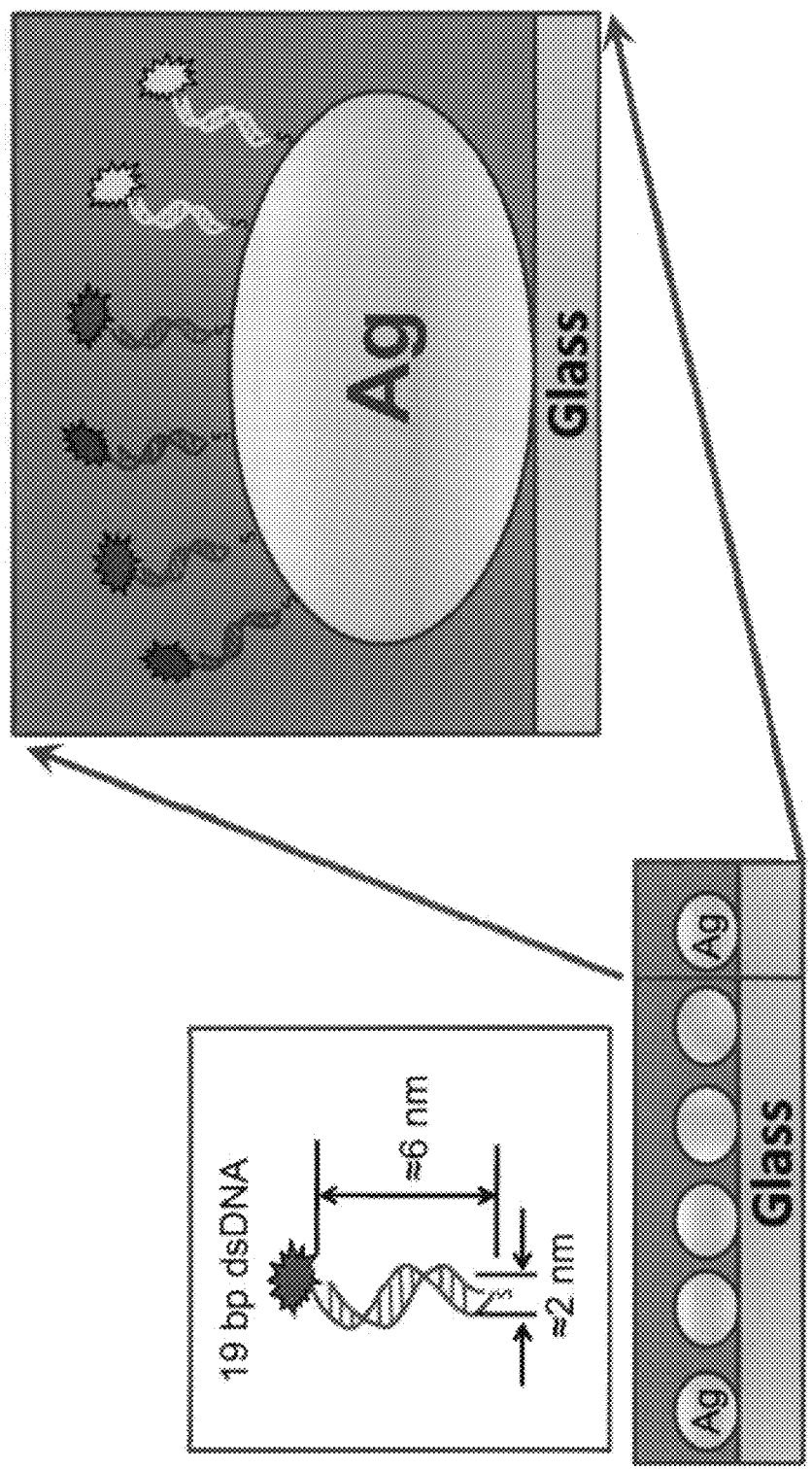
FIG. 7 shows the calculation of the DNA density and average distance between dsDNA molecules on SiFs. Density (D) of dsDNA on SiF is D=0.02 pmole (DNA)/mm$^2$ (SiF) or D=0.012 molecules/nm$^2$. An average distance between DNA molecules on SiFs is 6-9 nm at saturation conditions.

To estimate quantitatively the maximum density of DNA on the SiF-surface we performed a titration of the preformed anchor-DNA surface (the thiolated anchor-DNA (A1) was pre-incubated on SiF for 1 hour, which corresponds to the saturation condition, see FIG. 3) with the Alexa 488 labeled probe-DNA (P1). For each concentration of probe-DNA MW-accelerated hybridization was applied to rapidly anneal duplexes. Unhybridized DNA molecules, in excess of probe-DNA, were removed by washing the wells with buffer. The titration results are shown in FIG. 6. At the beginning of the titration, the fluorescence signal, measured from the well bottom, increases almost linearly with an increase in probe-DNA. This dependence sharply plateau's at the concentration [probe-DNA]=10 nM, defining the saturation of the system. Assuming that in this condition the concentration of probe- and anchor-DNA are equal, [anchor-DNA]=[probe-DNA], and taking into account the dimensions of the SiF surface, one can easily calculate the density (D) of the attached DNA: D=0.02 pmole (DNA)/mm$^2$ (SiF), which ultimately corresponds to D=0.012 molecules/nm$^2$. Subsequently, the average distance between DNA molecules on the SiF-surface is 6-9 nm, at saturation conditions, as shown in FIG. 7. The maximum value of density and minimum distance between duplexes on the surface are in good agreement with the geometrical sizes of DNA (diameter of dsDNA is about 2 nm, the length of 19 bp fragment is ≈6 nm) and DNA properties. The electrostatic repulsion between two highly charged polyanion molecules, such as dsDNAs, and the spacial flexibility of the DNA fragments, which are attached to the silver surface through the flexible SH—($CH_2$)$_6$-5'-DNA bridge, ultimately limits this spacing distance and, correspondingly, the density of DNA molecules on the SiFs.

The estimated distance of 6-9 nm between fluorophore-labeled DNA molecules is quite short at the saturation condition and, subsequently, has the potential to cause fluorescence resonance energy transfer (FRET)[33,34] between adjacent chromophores. FRET between chromophores on the surface is indeed undesirable for any multi-color quantitation assays, because it effectively decreases sensitivity of one or more of the assays and would likely induce non-linear dependences of the measured signal upon actual amount of analyzed DNA.

The absorption and fluorescence spectra of fluorophores used in this testing are partially overlapped and thus can form FRET donor-acceptor pairs, FIG. 13. The Forster distance for these pairs varies from Ro=6.0 nm (donor—Alexa 488; acceptor—Alexa 594) to 7.1 nm (Alexa 546; Alexa 594), i.e. comparable with the estimated distance between chromophores-DNA on surface at the saturation condition. Analysis of the fluorescence spectra of the donor-acceptor pair (Alexa 488 and Alexa 546; Ro=6.4 nm), shown in FIG. 14, clearly shows that at the saturation condition, the FRET efficiency between this pair is close to 50%, which corresponds to an average distance between them of 6-7 nm and, subsequently, is close to our inter-DNA distance estimates.

Figure 15:
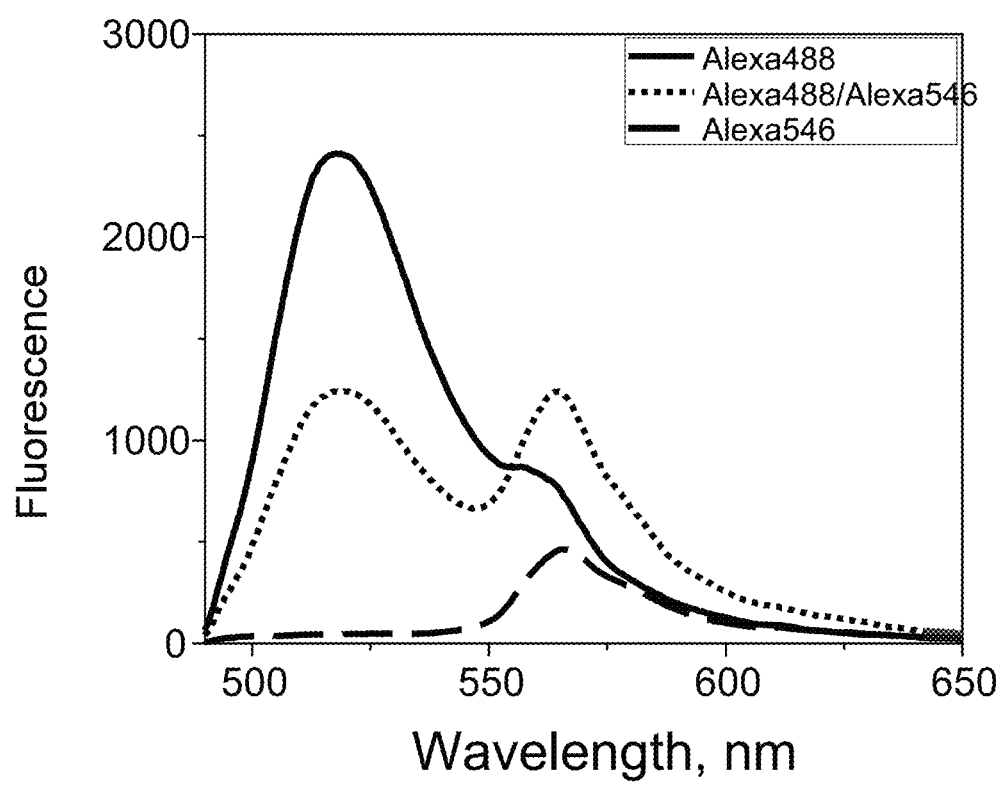

Fortunately, the density of DNA on the surface, and consequently the distance between labeled DNAs, can be easily regulated using different incubation times of the thiolated anchor-DNA on a SiF surface (FIG. 3). It has been found herein that increasing the inter-DNA distance to >9 nm (incubation time <60 minutes) almost fully eliminated FRET between the fluorophores, as shown in FIG. 15, subsequently, returning the fluorescence signal to a linear dependence, as a function of probe-DNA, as discussed below.

Proportionality Between Fluorescence Signal and Probe/Anchor DNA Ratio.

Figure 8:
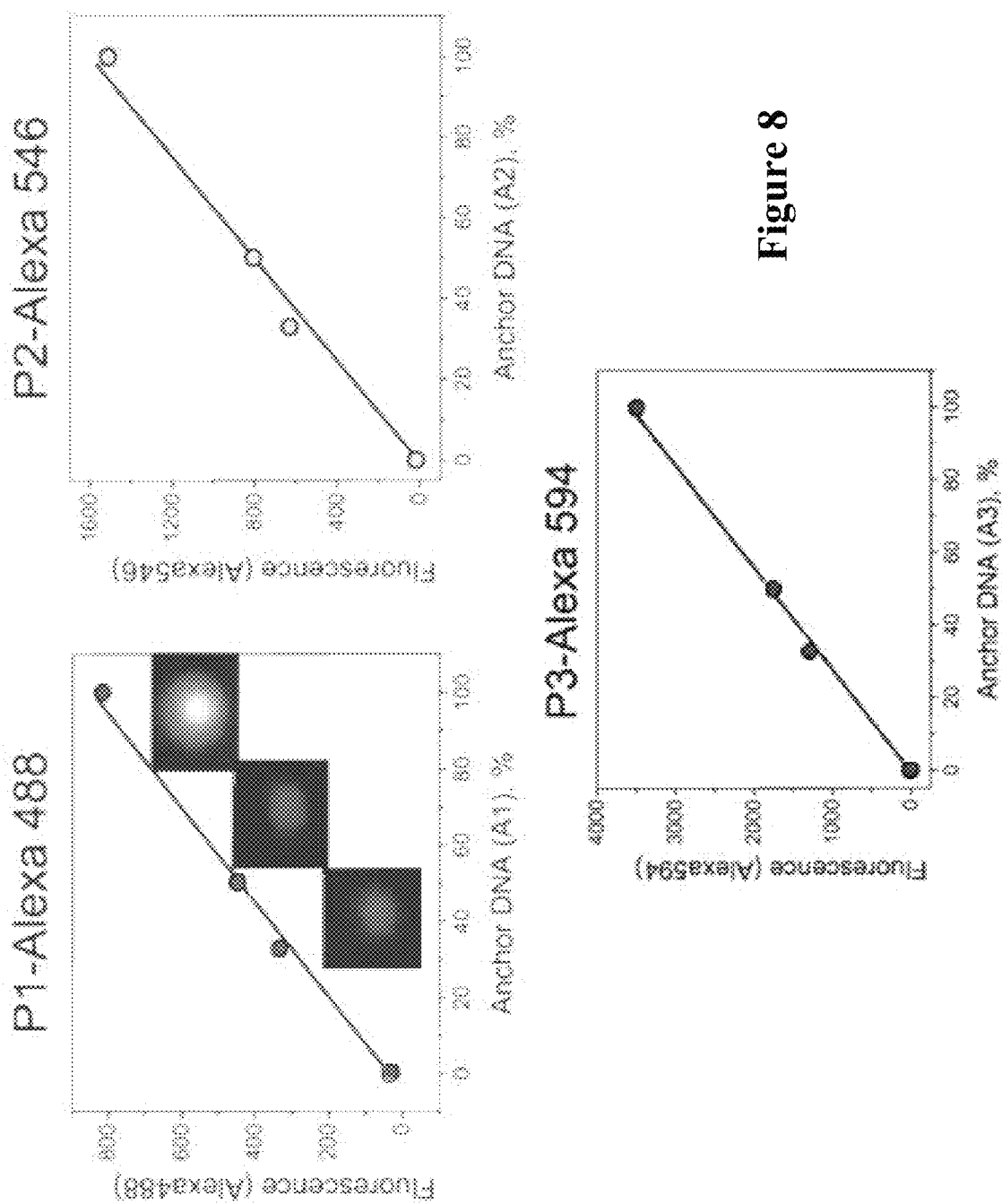
FIG. 8 shows the fluorescence signal from annealed ($P_n/A_n$)-DNA duplexes is proportional to the concentration of complementary Anchor-DNA ($A_n$) on the silver surface (SiFs). Anchor-DNA ($A_n$), complementary to the Probe-ssDNA sequence ($P_n$), was attached to the SiFs surface by loading solutions containing 100% of complementary $A_n$ or a mixture (mol/mol) of $A_n$ with other (non-complementary) Anchor-DNAs at ratios: 1:1 ([$A_n$]=50%), 1:1:1 ([$A_n$]=33%). A blank (buffer) solution was used as a control. The concentration of labeled probe-DNA (P1, P2 and P3) loaded into wells was 1 µM. Insert: shows photographs of the wells, containing annealed ($A_1/P_1$)-duplexes, correspond to the following ratios of the complementary Anchor-DNA ($A_1$) concentration to the total concentration of DNA duplexes: 100, 50 and 33%. Wavelength of excitation was 473 nm.

It is clear that there are several key conditions to enable DNA quantitation from the surface: (1) the linear dependence between fluorescence signal and probe-DNA concentration, and (2) no hybridization with different anchor-DNA, attached to the SiF-surface, with complementary fluorescently labeled DNA probes. To analyze these properties of the DNA-RCS system, the anchor-DNA ($A_n$), complementary to the probe-DNA sequence ($P_n$), was attached to the SiF surface (incubation time 30 min) by loading solutions containing 100% of complementary An or a mixture (mol/mol) of An with other (non-complementary) anchor-DNAs at the following ratios: 1:1 ([An]=50%) and 1:1:1 ([An]=33%). The concentration of probe-DNA (P1, P2 or P3) in solution was constant, [Pn]=1 µM. FIG. 8, Left, Center and Right, shows the dependence of fluorescence of the three reporter dyes (green, yellow and red), the fluorescence of which corresponds to the three different DNA sequences, upon the relative content (fraction) of complementary anchor-DNA ($A_n$) on a SiF-surface, i.e. $f_{An}=[A_n/\Sigma A_n]\times 100\%$. For all three probe-DNAs, loaded on a DNA-scaffold surface, fluorescence linearly depends on the fraction of complementary DNA ($f_{An}$). Real-color photographs of the wells, containing annealed (A1/P1)-duplexes, corresponding to the $f_{An}$=100, 50 and 33%, are shown in FIG. 8 (Left), clearly demonstrating the progressive change in brightness, which is proportional to the fraction of annealed DNA on the surface.

It may be concluded that the attachment of thiolated anchor DNA molecules to a silvered surface is proportional to their respective fraction in the loading solution, i.e. attachment does not depend on DNA sequence and DNA molecules distributed randomly along the surface. Then, hybridization of complementary DNAs on a DNA-activated surface is independent on the presence of non-complementary DNAs, and proportional only to the concentration of certain complementary anchor-DNA.

Photostability of the Reporter Chromophores.

Fluorophores usually have limited stability to light, i.e. they photobleach. Photobleaching is a process of photochemical dye modification which ultimately results in the disappearance of the fluorescence properties of the fluorophore. In particular, the rate of photobleaching is strongly underpinned by the excited state lifetime of a chromophore, i.e. the time during which the chromophore can undergo photochemical destruction or transformation. The metal-enhanced fluorescence (MEF) effect generally decreases the excited state lifetime of chromophores due to coupling and energy exchange between electronic states of a dye and nanoparticle (NP) plasmons[16,35]. In the case of the presently discussed DNA-RCS assay, reporter fluorophores are in close proximity to silver NPs, are therefore coupled and an intensive MEF effect is observed.

Figure 9:
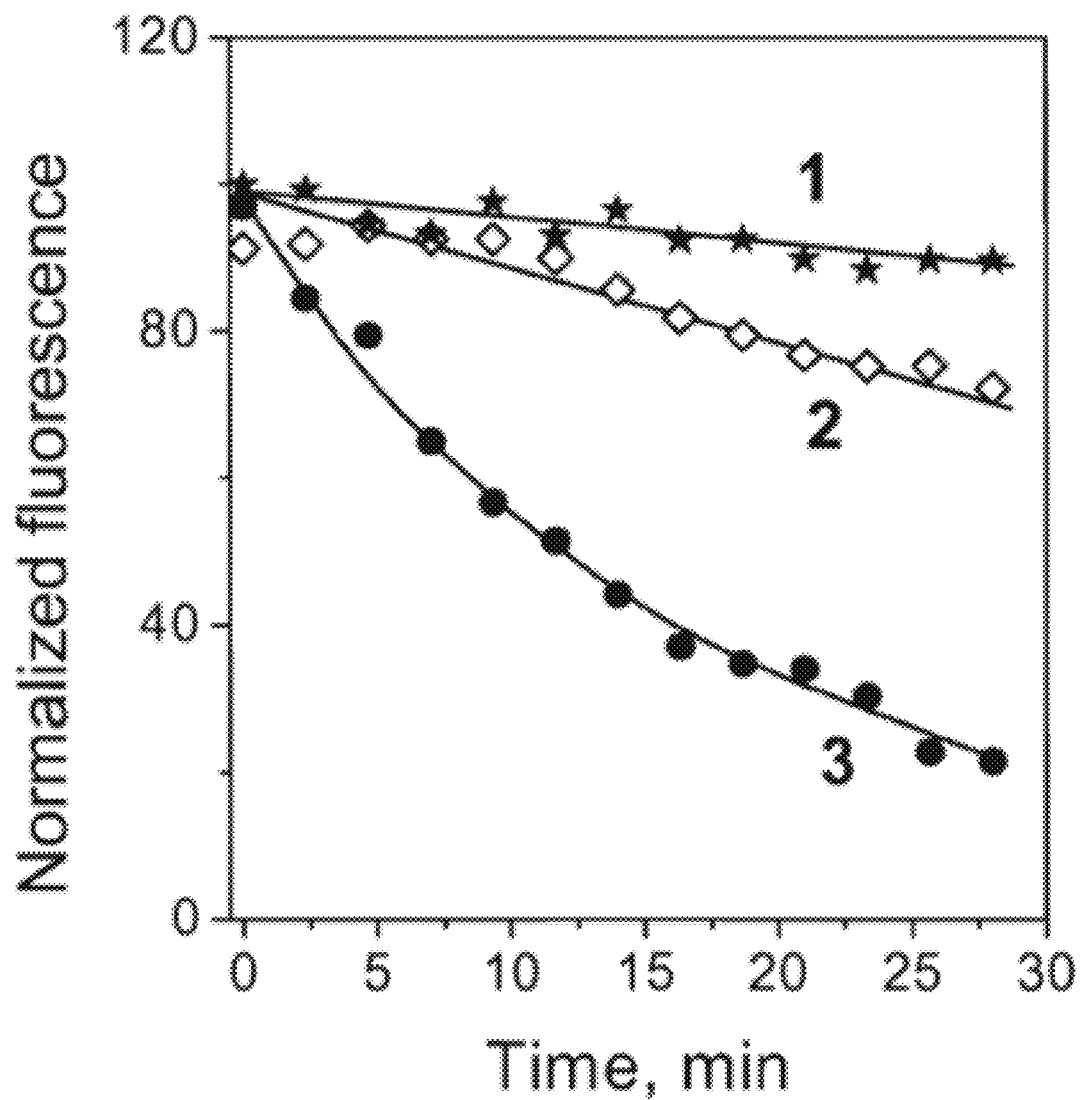
FIG. 9 shows photobleaching profiles of free Alexa546-ssDNA on glass (3) and on SiF (2), and Alexa546-dsDNA attached to SiFs (1). Laser power—5 mW. Excitation—532 nm.

The photobleaching profiles of free Alexa 546-ssDNA solution loaded on glass (control sample) and on a SIF-slide are shown in FIG. 9. Also in FIG. 9, the profile of photobleaching for Alexa 546-dsDNA-SiF, i.e. attached to the SiF-surface, is shown. To compare the rates of photobleaching, the data were normalized to 1.0 at zero time (FIG. 9). One can readily see that the rate of photobleaching of Alexa 546-dsDNA-SiFs is significantly lower than on glass or a simple solution on SiFs. This result is highly consistent with the MEF phenomenon, i.e. an increase in brightness coupled with a simultaneous drop in chromophore excited-state lifetime[11,16,22,35]. Accordingly, chromophores with a reduced excited state lifetime are more resistant to photo oxidation or other excited state processes, which influence the fluorophore stability and observed intensity. Undoubtedly, the observed large increase of reporter dye photostability has a very positive impact on the utilization of the DNA-RCS technology in the biosciences and medicine, where assay photostability is a primary concern.

Estimation of the MEF Effect for DNA Reporter Dyes Attached to a SIFs-Surface.

Figure 10:
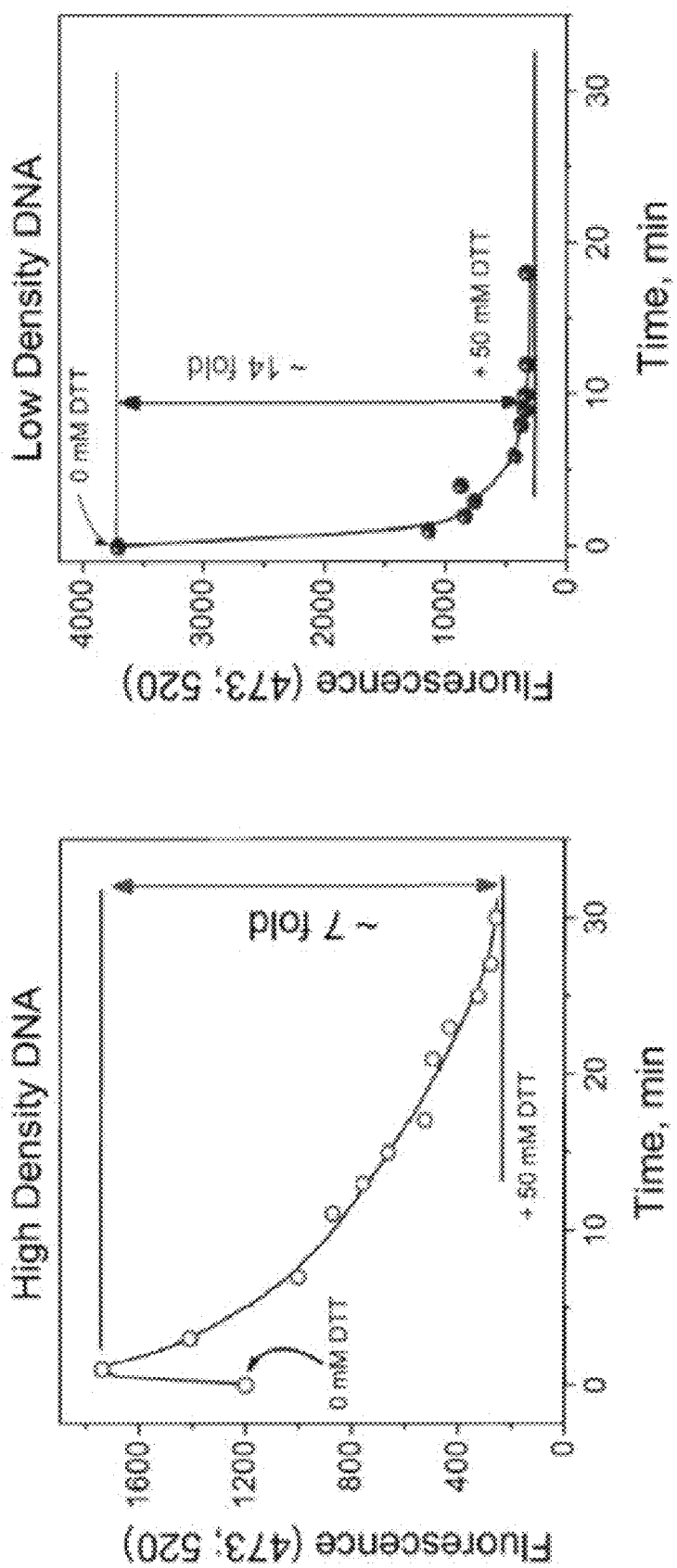
FIG. 10 shows the kinetics of dissociation of the DNA duplexes (DNA-Alexa 488/DNA-Alexa 546=1:1) from SiFs in the presence of 50 mM DTT. Fluorescence was excited at 473 nm and measured at 520 nm. The intensity of fluorescence at zero time was measured for a solution without DTT.
Figure 14:
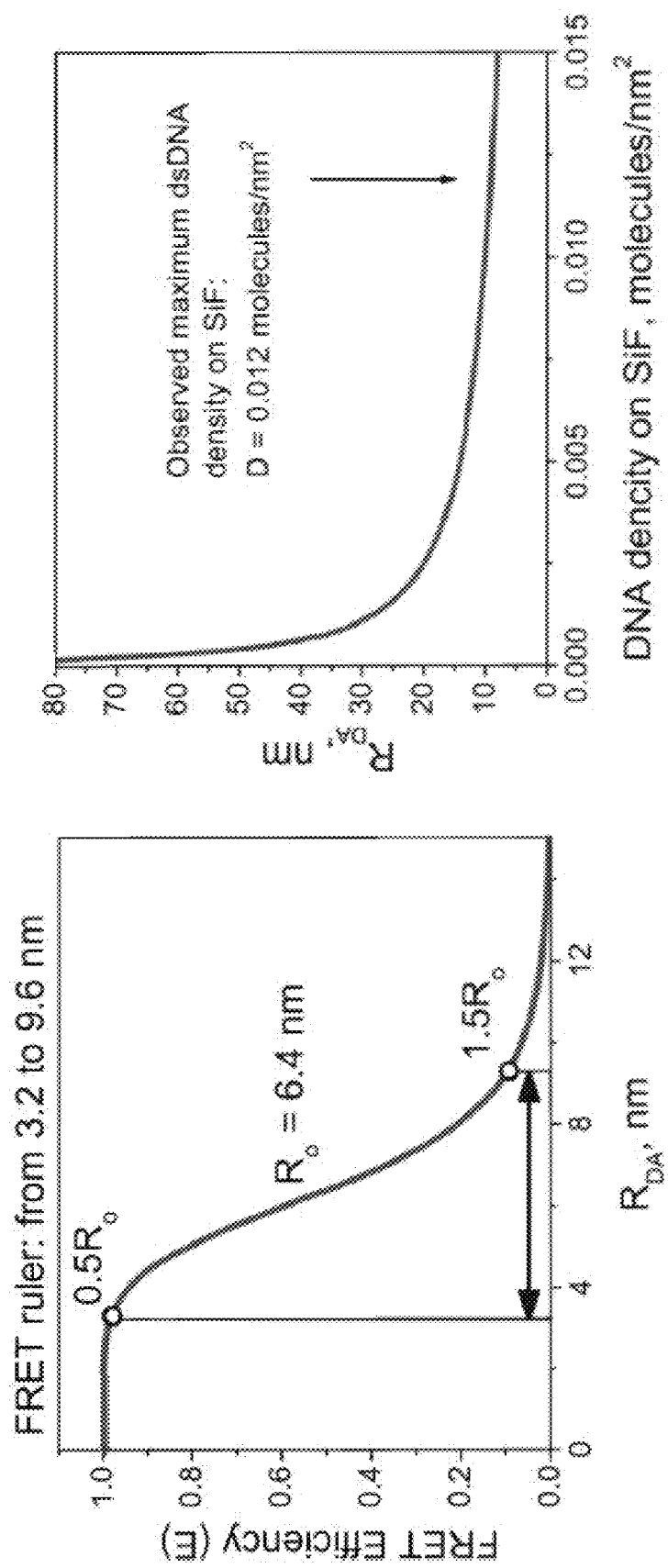
FIG. 14 (Left) shows FRET efficiency upon distance between the donor and acceptor, Alexa 488 and Alexa 546, ($R_o$=6.4 nm). (Right) shows the dependence of an average distance between dsDNA upon the density of DNA on SiF surface: R=SQRT(1/N0.istance of an average FIG. 15 shows the fluorescence spectra of the labeled dsDNAs attached to the silver surface (SiFs): Alexa 488—100% of dsDNA, labeled with Alexa 488, attached to SiFs; Alexa 546—100% of dsDNA-Alexa 546 attached to SiFs; Alexa 488/Alexa 546—an equimolar mixture: 50% of dsDNA-Alexa 488 and 50% of dsDNA-Alexa564, attached to SiFs. Incubation time of DNA in SiF-wells was 1 hour. Excitation was 473 nm. The FRET efficiency is E=1−FDA/FD≈0.5. If Ro=6.4 nm, then RDA=(1−E)/E*(Ro)1/6≈6.4 nm. i.e. an average distance between labeled DNA duplexes is about 6-7 nm as it was estimated for the saturation condition.

In the presently discussed assay scaffolds, thiolated DNA is attached to silver NPs through the thiol-group and subsequently upon competition with dithioreitol (DTT), it can be released into a bulk solution, i.e. the distance from chromophore to SiF will be increased, which will ultimately lead to a decrease in MEF. Kinetics of dissociation of the DNA duplexes (DNA-Alexa 488/DNA-Alexa 546=1:1) from SiF-surface in the presence of 50 mM DTT are shown in FIG. 10, Left and Right. In one case (FIG. 10, Left) the density of DNA on the surface was high (saturated condition), in the 2$^{nd}$ case (FIG. 10, Right)—low density. Remarkably, the change in fluorescence upon addition of DTT shown in FIG. 10 (left) increases initially and then drops down by about 7-fold. As shown herein, at the saturation condition the distance between chromophores (Alexa 488/546) is close to the Forster distance and FRET decreases the fluorescence intensity of Alexa 488 almost twice (FIG. 14). Subsequently, dissociation of the DNAs from the SiF surface decreases the FRET efficiency and one can Observe a further increase in fluorescence. In contrast, at low DNA density, a sharp drop in fluorescence signal is observed from the onset of the DTT-induced dissociation of DNA. In this case, the total drop of in intensity is $\approx$14-fold, almost twice higher as compared to the high DNA density case. Actually, one can consider this change as a true decrease of the MEF effect upon DNA dissociation. It is known that relative to a glass control sample, the MEF effect on SiFs could be about 20-25[36]. Here it was measured MEF$\approx$14 for the dye relative to SiFs. This suggests that the total MEF for a dye attached by DNA to SiFs relative to glass (control sample) could be calculated as MEF$\approx$14$\times$20=280, which is highly consistent with the general theory of metal-enhanced fluorescence[35].

Characterization of DNA Hybridization on SiF Surface

Attachment of anchor DNA to a SiF surface forms a DNA scaffold around the NPs, which can effectively catch a complementary fluorophore-labeled DNA, target DNA, and form double-stranded DNA. Upon the process of hybridization, the observed fluorescence intensity is linearly proportional to the amount of the chromophore-labeled target DNA that forms a duplex with an anchor DNA. The amount of hybridized duplex molecules is limited by the quantity of the target DNA, but cannot exceed the amount of the anchor DNA on the SiF-DNA scaffold. Therefore, the observed fluorescence intensity is limited and upon annealing, approaches saturation. Subsequently by measuring the fluorescence of the target DNA one can register kinetics of the annealing and estimate the percentage of hybridized DNA. FIG. 16 shows kinetics of hybridization of target DNA with an anchor DNA scaffold both with and without microwave irradiation. Remarkably, the hybridization of DNA proceeds almost immediately (<30 s) with microwave irradiation (MW) and, in the absence of microwave "heating", it takes almost 1 h to approach the same level of fluorescence signal. Subsequently, MW acceleration dramatically (~1000-fold) speeds up the kinetic process and, thus, shortens the time of the macromolecular recognition, which indeed is a critical factor for creation of fast bio-assays. The slow kinetics of duplex formation at ambient temperature are simply explained by: quite slow diffusion of the target DNA from the solution to the DNA scaffold, formed on the silvered surface, and by competition between inter- and intra-molecular interactions (it is well known that single stranded DNA can form intra-molecular structures at room temperature[26]. These two processes may significantly increase the time of hybridization[17, 28, 24]. The true nature of the MW effect on kinetic parameters of DNA annealing is not fully clear today, and it is assumed that MW irradiation influences both processes, i.e. rate of diffusion and competitive intermolecular recognition[28]. It is known that MW irradiation, by interacting with a dipole moment of water molecules, increases the rate of this movement and subsequently enhances molecular thermodynamic temperature. Silver NPs, immobilized on a glass surface, cannot move and electrons, trapped in a small (100-300 nm) particle volume, as compared to MW radiation wavelength, are outside of the resonance condition and, consequently, could not absorb MW energy. (It should be noted that silver electrons (plasmons) in nanoparticles of that size can effectively absorb light[16], with a maximum at ~400 nm, which is far away from the MW wavelength of ~12 cm.) Therefore intuitively, pulses of MW radiation applied to the reacting system, induce a rapid temperature gradient between the "cold" SiF surface and a solvent that would stimulate the rapid movement of molecules, due to mass transport and/or increased molecular diffusion within the wells. Interestingly, the total temperature of the solution in the wells does not sufficiently increase in this condition (see FIG. 19). Another factor, which MW can provoke, is destabilization of intra-molecular structures in ssDNA, by disordering the hydration of the DNA polymer, which plays a significant role in stabilization of the DNA molecule conformation[31, 32], and by increasing internal DNA strand flexibility. This ultimately accelerates specific inter-molecular hybridization.

Characterization of the 2-Color DNA Assay

The 2-color DNA assay is based on both the detection and registration of two color emissions, which correspond to two different target DNAs, which ultimately could be any DNA of interest. To reach good discrimination between the two different specific DNA sequences by means of color measurement we have used Alexa 488 and Alexa 594 dyes. Both dyes have large extinction coefficients (71,000 and 90,000 M−1 cm−1, respectively), high brightness (quantum yield of the free dyes in aqueous solution—0.92 and 0.66, respectively) and emit light within different spectral regions: Alexa 488 is a green (520 nm) and Alexa 594 is an orange-red (620 nm) fluorescent chromophore, therefore their fluorescence spectral overlap is insignificant, as shown in FIG. 20.

FIG. 17 shows emission spectra collected from the SiF bottom well after hybridization of the anchor DNA, attached to NPs, with the green target DNA. It should be noted that in all cases hybridization was accelerated by the 30 s MW irradiation at 20% low power. The real-color photograph shows a green spot of high intensity, corresponding to the emission spectrum, shown in FIG. 17, insert. A strong fluorescence signal, taken from the mono-layer of the DNA scaffold, demonstrates the high sensitivity of the "Rapid Catch and Signal" (RCS) assay. Taking into account geometrical sizes of dsDNA, one can estimate the maximum density of dsDNA on the SiF surface, which is about (0.02 pmol DNA)/mm$^2$, i.e. quite a small amount. Meanwhile the fluorescence signal is strong due to the MEF effect and can be easily registered using fiber optic instrumentation. After hybridization with 19 base anchor DNAs, the distance of Alexa 488 dye, attached to the 5'-end of a target DNA, to silver NPs is about 7 nm. At this distance a strong coupling between chromophore and NP plasmons occurs and the expected enhancement of emission can be more than 100-fold[23, 22, 16]. A similar result was obtained with the red target DNA sequence, also hybridized with the corresponding complement of any anchor DNA SiF-wells, as shown in FIG. 17b. A real-color photograph (FIG. 17b, insert) shows a bright red fluorescent spot excited by the 594 nm CW laser line.

The Metal-Enhanced Fluorescence effect[23, 22, 16], which underpins the 2-color ultra-high sensitivity DNA assay, also affords for a decrease in the excited state lifetime and, consequently, an increase in chromophore photostability[11, 22,38,39]. The nature of the lifetime decrease upon MEF is thought to be due to energy transfer from an excited state dipole of a chromophore to induce NP plasmons, due to near-field coupling between them[23, 16], followed by surface plasmon emission of the coupled quanta[16, 23, 22, 38]. Subsequently, chromophores with a reduced excited state lifetime are more resistant to photo-oxidation or other excited state processes, which ultimately influence fluorophore stability and the observed intensity over time. The intensity decay functions of the chromophores (Alexa 488 and Alexa 594) was measured, attached to DNA in solution and in the SiF/DNA complex, as shown in FIG. 18, and Table 2. The observed decay functions for both chromophores clearly show a drop in the observed lifetime on SiFs, as compared to solution. The results correlate well with the enhanced photostability of the dyes, as shown in FIG. 21. This result suggests a significant advantage of employing short (~20 base) DNA fragments, attached to a silver NP surface, for achieving both strong MEF and photostability of fluorescent labels and, ultimately, in establishing an ultra-high sensitive and non-photobleached fluorescence-based DNA quantitation assay.

TABLE 2

Fluorescence intensity decay parameters for Alexa 488 and Alexa 594 dyes attached to DNA, bound to SiF, and free in solution

| Sample | $\tau_1$, ns | $\alpha_1$ % | $\tau_2$, ns | $\alpha_2$ % | $<\tau>$, ns | $\tau$, ns | $\chi^2$ |
|---|---|---|---|---|---|---|---|
| (a) Alexa 488 in cuvette | 4.80 | 61 | 2.63 | 39 | 3.95 | 4.23 | 1.049 |
| (b) Alexa 488 on vSiFs | 3.29 | 6 | 0.12 | 94 | 0.32 | 2.13 | 2.034 |
| (a) Alexa 594 in cuvette | 4.45 | 78 | 3.20 | 22 | 4.17 | 4.23 | 1.056 |
| (b) Alexa 594 in SiFs | 2.07 | 7 | 0.14 | 93 | 0.27 | 1.156 | 1.811 |

$<\tau>$—amplitude-weighted lifetime; $\tau$—mean lifetime.

The 2-color DNA assay employs a mixture of two types of anchor DNA on one surface with the "catching and signaling" of two different target DNAs. This system is quite complex and there are, at least, two conditions at which the 2-color DNA quantitation assay needs to be optimized: a) homogeneous covering of the silver surface with DNA that does not depend on the type of DNA fragments, i.e. the ratio of different DNA fragments in solution and on the surface should be the same; b) the density of DNA on SiFs should be low enough to prevent energy migration (FRET) between labeled DNA molecules, which otherwise would result in selective quenching of one reporting chromophore and enhanced emission of the other. A system was studied, when both anchor DNAs, complementary to the green and red target DNAs, were mixed at 1/1 mol/mol ratio and incubated on SiF-slides, to get equimolar amounts of 2-anchor DNAs surface. The prepared mixed-scaffold DNA was then hybridized with an equimolar mixture of the two target DNAs and the fluorescence from the wells was analyzed. FIG. 17 and b show the fluorescence spectra collected from the wells. Emission was excited using 473 and 594 nm laser lines, respectively. It is notable and indeed encouraging that the intensity of fluorescence in both cases was 50% of the intensity taken from each well, containing only one kind of anchor DNA, recalling that the DNA was mixed in a 1/1 ratio. This result clearly shows that a) the attachment of two different thiolated anchor DNAs to silver NPs is proportional to the ratio of molecules in the loading solution; b) hybridization of a target DNA to its complement is highly sequence-specific and c) finally that no FRET occurs between the Alexa 488 and Alexa 594 dyes, which is strongly suggested by the measured ratio of fluorescence intensities (i.e. 50% in our case). For the pair of Alexa fluorophores used, the Forster distance is Ro=6 nm, and subsequently it can be intuitively suggested that the average distance between labeled DNA on the silver surface is therefore larger than 6 nm.

Benefits of the Rapid Catch and Signal Technology

The platform technology has many significant benefits, including: that two DNA targets can be detected within 30 s. The 2-target DNA assay can use any 2-color fluorophores, where the best results will be obtained for the condition where little to no spectral overlap occurs. The Rapid Catch and Signal (RCS) technology can target any genome of interest by using specific DNAs as anchor-probes, which encode for the specific genome of interest. Notably the assays are highly photostable, considerably more so then in the absence of silver. This ultimately allows for the collection of data over much longer times than is traditionally used.

The new RCS technology is suitable to be used in conjunction with previously reported rapid (<15 s) bacteria lysing strategies[25], suggesting that DNA from organisms can now be lysed, detected and quantified in a 2-plex embodiment, with a total measurement time of less than 1 min. This "Rapid Catch and Signal" technology could also significantly improve sensitivity and specificity of chip-based assays, e.g. oligonucleotide microarrays (DNA chip)-based hybridization analysis[37], which are widely used nowadays for analysis of all possible mutations and sequence variations in genomic DNA.

The "Rapid Catch and Signal" RCS technology has been applied to a 2-color DNA assay, which shows high sensitivity, sequence specificity and DNA quantitation ability. The DNA scaffold formed on the SiFs is proportional to anchor DNAs fragment molar concentration ratio in the loading solution. The density of double-stranded DNAs on the silver surface is sufficiently low enough to avoid intermolecular energy transfer (FRET) between labels (Alexa 488 and Alexa 594), i.e. an average distance between duplexes >6 nm (Förster distance for the donor (Alexa 488)-acceptor (Alexa 594) pair is 6 nm). "Catching" of the complementary target DNAs using the DNA scaffold on a surface is sequence-specific. The results shown herein clearly show that the 2-color DNA assay can effectively be employed as a new "Rapid Catch and Signal" technological platform in the creation of an ultra-sensitive, sequence-specific approach for the fast analysis of genetic material from different organisms, for potential analysis of bacteria and virus pathogens, and search for possible mutations and sequence variations. This technology being fast, ultra-sensitive and inexpensive can effectively compete with the PCR technique, especially for the routine and rapid analysis in Point-of-Care settings and bio-medical laboratories.

Labeling of Five Different Sequences

In the present example five different fluorescent dyes to label five different DNA sequences (FIG. 22) the optical parameters of which are shown in Table 3, absorption and fluorescence spectra are presented in FIGS. 30 and 31.

TABLE 3

Lasers used for excitation of the Alexa-DNAs fluorescence and chromophore relative brightness.

| DNA labels | Excitation Laser line ($\lambda_{ex}$), nm | Dye brightness at $\lambda_{ex}$ ($\epsilon \times \phi$, $10^{-3}$ $M^{-1}cm^{-1}$) |
|---|---|---|
| Alexa 488 | 473 | 33 |
| Alexa 514 |  | 12 |
| Alexa 546 | 532 | 43 |
| Alexa 594 |  | 13 |
| Alexa 647 | 633 | 44 |

Dye brightness calculated for different wavelengths, corresponding to the laser excitation wavelength; $\epsilon$ and $\phi$ are molar extinction coefficient and quantum yield of the chromophore, respectively.

The brightness of the selected dyes is large and is in the range of 12-44 $M^{-1}cm^{-1}$, which makes them highly suitable for the anchor-DNA/probe-DNA hybridization sensing.

Real-color photograph of the anchor-DNA scaffold attached to a SiF-glass slide is shown in FIG. 23. Thin silver layer, consisting of metal nanoparticles, changes color upon conjugation with thiolated DNA. This color effect can be used as an indication of a DNA-SiF conjugation. Such DNA/SiF slides, but prepared using different DNA sequences and their different mol/mol mixtures, were used in this study.

It is especially important for the system in which DNA partners are physically separated, i.e. anchor-DNA strand is attached to the well surface while complementary DNA strand is in solution above the surface. In microwave field the process of DNA hybridization in wells significantly speeds up, the time of annealing decreases from hours to few seconds[18].

Another principle that has been utilized in this example is metal-enhanced fluorescence (MEF). The length of DNA fragments employed in the assay was specially designed to keep signaling chromophores on a short leash, ~6 nm, as shown in FIG. 32, from a silver film surface, ensuring the largest enhancement (MEF) of their fluorescence response[17, 18] and, consequently, high sensitivity of DNA detection, which is extremely important for the development of highly sensitive multiplexed DNA detection assay.

FIG. 24 (a) shows an example of recorded fluorescence spectra of labeled probe-DNA hybridized with the anchor-DNA/SiF surface. The total amount of anchor-DNA, complementary+non-complementary, was constant. The fractional amount of the complementary anchor-DNA loaded on SiF was varied from 100 to 20%. After hybridization of the specific Alexa 647-probe-DNA with anchor-DNA scaffold the fluorescence spectra intensity follows the concentration of complementary DNA on SiF. FIG. 24 (b) shows similar result for another probe-DNA sequence, which was labeled with Alexa 514. The obtained linear dependences of hybridized DNA upon the fractional amount of complementary anchor-DNAs on the surface demonstrates that attachment of different DNA sequences to SiF is independent and proportional to their relative concentrations in loading solutions and, respectively, on SiF surface.

Subsequently, with increase in a number of analyzed DNA sequences in one well the fluorescence signal exponentially decreases for all analyzed DNAs, as shown in FIG. 25. This result also assumes that DNA hybridization ("catch") on a surface is highly specific. FIG. 26 shows the result of study of cross-selectivity in DNA/DNA molecular recognition/hybridization. In this experiment hybridization was accelerated by using microwave irradiation of wells in microwave cavity. For the five different DNA sequences, attached to the SiF-surface, the molecular recognition was highly selective. The sequence specific anchor/probe DNA hybridization have shown a high value of the cross-selectivity >98%. This result is important for the development of the multi-color one-well assay justifying its ability to detect independently different DNA sequences in one well.

The optical properties of the dyes undergo significant change upon probe-DNA attachment to the SiF-surface. In particular, in bound to SiF state, as compared to the bulk solution, their fluorescence lifetime dramatically decreases from nanoseconds to picoseconds (FIG. 27) while emission intensity significantly enhances due to the metal-enhanced fluorescence (MEF) effect[16, 22]. The important consequence of the fluorescence excited state lifetime reduction is an increase in dyes photostability since the fluorophore is less prone to photo-oxidation or other excited state processes, which is demonstrated in FIG. 28 by the profiles of a sensor dye photobleaching during irradiation (Alexa-546)-DNA attached to SiFs and free on glass. Enhanced photostability of dyes plays an important role in maintaining sensitivity, reliability and repeatability of the assay.

FIG. 29 a-c shows fluorescence spectra collected from one well containing five different DNA sequences annealed with labeled complementary target probe-DNAs. Five types of DNA were attached to a silver film in equimolar ratio and, subsequently, five different fluorophores were evenly distributed on SiF well bottom. Fluorescence signal from a well was collected using three excitation wavelengths: 473, 532 and 633 nm, corresponding to absorption spectra of the dyes, as shown in FIG. 30. FIG. 29 (a) shows fluorescence spectra of two labeled probe-DNAs (P1 and P2, see FIG. 22, DNA/Alexa-488 and DNA/Alexa-514. Fluorescence was excited using 473 nm laser line. Notably, no other DNA labels contribute to the observed fluorescence. Upon excitation at 532 nm another two labeled probe-DNAs (P3 and P4) signal about hybridization event: DNA/Alexa-546 and DNA/Alexa-594. Hybridization of the fifth DNA sequence (P5), labeled with Alexa-633, can be solely "visualized" using excitation wavelength of 633 nm. Consequently, on first step using three excitation wavelengths and measuring/observing visible light signal (color) one can distinguish three sets of DNA sequences: Set I=(P1+P2), Set II=(P3+P4) and Set III=P5. First and second sets potentially can contain two different DNA sequences.

Further analysis can be applied to separate contribution of individual DNA sequences to Set I and II. For that purpose observed fluorescence spectra can be deconvoluted onto two components by the fitting procedure using the following equation:

$$S_{obs}(\lambda)=A_1 \times S_1(\lambda)+A_2 \times S_2(\lambda), \quad (3)$$

where $S_{obs}(\lambda)$, $S_1(\lambda)$ and $S_2(\lambda)$ are observed fluorescence spectra and standard fluorescence spectra measured for separate components, $S_{obs}(\lambda)$ is normalized in maximum to 1.0; $A_1$ and $A_2$ are fractional contribution of the components to the observed spectrum.

FIGS. 29 (a) and (b) shows the results of fitting for DNA's Set I and Set II. The best fit gives the following contributions of components to the observed spectra, Set I: $A1/A2=F_{max}$(Alexa-488)/$F_{max}$(Alexa-514)=0.57/0.43; Set II: $A1/A2=F_{max}$(Alexa-546)/$F_{max}$(Alexa-594)=0.80/0.20, $F_{max}$ is a maximum fluorescence intensity (FIG. 29). This result was obtained for the case when all DNA sequences are hybridized in equimolar ratio to the DNA scaffold. The change in ratio (A1/A2) will be an indication of the change in amount of analyzed target DNA in solution. For example when one DNA sequence in a Set is absent it will be indicated in A1, A2 values, i.e. A1=1, A2=0 or vise versa, depending on sequence.

In this example, it has been shown that using simplified 2-piece DNA model (FIG. 1) to investigate characteristics and spectral properties of the developed multiplexed DNA detection assay, which based on DNA-RCS technology, i.e. "Rapid Catch and Signal".

For the purpose of DNA detection in real samples the 3-piece DNA system will be used, as shown in FIG. 33. It consists of anchor-DNA that forms scaffold on silver film surface, labeled probe-DNA and target DNA sequence, which is a fragment of DNA of interest, in particular, it can be a fragment of the genomic DNA. Both anchor- and probe-DNAs are designed to be complementary to the specific genome sequence for the purpose of highly selective specificity of recognition/hybridization, which accords with the principle of DNA primers designing for PCR.

Shown herein is a highly sensitive and selective multiplexed DNA detection assay that is used to detect five different DNA sequences in one sample in one well. DNA-RCS technology used in developing this assay employs principles of microwave-accelerated intermolecular recognition and metal-enhanced fluorescence. The main advantage of the developed multiplexed five-color DNA assay is ability to detect five different DNA sequences without neighboring effect, i.e. showing high degree of cross-selectivity, >98%, which is especially important for multiplexing DNA detection approach on surface where the density of DNA scaffold is high.

The technology described herein can be used to detect one or more simultaneous food pathogens, clinical agents, biowarfare agents, blood-borne pathogens, epidemiological infections, such as MRA, MRSA, agricultural/crop pathogens, environmental contaminates, plant pathogens, fungi, aqueous marine pathogens, diseases or contaminants.

The technology of the present invention will work for sample volumes ranging from nanoliters to many milliliters, i.e. 1 nL to 25 mL. The technology can be used with a variety of sample types, including but not limited to: blood, serum, clinical swabs, nasal swabs, rectal swabs, vaginal swabs, penile swabs, mucus, ear wax, tears, sweat, CSF, sputum, Buffy Coats, environmental waste waters, drinking water, ground water, river water, ocean water, beverages, food materials, such as eggs, testing of hair, skin and open wounds for sepsis.

REFERENCES

The contents of all references cited herein are hereby incorporated by reference herein for all purposes.
1. Caraway, N. P.; Katz, R. L. Cancer Cytopathology 2010, 118, 175-83.
2. Chiminqgi, M.; Moutereau, S.; Pernet, P.; Conti, M.; Barbu, V.; Lemant, J.; Sacko, M.; Vaubourdolle, M.; Loric, S., Specific real-time PCR vs. fluorescent dyes for serum free DNA quantification, Clinical Chemistry and Laboratory Medicine 2007, 45, 993-95.
3. Crosby, L. D.; Criddle, C. S., DNA hydration studied by pressure perturbation scanning microcalorimetry, Molecular and Cellular Probes 2007, 21, 140-47.
4. Koripelly, G.; Meguellati, K.; Ladame, S. Bioconjugate Chemistry 2010, 21, 2103-09.
5. Okamoto, A. Chemical Record 2010, 10, 188-96.
6. Mullis, K. B., The first polymerase chain reaction, Scientist 2003, 17, 11.
7. Saiki, R. K.; Scharf, S.; Faloona, F.; Mullis, K. B.; Horn, G. T.; Erlich, H. A.; Arnheim, N., Enzymatic amplification of beta-globin genomic sequences and restriction site analysis for diagnosis of sickle cell anemia, Science 1985, 230, 1350-54.
8. Bae, J. H.; Sohn, J. H., Template-blocking PCR: an advanced PCR technique for genome walking, Analytical Biochemistry 2010, 398, 112-16.
9. Tonooka, Y.; Fujishima, M., Comparison and critical evaluation of PCR-mediated methods to walk along the sequence of genomic DNA, Applied Microbiology and Biotechnology 2009, 85, 37-43.
10. Dragan, A. I.; Casas-Finet, J. R.; Bishop, E. S.; Strouse, R. J.; Schenerman, M. A.; Geddes, C. D., Characterization of PicoGreen interaction with dsDNA and the origin of its fluorescence enhancement upon binding, Biophys. J. 2010, in press.
11. Dragan, A. I.; Bishop, E. S.; Casas-Finet, J. R.; Strouse, R. J.; Schenerman, M. A.; Geddes, C. D., Metal-enhanced PicoGreen fluorescence: application for double-stranded DNA quantification, Anal. Biochem. 2010, 396, 8-12.
12. Lakowicz, J. R. Principles of fluorescence spectroscopy, 3rd ed.; Springer Science+Business Media, LLC: New York, 2006.
13. Cosa, G.; Focsaneanu, K. S.; McLean, J. R.; McNamee, J. P.; Scaiano, J. C., Photophysical properties of fluorescent DNA-dyes bound to single- and double-stranded DNA in aqueous buffered solution, Photochem. Photobiol. 2001, 73, 585-99.
14. Singer, V. L.; Jones, L. J.; Yue, S. T.; Haugland, R. P., Characterization of PicoGreen reagent and development of a fluorescence-based solution assay for double-stranded DNA quantitation, Anal. Biochem. 1997, 249, 228-38.
15. Zipper, H.; Brunner, H.; Bernhagen, J.; Vitzthum, F., Investigations on DNA intercalation and surface binding by SYBR Green I, its structure determination and methodological implications, Nucleic Acids Res. 2004, 32, e103.
16. Geddes, C. D. Metal-Enhanced Fluorescence, John Willey & sons, Inc.: Hoboken, N.J., 2010.

17. Aslan, K.; Geddes, C. D., Microwave-accelerated metal-enhanced fluorescence (MAMEF): application to ultra fast and sensitive clinical assays, Journal of Fluorescence 2006, 16, 3-8.
18. Dragan, A. I.; Golberg, K.; Elbaz, A.; Marks, R.; Zhang, Y.; Geddes, C. D. J. Immunol. Methods 2010.
19. Drexhage, K. H., Influence of a dielectric interface on fluorescence decay time, J. Lumin 1970, 1, 693-701.
20. Persson, B. N. J., Theory of dumping of excited molecules located above a metalic-surface, J. Phys. C: Solid State Phys 1978, 11, 4251-69.
21. Lakowicz, J. R.; Shen, Y.; D'Auria, S.; Malicka, J.; Fang, J.; Gryczynski, Z.; Gryczynski, I., Radiative decay engineering. 2. Effects of silver island films on fluorescence intensity, lifetimes, and resonance energy transfer, Anal. Biochem. 2002, 301, 261-77.
22. Geddes, C. D.; Lakowicz, J. R. Journal of Fluorescence 2002, 12, 121-29.
23. Aslan, K.; Gryczynski, I.; Malicka, J.; Matveeva, E.; Lakowicz, J. R.; Geddes, C. D., Metal-enhanced fluorescence: an emerging tool in biotechnology, Current Opinion in Biotechnology 2005, 16, 55-62.
24. Aslan, K.; Malyn, S, N.; Geddes, C. D., Fast and sensitive DNA hybridization assays using microwave-accelerated metal-enhanced fluorescence, Biochemical and Biophysical Research Communications 2006, 348, 612-17.
25. Aslan, K.; Previte, M. J. R.; Zhang, Y. X.; Gallagher, T.; Baillie, L.; Geddes, C. D., Extraction and detection of DNA from *Bacillus anthracis* spores and the vegetative cells within 1 min, Analytical Chemistry 2008, 80, 4125-32.
26. Jelesarov, I.; Crane-Robinson, C.; Privalov, P. L., The energetics of HMG box interactions with DNA: thermodynamic description of the target DNA duplexes, J. Mol. Biol. 1999, 294, 981-95.
27. Park, J. H.; Aluru, N. R. Appl. Phys Lett. 2010, 96, 123703.
28. Aslan, K.; Geddes, C. D., A review of an ultrafast and sensitive bioassay platform technology: microwave-accelerated metal-enhanced fluorescence, Plasmonics 2008, 3, 89-101.
29. McCabe, M.; Maguire, D. J.; Lintell, N. A. Adv. Exp. Med. Biol. 2005, 566, 143-49.
30. Nelson, E. Dynamical Theories of Brownian Motion, Princeton University Press: 1967.
31. Dragan, A. I.; Russell, D. J.; Privalov, P. L. Biopolymers 2009, 91, 95-101.
32. Privalov, P. L.; Dragan, A. I.; Crane-Robinson, C.; Breslauer, K. J.; Remeta, D. P.; Minetti, C. A., What drives proteins into the major or minor grooves of DNA?, J. Mol. Biol. 2007, 365, 1-9.
33. Dragan, A. I.; Privalov, P. L. Methods Enzymol. 2008, 450, 185-99.
34. Favicchio, R.; Dragan, A. I.; Kneale, G. G.; Read, C. M. Methods Mol. Biol. 2009, 543, 589-611.
35. Aslan, K.; Geddes, C. D. Metal-enhanced fluorescence., Geddes, C. D., Ed.; John Wiley & Sons, Inc.: Hoboken, N.J., 2010; Chapter 1.
36. Pribik, R.; Dragan, A. I.; Zhang, Y.; Gaydos, C.; Geddes, C. D., Metal-Enhanced Fluorescence (MEF): Physical characterization of Silver-island films and exploring sample geometries, Chemical Physics Letters 2009, 478, 70-74.
37. Hacia, J. G., Resequencing and mutational analysis using oligonucleotide microarrays, Nat. Genet. 1999, 21, 42-47.
38. Geddes, C. D., Cao, H., Gryczynski, I., Gryczynski, Z., Fang, J. Y., Lakowicz, J. R., Metal-enhanced fluorescence (MEF) due to silver colloids on a planar surface: potential applications of indocyanine green to in vivo imaging, J. Phys. Chem. A, 107 (2003), p. 3443.
39. Geddes, C. D., Parfenov, P., Roll, D., Gryczynski, I., Malicka, J., Lakowicz, J. R., Silver fractal-like structures for metal-enhanced fluorescence: enhanced fluorescence intensities and increased probe photostabilities, J. Fluoresc., 13 (2003), p. 267.
40. Previte, M. J., Zhang, Y., Aslan, K., Geddes, C. D., Real-time thermal imaging of microwave accelerated metal-enhanced fluorescence (MAMEF) based assays on sapphire plates, J. Fluoresc., 17 (2007), p. 639.
41. Tennant, S. M., Zhang, Y., Galen, J. E., Geddes, C. D and M. M. Levine, Ultra-fast and sensitive detection of non-typhoidal *Salmonella* using microwave-accelerated metal-enhanced fluorescence ("MAMEF"), PLoS. One. 6 (2011) e 18700.
42. Zhang, Z., Agreda, P., Kelly, S., Gaydos, C., and C. D. Geddes, Development of a Microwave-Accelerated Metal-Enhanced Fluorescence 40 seconds, <100 cfu/ml point of care assay for the detection of *Chlamydia Trachomatis.*, IEEE Transactions on Biomedical Engineering, 58 (2011) 781-784.
43. Aslan, K., Holley, P., and C. D. Geddes, Microwave-Accelerated Metal-Enhanced Fluorescence (MAMEF) with silver colloids in 96-well plates: Application to ultra fast and sensitive immunoassays, High Throughput Screening and drug discovery, Journal of Immunological Methods, 312 (2006) 137-147.

That which is claimed:

1. A method of decreasing the detection time of a metal-enhanced fluorescence assay used for detecting a single nucleotide sequence or multiple and different target nucleotides, the method comprising: applying a multiplicity of metallic particles to a surface of a quartz substrate used in an assay system, wherein the metallic particles are silver or a combination of silver and gold or a combination of silver and aluminum and wherein the metallic particles are metallic islands, colloids, or nanostructures;

connecting a capture nucleotide to the metallic particles selected from two to seven different capture nucleotides, wherein each of the two to seven different capture nucleotides has binding affinity for a different target nucleotide;

introducing a solution suspected of including the two to seven different target nucleotides, wherein any of the two to seven different target nucleotides present in the sample bind to the corresponding capture nucleotide;

introducing from two to seven different detector nucleotides, wherein each of the detector nucleotides has binding affinity for a different target nucleotide and wherein each of the two to seven detector nucleotides includes a different fluorescence molecule, wherein the different fluorescence molecule is positioned from about 6 nm to about 30 nm from the metallic particles when the detector nucleotide binds to the corresponding target nucleotide that is bound to the capture nucleotide, and wherein the metallic particles are positioned about 6 to 9 nm from each other to avoid inter-molecular energy transfer between fluorescent molecules upon excitation;

applying microwave energy to the assay system for a time period sufficient to increase binding reactions between the two to seven capture nucleotides and/or detector nucleotides with the two to seven different target nucleotides;

applying electromagnetic energy at a different frequency type than the microwave energy to excite the corresponding and different fluorescence molecules, using either one photon or multiphoton excitation; and detecting different fluorescence signals from the different fluorescence molecules by either visual discrimination of emissions having emission wavelengths of different colors or using a variety of filter and diffraction grating to detect the desired emission wavelengths for independent emission detection.

2. The method of claim 1, wherein the nanostructures have a spherical, triangular, elliptical, oblong, rod shape, hexagonal or multifaceted geometric shape.

3. A method for detecting from two to seven different targeted DNAs from different target pathogens in a sample, the method comprising:

providing a system comprising:

immobilized triangular shaped metallic nanoparticles positioned on a surface of a quartz substrate, wherein the immobilized triangular shaped metallic nanoparticles are silver, a combination of silver and gold or a combination of silver and aluminum, wherein each of the triangular shaped immobilized metallic nanoparticles have attached thereto a single capture nucleotide selected from two to seven different types capture nucleotides, wherein each of the two to seven different capture nucleotides has binding affinity for a specific known DNA sequences selected from two to seven different target pathogens in a sample;

two to seven different free capture DNA sequence probes that are complementary to the specific known DNA sequences of the two to seven different targeted DNA, wherein the two to seven different free capture DNA sequences are in an amount sufficient to bind to sequences of the two to seven different target pathogens, and wherein each of the two to seven different free capture DNA sequence probes have attached thereto an excitable energy emitting molecule and are specific for the two to seven different target pathogens suspected of being in the sample, wherein the excitable energy emitting molecules emit energy in the UV to IR range;

contacting the sample with the from two to seven different immobilized capture nucleotide, wherein the DNA sequences of the two to seven different target pathogens bind to the corresponding immobilized capture nucleotide; contacting the bound DNA sequences with the free capture DNA sequence probes, wherein binding of free capture DNA sequence probes to the bound DNA sequences causes the excitable energy emitting molecule to be positioned a distance from about 6 nm to about 30 nm from the immobilized metallic nanoparticles to enhance energy emission, and wherein the immobilized metallic nanoparticles are positioned 6 to 9 nm from each other to avoid inter-molecular energy transfer between excitable energy emitting molecules upon excitation;

applying to the system microwave energy in an amount sufficient to increase the speed of the binding reactions;

irradiating the system with electromagnetic energy in a range from UV to IR to induce emissions by the excitable energy emitting molecules positioned a predetermined distance from the immobilized metallic nanoparticles, wherein the irradiating can be conducted before, during or after the applying of microwave energy; and detecting different emissions by the excitable energy emitting molecules by either visual discrimination of emissions having emission wavelengths of different colors or using a variety of filters and diffraction gratings for independent emission detection.

4. The method of claim 3, wherein the excitable energy emitting molecules are selected from a group consisting of intrinsic fluorophores, extrinsic fluorophores, fluorescent dyes, phosphorus compounds and carbon nanodots.

* * * * *

SEQUENCE LISTING

<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: SYNTHETIC CONSTRUCT

<400> SEQUENCE: 1
agagatatga gcaaaagaa                                                    19

<210> SEQ ID NO 2
<211> LENGTH: 19

```
<212> TYPE: DNA
<213> ORGANISM: Artificial Sequence
<220> FEATURE:
<223> OTHER INFORMATION: SYNTHETIC CONSTRUCT

<400> SEQUENCE: 2
tctctatact cgttttctt                                                   19

<210> SEQ ID NO 3
<211> LENGTH: 19
<212> TYPE: DNA
<213> ORGANISM: Artificial Sequence
<220> FEATURE:
<223> OTHER INFORMATION: SYNTHETIC CONSTRUCT

<400> SEQUENCE: 3
acttggaaag gaggctgga                                                   19

<210> SEQ ID NO 4
<211> LENGTH: 19
<212> TYPE: DNA
<213> ORGANISM: Artificial Sequence
<220> FEATURE:
<223> OTHER INFORMATION: SYNTHETIC CONSTRUCT

<400> SEQUENCE: 4
tgaacctttc ctccgacct                                                   19

<210> SEQ ID NO 5
<211> LENGTH: 19
<212> TYPE: DNA
<213> ORGANISM: Artificial Sequence
<220> FEATURE:
<223> OTHER INFORMATION: SYNTHETIC CONSTRUCT

<400> SEQUENCE: 5
gaaatggaac agagaataa                                                   19

<210> SEQ ID NO 6
<211> LENGTH: 19
<212> TYPE: DNA
<213> ORGANISM: Artificial Sequence
<220> FEATURE:
<223> OTHER INFORMATION: SYNTHETIC CONSTRUCT

<400> SEQUENCE: 6
ctttaccttg tctcttatt                                                   19

<210> SEQ ID NO 7
<211> LENGTH: 19
<212> TYPE: DNA
<213> ORGANISM: Artificial Sequence
<220> FEATURE:
<223> OTHER INFORMATION: SYNTHETIC CONSTRUCT

<400> SEQUENCE: 7
agagataaaa gaatgagca                                                   19

<210> SEQ ID NO 8
<211> LENGTH: 19
<212> TYPE: DNA
<213> ORGANISM: Artificial Sequence
<220> FEATURE:
<223> OTHER INFORMATION: SYNTHETIC CONSTRUCT

<400> SEQUENCE: 8
```

```
tctctatttt cttactcgt                                    19

<210> SEQ ID NO 9
<211> LENGTH: 19
<212> TYPE: DNA
<213> ORGANISM: Artificial Sequence
<220> FEATURE:
<223> OTHER INFORMATION: SYNTHETIC CONSTRUCT

<400> SEQUENCE: 9
gaaatgagaa tagaacaga                                    19

<210> SEQ ID NO 10
<211> LENGTH: 19
<212> TYPE: DNA
<213> ORGANISM: Artificial Sequence
<220> FEATURE:
<223> OTHER INFORMATION: SYNTHETIC CONSTRUCT

<400> SEQUENCE: 10
ctttactctt atcttgtct                                    19
```